United States Patent
Cleemann et al.

(10) Patent No.: US 9,133,276 B2
(45) Date of Patent: Sep. 15, 2015

(54) PRODRUGS COMPRISING AN EXENDIN LINKER CONJUGATE

(75) Inventors: Felix Cleemann, Heidelberg (DE); Ulrich Hersel, Heidelberg (DE); Torben Lessman, Mannheim (DE); Harald Rau, Heidelberg (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 13/822,170

(22) PCT Filed: Sep. 16, 2011

(86) PCT No.: PCT/EP2011/066097
§ 371 (c)(1),
(2), (4) Date: Mar. 11, 2013

(87) PCT Pub. No.: WO2012/035139
PCT Pub. Date: Mar. 22, 2012

(65) Prior Publication Data
US 2013/0189328 A1 Jul. 25, 2013

(30) Foreign Application Priority Data
Sep. 17, 2010 (EP) .................................. 10177327

(51) Int. Cl.
A61K 38/16 (2006.01)
C07K 14/00 (2006.01)
A61P 3/10 (2006.01)
C07K 17/08 (2006.01)
A61K 47/48 (2006.01)

(52) U.S. Cl.
CPC ........... C07K 17/08 (2013.01); A61K 47/48215 (2013.01); A61K 47/48338 (2013.01); A61K 47/48784 (2013.01)

(58) Field of Classification Search
CPC .................. A61K 47/48215; A61K 47/48784; A61K 47/48338; C07K 17/08
See application file for complete search history.

(56) References Cited

U.S. PATENT DOCUMENTS

| | | | |
|---|---|---|---|
| 5,424,286 A | 6/1995 | Eng | |
| 5,514,379 A | 5/1996 | Weissleder et al. | |
| 5,634,943 A | 6/1997 | Villain et al. | |
| 6,271,345 B1 | 8/2001 | Waldmann et al. | |
| 6,506,724 B1 | 1/2003 | Hiles et al. | |
| 6,537,569 B2 | 3/2003 | Cruise | |
| 6,602,952 B1 | 8/2003 | Bentley et al. | |
| 7,157,555 B1 | 1/2007 | Beeley et al. | |
| 7,393,953 B2 | 7/2008 | Zhao et al. | |
| 7,585,831 B2 | 9/2009 | Lang | |
| 7,585,837 B2 | 9/2009 | Shechter et al. | |
| 7,879,588 B2 | 2/2011 | Vetter et al. | |
| 7,968,085 B2 | 6/2011 | Hersel et al. | |
| 8,377,917 B2 | 2/2013 | Hersel et al. | |
| 2001/0048947 A1 | 12/2001 | Rowe et al. | |
| 2003/0023023 A1 | 1/2003 | Harris et al. | |
| 2003/0078314 A1 | 4/2003 | Johnson et al. | |
| 2003/0083389 A1 | 5/2003 | Kao et al. | |
| 2003/0166833 A1 | 9/2003 | Lutolf et al. | |
| 2003/0220245 A1 | 11/2003 | Hubbell et al. | |
| 2004/0023842 A1 | 2/2004 | Pathak et al. | |
| 2006/0002890 A1 | 1/2006 | Hersel et al. | |
| 2006/0115865 A1 | 6/2006 | Ouyang et al. | |
| 2007/0207210 A1 | 9/2007 | Brown et al. | |
| 2007/0275030 A1 | 11/2007 | Muratoglu et al. | |
| 2008/0187568 A1 | 8/2008 | Sawhney | |
| 2008/0220047 A1 | 9/2008 | Sawhney et al. | |
| 2008/0241102 A1 | 10/2008 | Hersel et al. | |
| 2008/0293827 A1 | 11/2008 | Lee et al. | |
| 2009/0030102 A1 | 1/2009 | Nelles et al. | |
| 2010/0291021 A1 | 11/2010 | Vetter et al. | |

(Continued)

FOREIGN PATENT DOCUMENTS

DE 10 2008 003 566 A1 7/2009
DE 10 2008 003 568 A1 7/2009

(Continued)

OTHER PUBLICATIONS

Definition of moiety, from http://dictionary.reference.com/browse/moieties, pp. 1-3, accessed Aug. 26, 2010.*
Christensen et al, Lixisenatide, a noveL GLP-1 receptor agonist for the treatment of type 2 diabetes mellitus, IDrugs, 2009, 12, pp. 503-513.*
Lin-Chien-Chi, e al.: "Glucagon-like peptide 1 functionalized PEG hydrogels promote survival and function of encapsulated pancreatic beta-cells." Biomacromolecules; vol. 10, No. 9, Sep. 14, 2009 pp. 2460-2467.

(Continued)

Primary Examiner — Julie Ha
Assistant Examiner — Li Ni Komatsu
(74) Attorney, Agent, or Firm — Morrison & Foerster LLP

(57) ABSTRACT

The present invention relates to a prodrug or a pharmaceutically acceptable salt thereof comprising an exendin linker conjugate D-$L^1$, wherein D represents an exendin moiety; and -$L^1$ is represented by formula (I),

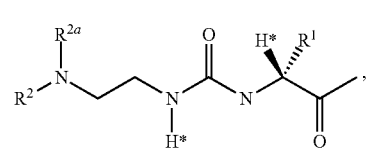

(I)

wherein the dashed line indicates the attachment to one of the amino groups of the exendin moiety by forming an amide bond. The invention further relates to pharmaceutical compositions comprising said prodrugs as well as their use as a medicament for treating or preventing diseases or disorders which can be treated by exendin.

26 Claims, 1 Drawing Sheet

(56) References Cited

U.S. PATENT DOCUMENTS

| | | |
|---|---|---|
| 2011/0009315 A1 | 1/2011 | Hersel et al. |
| 2011/0053848 A1 | 3/2011 | Cleeman et al. |
| 2011/0112021 A1 | 5/2011 | Rau et al. |
| 2012/0058084 A1 | 3/2012 | Rau et al. |
| 2012/0156259 A1 | 6/2012 | Rau et al. |
| 2012/0183616 A1 | 7/2012 | Sprogoe et al. |
| 2012/0184489 A1 | 7/2012 | Rau et al. |
| 2012/0253071 A1 | 10/2012 | Rau et al. |
| 2013/0189328 A1 | 7/2013 | Rau et al. |

FOREIGN PATENT DOCUMENTS

| | | |
|---|---|---|
| EP | 0 214 826 A2 | 3/1987 |
| EP | 0 368 187 A2 | 5/1990 |
| EP | 0 375 437 A2 | 6/1990 |
| EP | 0419504 A1 | 4/1991 |
| EP | 0627911 A1 | 12/1994 |
| EP | 0 678 522 A1 | 10/1995 |
| EP | 0 885 961 A1 | 12/1998 |
| EP | 0885961 A1 | 12/1998 |
| EP | 1019446 A1 | 7/2000 |
| EP | 1053019 A1 | 11/2000 |
| EP | 1 670 265 A1 | 6/2006 |
| EP | 2596805 A1 | 5/2013 |
| JP | 2005239736 A2 | 5/2005 |
| JP | 2005-239736 A | 9/2005 |
| WO | 89/10937 A1 | 11/1989 |
| WO | WO 92/00321 A1 | 1/1992 |
| WO | WO9317669 A1 | 9/1993 |
| WO | WO 97/04796 A1 | 2/1997 |
| WO | WO 99/14259 A1 | 3/1999 |
| WO | WO 99/25354 A2 | 5/1999 |
| WO | WO 99/25727 A2 | 5/1999 |
| WO | WO 99/25728 A1 | 5/1999 |
| WO | WO 99/30727 A1 | 6/1999 |
| WO | WO 99/34833 A1 | 7/1999 |
| WO | WO 99/40788 A1 | 8/1999 |
| WO | WO0021572 A2 | 4/2000 |
| WO | WO0044808 A1 | 8/2000 |
| WO | WO0069900 A2 | 11/2000 |
| WO | WO0147562 A2 | 7/2001 |
| WO | WO0185180 A1 | 11/2001 |
| WO | 02/17880 A2 | 3/2002 |
| WO | WO02083180 A1 | 10/2002 |
| WO | WO02089789 A1 | 11/2002 |
| WO | WO02094200 A2 | 11/2002 |
| WO | 03/035244 A1 | 5/2003 |
| WO | WO03035244 A1 | 5/2003 |
| WO | WO03049677 A2 | 6/2003 |
| WO | 03/098142 A1 | 11/2003 |
| WO | WO03101425 A1 | 12/2003 |
| WO | WO03104426 A2 | 12/2003 |
| WO | WO2004043493 A1 | 5/2004 |
| WO | WO2004089280 A2 | 10/2004 |
| WO | WO2004108070 A2 | 12/2004 |
| WO | WO2005034909 A2 | 4/2005 |
| WO | WO2005099768 A2 | 10/2005 |
| WO | WO2005099769 A2 | 10/2005 |
| WO | WO2006003014 A2 | 1/2006 |
| WO | 2006/038462 A1 | 4/2006 |
| WO | WO2006038462 A1 | 4/2006 |
| WO | WO2006047451 A2 | 5/2006 |
| WO | WO2006073396 A1 | 7/2006 |
| WO | WO 2006/115865 A1 | 11/2006 |
| WO | WO2006136586 A2 | 12/2006 |
| WO | WO2007053946 A1 | 5/2007 |
| WO | WO2007082088 A2 | 7/2007 |
| WO | WO2007140312 A2 | 12/2007 |
| WO | WO2008015099 A2 | 2/2008 |
| WO | WO2008034122 A2 | 3/2008 |
| WO | WO2008116913 A2 | 10/2008 |
| WO | WO2008125655 A1 | 10/2008 |
| WO | WO2008148839 A2 | 12/2008 |
| WO | WO2009010428 A1 | 1/2009 |
| WO | WO2009095479 | 8/2009 |
| WO | WO2009095479 A2 | 8/2009 |
| WO | WO2009102952 A2 | 8/2009 |
| WO | WO2009134336 A1 | 11/2009 |
| WO | WO2011012715 A1 | 2/2011 |
| WO | WO2011012718 A1 | 2/2011 |
| WO | WO2011012719 A1 | 2/2011 |
| WO | WO2011051406 A1 | 5/2011 |
| WO | WO2012035139 A1 | 3/2012 |

OTHER PUBLICATIONS

Young et al., "Glucose-Lowering and Insulin-Sensitizing Actions ofExendin-4: Studies in Obese Diabetic (ob/ob, db/db) Mice, Diabetic Fatty Zucker Rats, and Diabetic Rhesus Monkeys (*Macaca mulatta*)", Diabetes, May 1999, pp. 1026-1034, vol. 48.

Zhao et al., "Novel degradable poly(ethylene glycol) hydrogels for controlled release of protein," J. Pharm. Sciences, 1998, 1450-1458, vol. 87, No. 11.

Zhu et al., "Stabilization of proteins encapsulated in injectable poly (lactide-co-glycolide)," Nat. Biotechnol. 18 (2000) 52-57.

Auzanneau et al., "Synthesis, characterization, and biocompatability of PEGA resins", "Journal of Peptide Science", May 1995, pp. 31-44, vol. 1.

Belcheva et al., "Crosslinked Poly( ethylene oxide) for drug release systems", Macromol. Symp., 1996, pp. 193-211, vol. 103, Huethig & WepfVerlag, Zug, Switzerland.

Bundgaard et al. "Hydrolysis and Rearrangement of Phthalamic Acid Derivatives and Assessment of Their Potential As Prodrug Forms for Amines" Acta Pharmaceutica Nordica, Elsevier Science Publishers, Amsterdam, NL, vol. 2, No. 5, 1990, pp. 333-342.

Dimitrov et al., "Preparation and Characterization of Polyethylene Oxide Hydrogels with Cytisine", Acta Pharmaceutica Turcica, 2004, pp. 49-54, vol. 46.

Diabetes Mellitus, from Merck Manual, pp. 1-22, accessed Apr. 2, 2013.

Olofsson et al., recent advances in crosslinked dendritic networks, Applied Polymer Science, 2013, 39876, pp. 1-13.

Wathier et al., Dendritic macromers as in situ polymerizing biomaterials for securing, J. Am. Chem. Soc., 2004 vol. 126, pp. 12744-12746.

Fehse et al., "Exenatide Augments First- and Second-Phase Insulin Secretion in Response to Intravenous Glucose in Subjects with Type 2 Diabetes", J Clin. Endocrinol. Metab., 2005, pp. 5991-5997, vol. 90, No. 11, us.

Nathan et al., Diabetologia (2008) 51 :8-11.

International Search Report issued in PCT/EP2010/061159 as mailed on Nov. 17, 2010.

International Search Report issued in PCT/EP2010/061160 as mailed on Nov. 16, 2010.

International Search Report issued in PCT/EP2011/066097 as mailed on Feb. 27, 2012.

Izutsu, K., "Stabilization of Therapeutic Proteins by Chemical and Physical Methods" Methods in Molecular Biology 308:287-292 (2005).

Crosslinking Technical Handbook, from Thermo Scientific, published on Apr. 2009, pp. 1-48.

Office Action issued on Jun. 23, 2014 in U.S. Appl. No. 13/387,940.

Antczak et al., "A New Acivicin Prodrug Designed for Tumor-Targeted Delivery", "Bioorganic & Medicinal Chemistry", 2001, pp. 2843-2848, vol. 9, Publisher: Elsevier Science Ltd.

Attwood et al., "Influence of gamma irradiation on the rheological properties of gels of the poloxamine, Synperonic T908", International Journal of Pharmaceutics, vol. 70, No. 1-2, 1991, pp. 147-152.

"Beaumont et al., Design of Ester Prodrugs to Enhance Oral Absorption of Poorly Permeable Compounds: Challenges to theDiscovery Scientist, Current Drug Metabolism, 2003, 4, 461-485."

Bernkop-Schnurch, 1997, Journal of Controlled release 47 (1997) 113-121.

Bhatt et al., "Synthesis and in Vivo Antitumor Activity of Poly(L-glutamic acid) Conjugates of 20(S)-Camptothecin", "J. Med. Chem.", 2003, p. 190-193, vol. 46.

Boas et al., "Dendrimers in drug research", Chem. Soc. Rev., 2004, pp. 43-63, vol. 33.

(56) References Cited

OTHER PUBLICATIONS

Cadee et al., "Release of recombinant human interleukin-2 from dextran-based hydrogels", J. Controlled Release, 2002, 1-13, vol. 78.
Caliceti et al., "Pharmacokinetic and biodistribution properties of poly(ethylene glycol)-protein conjugates", Advanced Drug Delivery, 2003, 1261-1277, vol. 55.
Cavallaro et al., "Polymeric Prodrug for Release of an Antitumoral Agent by Specific Enzymes", Bioconjugate Chemistry, 2001, 143-151, vol. 12.
Cheng et al., "Synthesis of Linear, Beta-Cyclodextrin-Based Polymers and Their Camptothecin Conjugates", Bioconjugate Chemistry, 2003, 1007-1017, vol. 14.
Choi et al, "Control of Blood Glucose by Novel GLP-1 Delivery Using Biodegradable Triblock Copolymer of PLGA-PEG-PLGA in Type 2 Diabetic Rats," Pharmaceutical Research, vol. 21, No. 5, pp. 827-831 (2004).
Christensen et al, Lixisenatide, a novel GLP-1 receptor agonist for the treatment of type 2 diabetes mellitus, I Drugs, 2009, 12, pp. 503-513.
Defronzo et al., "Effects of Exenatide (Exendin-4) on Glycemic Control and Weight Over 30 Weeks in Metformin-Treated Patients With Type 2 Diabetes", Diabetes Care, May 2005, pp. 1092-1100, vol. 28, No. 5.
Definition of derivatives and analogues, from http://cancerweb.ncl.ac.uk!cgi-bin/omd?query=derivative and http://cancerweh.ncl.ac.uk!cgi-hin/omd?analogue, pp. 1-5, accessed Jul. 7, 2005.
Definition of mimetics, from http://www.thefreedictionary.com/p/mimetic, pp. 1-2, accessed Oct. 11, 2013.
Definition of the like, from http://www.thefreedictionary.com/p/the%20like, p. 1, accessed Oct. 15, 2013.
Domb et al., "Chemical interactions between drugs containing reactive amines with hydrolyzable insoluble biopolymers in aqueous solutions," Pharm. Res. 11(6) (1994) 865-868.
Duncan et al., "Polymer-drug conjugates, PDEPT and PELT: basic principles for design and transfer from the laboratory to clinic", J. Control. Release, 2001, 74:135-146.
Dupre et al., "Exendin-4 Normalized Postcibal Glycemic Excursions in Type I Diabetes", J Clin. Endocrinol. Metab., 2004, pp. 3469-3473, vol. 89, No. 7, US.
Edwards et al., "Exendin-4 reduces fasting and postprandial glucose and decreases energy intake in healthy volunteers", Am. J. Physiol. Endocrinol. Metab. 2001, pp. 155-161, vol. 281, US.
Ellman et al., "A new and rapid colorimetric determinationof acetylcholinesterase activity," Biochem. Pharmacol., 1961, 7, 88-95.
Eng et al., "Isolation and characterization of exendin-4, an exendin-3 analogue, from heloderma suspectum venom," J. Bio. Chem., 1992, 7402-7405, vol. 267, No. 11.
English et al., "Orally effective acid prodrugs of the β-lactamase inhibitor sulbactam," J. Med. Chem., 1990, 344-347, vol. 33.
Esfand et al., "Poly(amidoamine) (PAMAM) dendrimers: from biomimicry to drug delivery and biomedical applications", Drug Discov. Today, 2001, pp. 427-436, vol. 6, No. 8.
Franssen et al., "Controlled release of a model protein from enzymatically degrading dextran microspheres," J. Control. Release, 59(2):219-228, 1999.
Garman et al., "The Preparation and Properties of Novel Reversible Polymer-Protein Conjugates", FEBS Lett., 1987, 223(2):361-365.
Goke et al., "Exendin-4 Is a High Potency Agonist and Truncated Exendin-(9-39)-amide an Antagonist at the Glucagon-like Peptide 1-(7-36)-amide Receptor ofInsulin-secreting B-Cells", J. of Biolo. Chern., Sep. 15, 1993, pp. 19650-19655, vol. 268, No. 26, US.
Gomes et al.,"Cyclization-activated prodrugs." Molecules (Basel, Switzerland) 2007, vol. 12, No. 11, 2007, pp. 2484-2506.
Grayson et al., "Convergent Dendrons and Dendrimers: from Synthesis to Applications", Chern. Rev., 2001, pp. 3819-3867, vol. 101, Berkeley, CA, US.
Greenwald et al., "A New Aliphatic Amino Prodrug System for the Delivery of Small Molecules and Proteins Utilizing Novel PEG Derivatives", "J. Med. Chem.", 2004, pp. 726-734, vol. 47, Publisher: American Chemical Society.

Greenwald et al., "Drug Delivery Systems Based on Trimethyl Lock Lactonization Poly(ethylene glycol) Prodrugs of Amino-Containing Compounds", "J. Med. Chem.", 2000, pp. 475-487, vol. 43, Publisher: American Chemical Society.
Greenwald et al., "Drug Delivery Systems Employing 1,4- or 1,6-Eiimination: Poly(ethylene glycol) Prodrugs of Amine-Containing Compounds", "J. Med. Chem.", 1999, pp. 3657-3667, vol. 42, Publisher: American Chemical Society.
Greig, et al: New therapeutic strategies and drug candidates for neurodegenerative diseases: p53 and TNF-alpha inhibitors, and GLP-1 receptor agonists. Annals of the New York Academy of Sciences, vol. 1035, 2004, pp. 290-315.
Gude et al., "An accurate method for the quantitation of Fmoc-derivatizated solid phase," (2002) Letters in Peptide Science 9(4): 203-206.
Gutniak et al., "Antidiabetogenic effect of glucagon-like peptide-! (7-36)amide in normal subjects and patients with diabetes mellitus", NE J. of Med., May 14, 1992, pp. 1316-1322, vol. 326, No. 20.
Han, Targeted Prodrug Design to Optimize Drug Delivery, AAPS PharmSci 2000, 2, article 6, pp. 1 to 11.
Hayashi et al., "Development of oligoarginine-drug conjugates linked to new peptidic self-cleavable spacers toward effective intestinal absorption" Bioorganic and Medicinal Chemistry Letters Sep. 15, 2007 GB, vol. 17, No. 1a, Sep. 15, 2007, pp. 5129-5132.
Hennink et al., "Novel crosslinking methods to design hydrogels", "Advanced Drug Delivery Reviews", 2002, pp. 13-36, vol. 54, Publisher: Elsevier Science B.V.
Herman (Ed.), "Biodegradable Polymers, Medical Applications", Encyclopedia of Polymer Science and Technology, 2004, pp. 263-285, vol. 5, John Wiley & Sons, Inc., Hoboken, NJ.
Hinds et al., Effects of PEG conjugation of insulin properties, Advanced Drug Delivery Reviews vol. 54, 2002, 505-530.
Hinds et al., Journal of Controlled Release, 2005 (104), 447-460.
Hoffman, "Hydrogels for biomedical applications", "Advanced Drug Delivery Reviews", 2002, pp. 3-12, vol. 43, Publisher: Elsevier Science B.V.
Human insulin amino acid sequence, from http://dailymed.nlm.nih.gov/dailymed/fda/fdaDrugXsl.cfm?id=7043, p. 1, accessed Oct. 16, 2013.
Huynh et al., "Controlled release of insulin from pH/temperature-sensitive injectable pentablock copolymer hydrogel", Journal of Controlled Release, vol. 137, No. 1, 2009 pp. 20-24.
Huynh et al., "Functionalized injectable hydrogels for controlled insulin delivery" Biomaterials (Jun. 2008) pp. 2527-2534, vol. 29, No. 16.
International Search Report corresponding to PCT/EP2005/007316, dated Oct. 16, 2006.
International Search Report corresponding to PCT/EP2008/056981, dated Jun. 26, 2009.
International Search Report corresponding to PCT/EP2009/051079, dated Jul. 22, 2009.
International Search Report corresponding to PCT/EP2010/061155, dated Nov. 26, 2010.
International Search Report corresponding to PCT/EP2010/066404, dated Dec. 10, 2010.
Jeong et al., "Thermogelling biodegradable copolymer aqueous solutions for injectable protein delivery and tissue engineering", "Biomacromolecules", 2002, pp. 865-868, vol. 3.
Kanjickal et al., "Effects of sterilization on poly(ethylene glycol) hydrogels", J. Biomed. Mater. Res. Part A., Jan. 9, 2008, pp. 608-617, Wiley InterSciencc (www.interscience.wiley.com).
Kim et al., "Effects of Once-Weekly Dosing of a Long-Acting Release Formulation ofExenatide on Glucose Control and Body Weight in Subjects With Type 2 Diabetes", Diabetes Care, Jun. 2007, pp. 1487-1493, vol. 30, No. 6.
Lee et al., "Drug Delivery Systems Employing 1,6-Eiimination: Releasable Poly(ethylene glycol) Conjugates of Proteins", "Bioconjugate Chemistry", 2001, pp. 163-169, vol. 12, Publisher: American Chemical Society.
Lee et al., "Synthesis, Characterization, and Pharmacokinetic Studies of PEGylated Glucagon-like Peptide-1", Bioconjug. Chem., 2005, pp. 377-382, vol. 16, No. 2.

(56) References Cited

OTHER PUBLICATIONS

Lin et al., "Glucagon-like peptide-1 functionalized PEG hydrogels promote survival and function of encapsulated pancreatic beta-cells," Biomacromolecules vol. 10. No. 9, 2009 pp. 2460-2467.
Linnebjerg, et al: "Exenatide: Effect of injection time on postprandial glucose in patients with Type 2 diabetes" Diabetic Medicine, vol. 23, No. 3, 2006, pp. 240-245.
Lucke et al., Pharm. Res. 19 (2002) 175-181.
Luo et al., "A hyalurionic acid-laxol antitumor bioconjugate targeted to cancer cells", "Biomacromolecules", 2000, pp. 208-218, vol. 1.
Markussen et al., J. Biol. Chem. 1991, 266, 18814-18818.
Material Safety Data Sheet-40 kDa Methoxy Poly(Ethylene Glycol) Maleimido-Propionamide, ChiroTech Technology Ltd.—Product No. 008-016, No. 1, 2 pages (Feb. 14, 2005).
Matsumura et al., "A New Concept for Macromolecular Therapeutics in Cancer Chemotherapy: Mechanism of Tumoritropic Accumulation of . . . ", "Cancer Research", Dec. 1986, pp. 6387-6392, vol. 46.
Minkov et al., "Structural Studies of Radiation-corsslinked Poly( ethylene oxide)", J. Polymer Sci: Part B: Polymer Phys., 1989, pp. 621-642, vol. 27, John Wiley & Sons, Inc., Hoboken, NJ.
Muller, Prodrug Approaches for Enhancing the Bioavailability of Drugs with Low Solubility, Chemistry & Biodiversity, 2009, 6, 2071-2083.
Na et al., "Monitoring of peptide acylation inside degrading PLGA microspheres by capillary electrophoresis and MALDI-TOF mass spectrometry", "Journal of Controlled Release", 2003, pp. 291-299, vol. 92, Publisher: Elsevier B. V.
Nauck et al., "Glucagon-like peptide I and its derivatives in the treatment of diabetes", Regulatory Peptides, 2005, pp. 135-148, vol. I28.
Peppas et al., "Hydrogels in pharmaceutical formulations", Eur. J. Pharm. Biopharm., 2000, pp. 27-46, vol. 50.
Perez-Tilve et al., "Exendin-4 Potently Decreases Ghrelin Levels in Fasting Rats", Diabetes, Jan. 2007, pp. 143-151, vol. 56.
Prestwich, et al: "Controlled chemical modification of hyaluronic acid: synthesis, applications, and biodegradation of hydrazide derivatives" Journal of Controlled Release, vol. 53, No. 1-3, 1998, pp. 93-103.
Ratner, et al: "Long-term effects of exenatide therapy over 82 weeks on glycaemic control and weight in over-weight metformin-treated patients with type 2 diabetes mellitus." Diabetes, Obesity & Metabolism, vol. 8, No. 4, p. 419-428, 2006.
Rosiak et al., "Hydrogels and their medical applications", Nuclear Instruments and Methods in Physics Research B, 1999, pp. 56-64, vol. 151, Elsevier Science, BY, Netherlands.
Rosiak et al., "Synthesis of hydrogels by irradiation of polymers in aqueous solution", Radiation Physics and Chemistry, 1999, pp. 139-151, vol. 55, Elsevier Science Ltd., Netherlands.
Rouquerol et al. , "Recommendations for the characterization of porous solids", "Pure and Applied Chemistry", 1994, pp. 1739-1758, vol. 66, No. 8.
Satchi-Fainaro et al., "PDEPT: Polymer-Directed Enzyme Prodrug Therapy. 2. HPMA Copolymer-bela-lactamase and HPMA Copolymer-C-Oax as a Model . . . ", "Bioconjugate Chemistry", 2003, pp. 797-804, vol. 14, Publisher: American Chemical Society.
Sawhney et al., "Bioerodible Hydrogels Based on Photopolymerized Poly( ethylene glycol)-co-poly(alpha-hydroxy acid) Diacrylate Macromers", "Macromolecules", 1993, pp. 581-587, vol. 26.
Shafer et al., "Participation of a Neighboring Amide Group in the Decomposition of Esters and Amides of Substituted Phthalamic Acids" J. Org. Chem, 28(7):1899-1901, 1963.
Shan et al., "Prodrug Strategies Based on Intramolecular Cyclization Reactions", J. Pharm. Sci., 86(7):765-777, 1997.
Shao et al., Stabilization of pH-induced degradationof porcine insulin in biodegradable polyester microspheres, Pharm. Dev. Technol. 4(4):633-642, 1999.
Shao et al., "Porcine insulin biodegradable polyester microspheres: stability and in vitro release characteristics," Pharm. Dev. Technol. 5(1):1-9, 2000.
Shechter et al., "[2-Sulfo-9-fluorenylmethoxycarbonylh-exendin-4-a long-acting glucose-lowering prodrug", Biochem, Biophys. Res. Commun., 2003, pp. 386-391, vol. 305.
Shechter et al., "Reversible pegylation of insulin facilitates its prolonged action in vivo," Eur. J. Pharm. Biopharm. 2008(70), 19-28.
Singh et al., Recent Trends in Targeted Anticancer Prodrug and Conjugate Design, Curr. Med. Chem. 2008, 15(18):1802-1826.
Sintzel et al., "Influence of irradiation sterilization on polymers used as drug carriers—A review", Drug Dev. Ind. Pharm., 23(9):857-878, 1997.
Sohma et al., "Development of 1-36 water-soluble prodrugs of the HIV-1 protease inhibitor KNI-727: Importance of the conversion time for higher gastrointestinal absorption of prodrugs based on spontaneous chemica 1 cleavage." J. Med. Chem., 46(19):4124-4135, 2003.
Surini et al., "Release phenomena of insulin from an implantable device composed of a polyion complex of chitosan and sodium hyaluronate", J. Control. Release, 2003, 291-301, vol. 90(3).
Testa, Prodrug Research: Futile or Fertile?, Biochem. Pharm. 2004, 68, 2097-2106.
Tsubery et al., "Prolonging the action of protein and peptide drugs by a novel approach of reversible polyethylene glycol modification", J. Biol. Chem., Sep. 10, 2004, pp. 38118-38124, vol. 279, No. 37.
Wiwattanapatapee et al., "Dendrimers conjugates for colonic delivery of 5-aminosalicylic acid", J. Control. Release, 2003, 1-9, vol. 88.
Ettmayer, et al. "Lessons Learned from Marketed and Investigational Prodrugs", J. Med. Chem. 2004, 47(10), 2393-2404.
Office Action issued in U.S. Appl. No. 13/387,959 dated Nov. 28, 2014.
Final Office Action issued in U.S. Appl. No. 10/960,851 as mailed on Oct. 5, 2009.
Final Office Action issued in U.S. Appl. No. 10/960,851 as mailed on Oct. 18, 2010.
Non Final Office Action issued in U.S. Appl. No. 10/960,851 as mailed on Dec. 29, 2008.
Non Final Office Action issued in U.S. Appl. No. 10/960,851 as mailed on Feb. 18, 2010.
Notice of Allowance issued in U.S. Appl. No. 10/960,851 as mailed on Mar. 3, 2011.
Restriction Requirement issued in U.S. Appl. No. 10/960,851 as mailed on Jul. 24, 2007.
Restriction Requirement issued in U.S. Appl. No. 10/960,851 as mailed on Jun. 23, 2008.
Supplemental Notice of Allowability issued in U.S. Appl. No. 10/960,851 as mailed on Apr. 26, 2011.
Non Final Office Action issued in U.S. Appl. No. 12/663,628 as mailed on Dec. 5, 2013.
Non Final Office Action issued in U.S. Appl. No. 12/663,628 as mailed on May 10, 2013.
Restriction Requirement issued in U.S. Appl. No. 12/663,628 as mailed on Nov. 26, 2012.
Restriction Requirement issued in U.S. Appl. No. 12/663,628 as mailed on Oct. 3, 2012.
Non Final Office Action issued in U.S. Appl. No. 12/865,693 as mailed on Jan. 16, 2014.
Non Final Office Action issued in U.S. Appl. No. 12/865,693 as mailed on Jul. 18, 2013.
Restriction Requirement issued in U.S. Appl. No. 12/865,693 as mailed on Jan. 9, 2013.
Non Final Office Action issued in U.S. Appl. No. 13/111,777 as mailed on Dec. 27, 2013.
Restriction Requirement issued in U.S. Appl. No. 13/111,777 as mailed on Oct. 16, 2012.
Final Office Action issued in U.S. Appl. No. 13/387,959 as mailed on Apr. 10, 2014.
Non Final Office Action issued in U.S. Appl. No. 13/387,959 as mailed on Aug. 30, 2013.
Restriction Requirement issued in U.S. Appl. No. 13/387,959 as mailed on Jul. 10, 2013.
Restriction Requirement issued in U.S. Appl. No. 13/387,971 as mailed on Nov. 22, 2013.
Final Office Action issued in U.S. Appl. No. 13/505,214 as mailed on Apr. 3, 2014.

(56) References Cited

OTHER PUBLICATIONS

Non Final Office Action issued in U.S. Appl. No. 13/505,214 as mailed on Nov. 26, 2013.
Non Final Office Action issued in U.S. Appl. No. 13/822,170 as mailed on Mar. 3, 2014.
Restriction Requirement issued in U.S. Appl. No. 13/822,170 as mailed on Nov. 22, 2013.
Belikov, "Fannazevticheskaya Khimiya", M., Vysshaya shoka, 1993, t. I, str. 43-47 (=Pham1accutical Chemistry, Moscow, High School, 1993, vol. 1 p. 43-47) (article in Russian with English abstract), Abstract only.
Harkevich, "Farmakologiya", M., Medizina, 1987, str.47-48 (=Pharmacology, Moscow, Medicine, 1987, p. 47-48) with Engl (article in Russian with English abstract), Abstract only.
Harkevich, "Farmakologiya", M., Medizina, 1987, str.50-52 (=Pharmacology, Moscow, Medicine, 1987, p. 50-52). (article in Russian with English abstract), Abstract only.
Jarry et al., Chem. Pharm. Bull., 50(10), 1335-1340, 2002.
Kudrin, "Problemy vzaimodeistviya lekarstvennykh veshestv", Farmaziya, 1983, No. 2, str. 71 (=Problems of Interaction of medicinal substances, Pharmacy, 1983, No. 2, p. 71). (article in Russian with English abstract), Abstract only.
Nektar, Inc., "Nektar Molecule Engineering—Polyethylene Dlycol and Derivatives for Advanced PEGylation", "Nektar Advanced PEGylation (Catalog 2004)", 2003.
Physicians' Desk Reference 57th Edition, 2003, pp. 2768-2772.

* cited by examiner

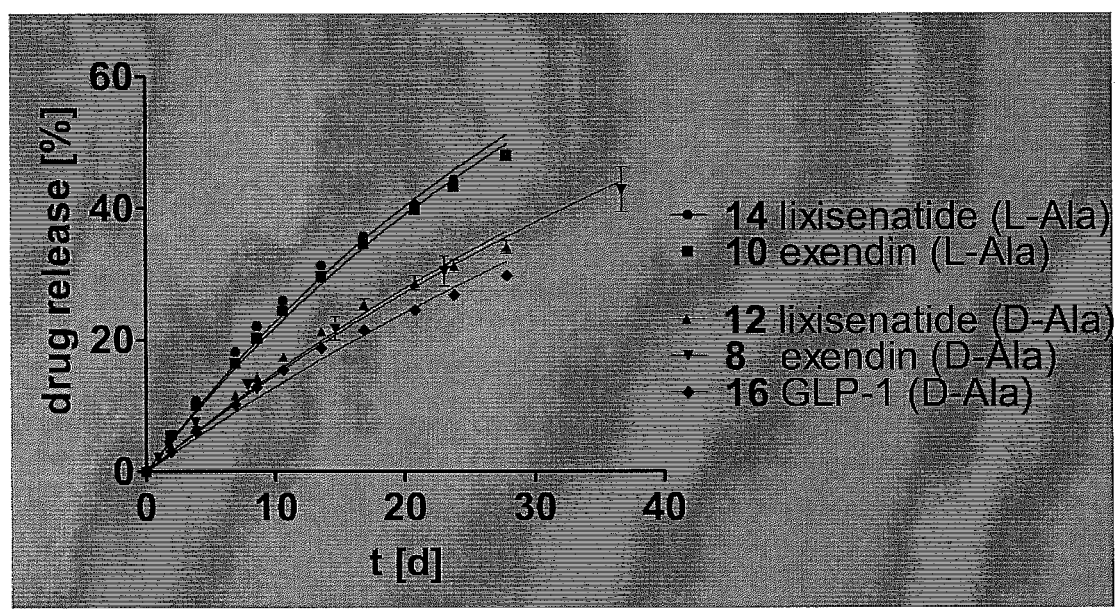

PRODRUGS COMPRISING AN EXENDIN LINKER CONJUGATE

The present application is a '371 of PCT Application No. PCT/EP11/66097, filed on Sep. 16, 2011.

INCORPORATION BY REFERENCE OF SEQUENCE LISTING

The Sequence Listing in the ASCII text file, named as 29743_SEQ1toSEQ22_ST25_edited.txt of 11KB, created on Feb. 26, 2015, and submitted to the United States Patent and Trademark Office via EFS-Web, is incorporated herein by reference.

The present invention relates to exendin prodrugs, pharmaceutical compositions comprising said prodrugs as well as their use as a medicament for treating or preventing diseases or disorders which can be treated by exendin.

Exendin-4 is a 39-amino acid peptide, isolated from the salivary secretions of the venomous Gila monster (Heloderma suspectum). It has some sequence similarity to several members of the glucagon-like peptide family, with the highest homology of 53% being to glucagon-like peptide-1 [7-36]-amide (GLP-1). Exendin-4 acts as a GLP-1 agonist on the GLP-1 receptor and bears GLP-1-like insulin secretagogue action in isolated rat islets. Exendin-4 is a high potency agonist and truncated exendin-(9-39)-amide an antagonist at the glucagon-like peptide 1-(7-36)-amide receptor of insulin-secreting beta-cells. (see e.g. J. Biol. Chem. 268(26):19650-19655). Exendin-4 ("exenatide") was approved recently in the US and EU for improving glycemic control in patients with type 2 diabetes taking metformin and/or a sulfonylurea but have not achieved adequate glycemic control.

Current therapy with exenatide requires frequent injections (bidaily), resulting in high plasma levels after injection, which is correlated to nausea (see Nauck M. A., Meier J. J. (2005), *Regul Pept.* 128(2):135-148), and to low trough concentrations, leading to incomplete glycemic control (see Kim D., et al. (2007), Diabetes Care. 30(6):1487-1493). To overcome these problems a longer-acting formulation for exendin-4 is highly desirable.

Ideally, the peptide is formulated in a fashion that provides for a sustained plasma level in human for at least one week after application to a human body resulting in a once-weekly or longer injection frequency. Several long-acting exendins have been proposed.

To enhance physicochemical or pharmacokinetic properties of a drug in vivo, such as its half-live, such drug can be conjugated with a carrier. If the drug is transiently bound to a carrier and/or a linker, such systems are commonly assigned as carrier-linked prodrugs. According to the definitions provided by IUPAC (as given under <http://www.chem.qmul.ac.uk/iupac.medchem>, accessed on Jul. 22, 2009), a carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

The linkers employed in such carrier-linked prodrugs may be transient, meaning that they are non-enzymatically hydrolytically degradable (cleavable) under physiological conditions (aqueous buffer at pH 7.4, 37° C.) with half-lives ranging from, for example, one hour to three months. Suitable carriers are polymers and can either be directly conjugated to the linker or via a non-cleavable spacer.

Transient polymer conjugation through traceless prodrug linkers combines the advantages of prolonged circulation times due to polymer attachment and the recovery of the original pharmacology of the native peptide after release from the polymer conjugate.

Using polymer-linker peptide conjugates, native unchanged peptide is slowly released after application to a patient, governed only by release kinetics of the linker and pharmacokinetics of the polymer carrier. Ideally, release kinetics would be independent from the presence of enzymes like proteases or esterases in body fluids to guarantee a consistent and homogenous release pattern.

The international patent application WO-A 2009/095479 refers to prodrugs comprising drug linker conjugates, where the linker is covalently attached via a cleavable bond to a biologically active moiety, such as exendin. The biologically active moiety is released from the prodrug upon cyclization-activation by cyclic imide formation. An exendin-prodrug is described in which the linker is based on L-alanine.

Still, there remains a need for development of long-acting exendin prodrugs with longer half-lives. Therefore, one object of the present invention is to provide exendin prodrugs with longer half-lives.

This is achieved by a prodrug or a pharmaceutically acceptable salt thereof comprising a covalent exendin prodrug of formula D-$L^1$, wherein
D represents an exendin moiety; and
$L^1$ is of formula (I),

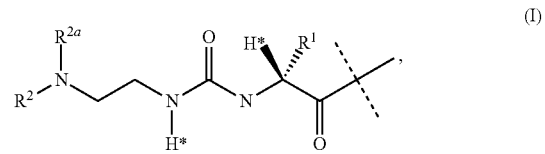

wherein the dashed line indicates attachment to one of the amino groups of the exendin by forming an amide bond;
$R^1$ is selected from $C_{1-4}$ alkyl, preferably $CH_3$;
$R^2$ and $R^{2a}$ are independently selected from the group consisting of H and $C_{1-4}$ alkyl;
wherein $L^1$ is substituted with one $L^2$-Z and optionally further substituted, provided that the hydrogens marked with the asterisks in formula (I) are not replaced by a substituent and wherein
$L^2$ is a single chemical bond or a spacer; and
Z is a hydrogel.

It was found that prodrug linkers based on the stereochemistry shown in formula (I), i.e. with an amino acid in its D-form, have an advantageous half-life compared to such prodrug linkers based on amino acids in their L-form. Further, such prodrugs may provide exendin release from a subcutaneous depot in structurally intact form over time periods of at least 2 days between administrations. As a further advantage, structural integrity of the released exendin may be provided by a well-hydrated polymer matrix minimizing intermolecular contact of exendin molecules and sustained release may be enabled by means of a self-cleaving prodrug linker between the exendin and the polymer matrix.

Thus it should be possible to administer exendin in form of a prodrug of the present invention less frequently than current long acting exendins. Further advantages should be a small peak to trough ratio, which greatly reduce the risk of adverse events, such as nausea and gastro intestinal complications. This may help patients to reduce the frequency of injections, while being able to maintain optimal control the plasma levels of exendin and consequently blood glucose.

The term "exendin", refers to an exendin agonist, an exendin analogue, an exendin derivative, a truncated exendin, a truncated exendin agonist, a truncated exendin derivative, a truncated exendin analogue, a extended exendin, a extended exendin agonist, a extended exendin derivative, a extended exendin analogue, GLP-1, a GLP-1 analogue, or a GLP-1 derivative, such as GLP-1 or GLP-1 analogue in amidated, truncated or extended form. Preferably, the exendin is an exendin or an exendin agonist of sequence ID 1 to ID 21 (see below), and more preferred it is exendin-3 having sequence ID 2 or exendin-4 having sequence ID 1.

The term "extended" refers to peptides or proteins which have additional amino acid residues at their N-terminal or C-terminal end or which have internal insertions. The term also refers to fusions of said peptides or proteins to other peptides or proteins, such as, for example, GST protein, FLAG peptide, hexa-his peptide, maltose-binding protein.

Examples of exendin agonists as used herein are exendin-3 or exendin-4 agonists including but not limited to:
(i) exendin-4 analogues and amidated exendin-4 analogues, in which sequences one or more amino acid residues have been replaced by different amino acid residues including N-terminal modifications;
(ii) truncated and extended forms of exendin-4 and truncated and extended forms that are amidated;
(iii) truncated and extended exendin-4 and truncated and extended forms that are amidated, in which sequences one or more amino acid residues have been replaced by different amino acid residues;
(iv) GLP-I and amidated GLP-1;
(v) GLP-1-analogues and amidated GLP-1 analogues, in which sequences one or more amino acid residues have been replaced by different amin acid residues including N-terminal modifications;
(vi) truncated and extended GLP-1 and truncated and extended forms that are amidated;
(vii) truncated GLP-1 and truncated forms that are amidated, in which sequences one or more amino acid residues have been replaced by different amino acid residues;
(viii) the already known substances AVE-0010/ZP-10/Lix-isenatide (Sanofi-Aventis Zealand Pharma; sequence ID 21), BAY-73-7977 (Bayer), TH-0318, BIM-51077 (Ipsen, Tejin, Roche), NN2211 (Novo Nordisk), LY315902.

Examples of exendin agonists as described above may be those in which an analogue of exendin-4 is selected from a group comprising $$H\text{-desPro}^{36}\text{-exendin-4-Lys}_6\text{-NH}_2,$$

$$H\text{-des}(Pro^{36,37})\text{-exendin-4-Lys}_4\text{-NH}_2$$
and $$H\text{-des}(Pro^{36,37})\text{-exendin-4-Lys}_5\text{-NH}_2,$$

or a pharmacologically tolerable salt thereof.

Further examples of exendin agonists as described above may be those in which an analogue of exendin-4 is selected from a group comprising $$desPro^{36}\ [Asp^{28}]exendin\text{-}4\ (1\text{-}39),$$

$$desPro^{36}\ [IsoAsp^{28}]exendin\text{-}4\ (1\text{-}39),$$

$$desPro^{36}\ [Met(O)^{14},\ Asp^{28}]exendin\text{-}4\ (1\text{-}39),$$

$$desPro^{36}\ [Met(O)^{14},\ IsoAsp^{28}]exendin\text{-}4\ (1\text{-}39),$$

$$desPro^{36}\ [Trp(O_2)^{25},\ Asp^{28}]exendin\text{-}2\ (1\text{-}39),$$

$$desPro^{36}\ [Trp(O_2)^{25},IsoAsp^{28}]exendin\text{-}2\ (1\text{-}39),$$

$$desPro^{36}\ [Met(O)^{14}Trp(O_2)^{25},\ Asp^{28}]exendin\text{-}4\ (1\text{-}39)$$
and $$desPro^{36}\ [Met(O)^{14}Trp(O_2)^{25},\ IsoAsp^{28}]exendin\text{-}4\ (1\text{-}39),$$

or a pharmacologically tolerable salt thereof.

Further examples of exendin agonists as described in the preceding paragraph may be those in which the peptide -Lys$_6$-NH$_2$ is attached to the C termini of the analogues of exendin-4.

Further examples of exendin agonists as described above may be those in which an analogue of exendin-4 is selected from a group comprising $$H\text{-}(Lys)_6\text{- des } Pro^{36}\ [Asp^{28}]exendin\text{-}4(1\text{-}39)\text{-}Lys_6\text{-}NH_2$$

$$des\ Asp^{28}Pro^{36},\ Pro^{37},\ Pro_{38}\ exendin\text{-}4(1\text{-}39)\ \text{-}NH_2,$$

$$H\text{-}(Lys)_6\text{-}des\ Pro^{36},\ Pro^{37},\ Pro^{38}\ [Asp^{28}]exendin\text{-}4(1\text{-}39)\ \text{-}NH_2,$$

$$H\text{-}Asn\text{-}(Glu)_5\ des\ Pro^{36},\ Pro^{37},\ Pro^{38}\ [Asp^{28}]exendin\text{-}4(1\text{-}39)\ \text{-}NH_2,$$

$$des\ Pro^{36},\ Pro^{37},\ Pro^{38}\ [Asp^{28}]exendin\text{-}4(1\text{-}39)\text{-}(Lys)_6\text{-}NH_2,$$

$$H\text{-}(Lys)_6\text{- des } Pro^{36},\ Pro^{37},\ Pro^{38}\ [Asp^{28}]exendin\text{-}4(1\text{-}39)\text{-}(Lys)_6\text{-}NH_2,$$

$$H\text{-}Asn\text{-}(Glu)_5\text{- des } Pro^{36},\ Pro^{37},\ Pro^{38}\ [Asp^{28}]exendin\text{-}4(1\text{-}39)\text{-}(Lys)_6\text{-}NH_2,$$

$$H\text{-}(Lys)_6\text{- des } Pro^{36}\ [Trp(O_2)^{25},\ Asp^{28}]exendin\text{-}4(1\text{-}39)\text{-}Lys_6\text{-}NH_2,$$

$$H\text{- des } Asp^{28}\ Pro^{36},\ Pro^{37},\ Pro^{38}\ [Trp(O_2)^{25}]exendin\text{-}4(1\text{-}39)\text{-}NH_2,$$

$$H\text{-}(Lys)_6\text{- des } Pro^{36},\ Pro^{37},\ Pro^{38}\ [Trp(O_2)^{25},\ Asp^{28}]exendin\text{-}4(1\text{-}39)\ \text{-}NH_2,$$

$$H\text{-}Asn\text{-}(Glu)_5\text{- des } Pro^{36},\ Pro^{37},\ Pro^{38}\ [Trp(O_2)^{25},\ Asp^{28}]exendin\text{-}4(1\text{-}39)\ \text{-}NH_2,$$

$$des\ Pro^{36},\ Pro^{37},\ Pro^{38}\ [Trp(O_2)^{25},\ Asp^{28}]exendin\text{-}4(1\text{-}39)\text{-}(Lys)_6\text{-}NH_2,$$

$$H\text{-}(Lys)_6\text{- des } Pro^{36},\ Pro^{37},\ Pro^{38}\ [Trp(O_2)^{25},\ Asp^{28}]exendin\text{-}4(1\text{-}39)\text{-}(Lys)_6\text{-}NH_2,$$

$$H\text{-}Asn\text{-}(Glu)_5\text{- des } Pro^{36},\ Pro^{37},\ Pro^{38}\ [Trp(O_2)^{25},\ Asp^{28}]exendin\text{-}4(1\text{-}39)\text{-}(Lys)_6\text{-}NH_2,$$

H-(Lys)$_6$- des Pro$^{36}$ [Met(O)$^{14}$, Asp$^{28}$]exendin-4(1-39)-Lys$_6$-NH$_2$, des Met(O)$^{14}$ Asp$^{28}$ Pro$^{36}$, Pro$^{37}$, Pro$^{38}$ exendin-4(1-39) -NH$_2$, H-(Lys)$_6$- des Pro$^{36}$, Pro$^{37}$, Pro$^{38}$ [Met(O)$^{14}$, Asp$^{28}$]exendin-4(1-39) -NH$_2$, H-Asn-(Glu)$_5$- des Pro$^{36}$, Pro$^{37}$, Pro$^{38}$ [Met(O)$^{14}$, Asp$^{28}$] exendin-4(1-39) -NH$_2$, des Pro$^{36}$, Pro$^{37}$, Pro$^{38}$ [Met(O)$^{14}$, Asp$^{28}$]exendin-4(1-39)-(Lys)$_6$-NH$_2$, H-(Lys)$_6$- des Pro$^{36}$, Pro$^{37}$, Pro$^{38}$ [Met(O)$^{14}$, Asp$^{28}$]exendin-4(1-39)-Lys$_6$-NH$_2$, H-Asn-(Glu)$_5$ des Pro$^{36}$, Pro$^{37}$, Pro$^{38}$ [Met(O)$^{14}$, Asp$^{28}$] exendin-4(1-39)-(Lys)$_6$-NH$_2$, H-(Lys)$_6$- des Pro$^{36}$ [Met(O)$^{14}$, Trp(O$_2$)$^{25}$, Asp$^{28}$]exendin-4(1-39)-Lys$_6$-NH$_2$, des Asp$^{28}$ Pro$^{36}$, Pro$^{37}$, Pro$^{38}$ [Met(O)$^{14}$, Trp(O$_2$)$^{25}$[exendin-4(1-39) -NH$_2$, H-(Lys)$_6$- des Pro$^{36}$, Pro$^{37}$, Pro$^{38}$ [Met(O)$^{14}$, Trp(O$_2$)$^{25}$, Asp$^{28}$]exendin-4(1-39) -NH$_2$, H-Asn-(Glu)$_5$- des Pro$^{36}$, Pro$^{37}$, Pro$^{38}$ [Met(O)$^{14}$, Asp$^{28}$] exendin-4(1-39) -NH$_2$, des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$, H-(Lys)$_6$- des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$, H-Asn-(Glu)$_5$- des Pro$^{36}$, Pro$^{37}$, Pro$^{38}$ [Met(O)$^{14}$, Trp(O$_2$)$^{25}$, Asp$^{28}$] exendin-4(1-39)-(Lys)$_6$-NH$_2$, or a pharmacologically tolerable salt thereof.

A further example of an exendin agonists as described above is Arg$^{34}$, Lys$^{26}$ (N$^\epsilon$($\gamma$-glutamyl(N$^\alpha$-hexadecanoyl))) GLP-1 (7-37) [liraglutide] or a pharmacologically tolerable salt thereof.

Exendin agonists mimic the activities of exendin-3 or exendin-4 by binding the receptor(s) at which exendin-3 or exendin-4 exerts its actions which are beneficial as insulinotropic and in the treatment of diabetes mellitus or by mimicking the effects of exendin on urine flow, slowing gastric emptying, inducing satiety, increasing urinary sodium excipient and/or decreasing urinary potassium concentration, by binding to the receptor(s) where exendin cause these effects.

In one embodiment, the exendin or exendin agonists with the Sequence ID NOs: 1-22 can be used to prepare the long acting polymeric conjugates of the invention:

```
Exendin-4
                                        [Seq ID No: 1]
HGEGTFTSDL SKQMEEEAVR LFIEWLKNGG PSSGAPPPS-NH2

Exendin-3
                                        [Seq ID No: 2]
HSDGTFTSDL SKQMEEEAVR LFIEWLKNGG PSSGAPPPS-NH2

[Seq ID No: 3]
HGEGTFTSDL SKQMEEEAVR LFIEWLKNGG P

[Seq ID No: 4]
HGEGTFTSDL SKQMEEEAVR LFIEWLKNGG Y

[Seq ID No: 5]
HGEGTFTSDL SKQMEEEAVR LFIEWLKNGG

[Seq ID No: 6]
HGEGTFTSDL SKQMEEEAVR LFIEWLKNGG-NH2

[Seq ID No: 7]
HGEGTFTSDL SKQMEEEAVR LFIEWLKN-NH2

[Seq ID No: 8]
HGEGTFTSDL SKQLEEEAVR LFIEFLKNGG PSSGAPPPS-NH-12

[Seq ID No: 9]
HGEGTFTSDL SKQLEEEAVR LFIEFLKN-NH2

[Seq ID No: 10]
HGEGTFTSDL SKQLEEEAVR LAIEFLKN-NH2

[Seq ID No: 11]
HGEGTFTSDL SKQLEEEAVR LFIEWLKNGG PSSGAPPPS-NH2

[Seq ID No: 12]
HGDGTFTSDL SKQMEEEAVR LFIEWLKNGG PSSGAPPPS-NH2

GLP-I (7-36) amide
                                        [Seq ID No 13]
HAEGTFTSDV SSYLEGQAAK EFIAWLVKGR-NH2

[Seq ID No 14]
HSEGTFTSDV SSYLEGQAAK EFIAWLVKGR-NH2

GLP-I (7-37)
                                        [Seq ID No 15]
HAEGTFTSDV SSYLEGQAAK EFIAWLVKGRG

[Seq ID No 16]
HAXaaGTFTSDV SSYLEGQAAK EFIAWLVKGR-NH2
Xaa = P, F, Y

[Seq ID No 17]
HXaaEGTFTSDV SSYLEGQAAK EFIAWLVKGR-NH2
Xaa = T, a-aminobutyric acid, D-Ala, V, Gly

[Seq ID No 18]
HaEGTFTSDV SSYLEGQAAK EFIAWLVKGG

[Seq ID No 19]
R-HAEGTFTSDV SSYLEGQAAK EFIAWLVKGR-NH2
R = acetyl, pyroglutamyl, N-2-hydroxybenzoyl,
N-trans-3-hexenoyl

[Seq ID No 20]
HXaaAEGTFTSDV SSYLEGQAAK EFIAWLVKGR-NH2
Xaa = 6-amino-hexanoyl.

[Seq ID No 21]
AVE-0010/ZP-10/Lixisenatide
HGEGTFTSDLSKQMEEEAVRLFIEWLKNGGPSSGAPPSKKKKKK-NH2

[Seq ID No 22]
Arg$^{34}$, Lys$^{26}$ (N$^\epsilon$($\gamma$-glutamyl(N$^\alpha$-hexadecanoyl)))
GLP-1 (7-37) [liraglutide]
HAEGTFTSDV SSYLEGQAAXaaEFIAWLVRGRG
Xaa = Lys(N$^\epsilon$($\gamma$-glutannyl(N$^\alpha$-hexadecanoyl)))
```

Preferably, the exendin is having the sequence ID 1, ID 13, ID 15, ID 21 or ID 22.

More preferably, the exendin is having the sequence ID 1, ID 13 or ID 21.

In one embodiment, the exendin is exendin-4 having sequence ID 1.

In another embodiment, the exendin is an analog having sequence ID 13.

In another embodiment, the exendin is an analog having sequence ID 21.

The exendin and exendin agonists derivatives of the invention will exert any and all activities exhibited by the parent non-modified molecule, but with a prolonged action.

Exendin bound to a non-biologically active linker is referred to as "exendin moiety".

"Non-biologically active linker" means a linker which does not show the pharmacological effects of the drug derived from the biologically active agent.

"Protective groups" refers to a moiety which temporarily protects a chemical functional group of a molecule during synthesis to obtain chemoselectivity in subsequent chemical reactions. Protective groups for alcohols are, for example, benzyl and trityl, protective groups for amines are, for example, tert-butyloxycarbonyl, 9-fluorenylmethyloxycarbonyl and benzyl and for thiols examples of protective groups are 2,4,6-trimethoxybenzyl, phenylthiomethyl, acetamidomethyl, p-methoxybenzyloxycarbonyl, tert-butylthio, triphenylmethyl, 3-nitro-2-pyridylthio, 4-methyltrityl.

"Protected functional groups" means a chemical functional group protected by a protective group.

"Acylating agent" means a moiety of the structure R—(C═O)—, providing the acyl group in an acylation reaction, optionally connected to a leaving group, such as acid chloride, N-hydroxy succinimide, pentafluorophenol and para-nitrophenol.

"Alkyl" means a straight-chain or branched carbon chain. Each hydrogen of an alkyl carbon may be replaced by a substituent.

"Aryl" refers to any substituent derived from a monocyclic or polycyclic or fused aromatic ring, including heterocyclic rings, e.g. phenyl, thiophene, indolyl, napthyl, pyridyl, which may optionally be further substituted.

"Acyl" means a chemical functional group of the structure R—(C═O)—, wherein R is an alkyl or aryl.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-4}$ alkyl carbon may be replaced by a substituent.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent.

Accordingly, "$C_{1-18}$ alkyl" means an alkyl chain having 1 to 18 carbon atoms and "$C_{8-18}$ alkyl" means an alkyl chain having 8 to 18 carbon atoms. Accordingly, "$C_{1-50}$ alkyl" means an alkyl chain having 1 to 50 carbon atoms.

"$C_{2-50}$ alkenyl" means a branched or unbranched alkenyl chain having 2 to 50 carbon atoms, e.g. if present at the end of a molecule: —CH═$CH_2$, —CH═CH—$CH_3$, —$CH_2$—CH═$CH_2$, —CH═CH—$CH_2$—$CH_3$, —CH═CH—CH═$CH_2$, or e.g. —CH═CH—, when two moieties of a molecule are linked by the alkenyl group. Each hydrogen of a $C_{2-50}$ alkenyl carbon may be replaced by a substituent as further specified. Accordingly, the term "alkenyl" relates to a carbon chain with at least one carbon-carbon double bond. Optionally, one or more triple bonds may occur.

"$C_{2-50}$ alkynyl" means a branched or unbranched alkynyl chain having 2 to 50 carbon atoms, e.g. if present at the end of a molecule: —C≡CH, —$CH_2$—C≡CH, $CH_2$—$CH_2$—C≡CH, $CH_2$—C≡C—$CH_3$, or e.g. —C≡C— when two moieties of a molecule are linked by the alkynyl group. Each hydrogen of a $C_{2-50}$ alkynyl carbon may be replaced by a substituent as further specified. Accordingly, the term "alkynyl" relates to a carbon chain with at least one carbon-carbon triple bond. Optionally, one or more double bonds may occur.

"$C_{3-7}$ cycloalkyl" or "$C_{3-7}$ cycloalkyl ring" means a cyclic alkyl chain having 3 to 7 carbon atoms, which may have carbon-carbon double bonds being at least partially saturated, e.g. cyclopropyl, cyclobutyl, cyclopentyl, cyclohexyl, cyclohexenyl, cycloheptyl. Each hydrogen of a cycloalkyl carbon may be replaced by a substituent. The term "$C_{3-7}$ cycloalkyl" or "$C_{3-7}$ cycloalkyl ring" also includes bridged bicycles like norbonane or norbonene. Accordingly, "$C_{3-6}$ cycloalkyl" means a cycloalkyl having 3 to 5 carbon atoms.

Accordingly, "$C_{3-10}$ cycloalkyl" means a cyclic alkyl having 3 to 10 carbon atoms, e.g. $C_{3-7}$ cycloalkyl; cyclopropyl, cyclobutyl, cyclopentyl, cyclohexyl, cyclohexenyl, cycloheptyl, cyclooctyl, cyclononyl, cyclodecyl. The term "$C_{3-10}$ cycloalkyl" also includes at least partially saturated carbomono- and -bicycles.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including ═N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine.

"9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including ═N(O)—) and wherein the ring is linked to the rest of the molecule via a carbon or nitrogen atom. Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane.

In case the exendin prodrugs comprising the compounds according to formula (I) contain one or more acidic or basic groups, the invention also comprises their corresponding pharmaceutically or toxicologically acceptable salts, in particular their pharmaceutically utilizable salts. Thus, the exendin prodrugs comprising the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Exendin prodrugs comprising the compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the exendin prodrugs comprising the compounds of the formula (I) simultaneously contain acidic and basic groups in the molecule, the invention also includes, in addition to the salt forms mentioned, inner salts or betaines (zwitterions). The respective salts according to exendin prodrugs comprising the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the exendin prodrugs comprising the compounds of the formula (I) which, owing to low physiological compatibility, are not directly suitable for use in pharmaceuticals but which can be used, for example, as intermediates for chemical reactions or for the preparation of pharmaceutically acceptable salts.

To enhance physicochemical or pharmacokinetic properties of a drug, such as exendin, in vivo, such drug can be conjugated with a carrier. If the drug is transiently bound to a carrier and/or a linker, such systems are commonly assigned as carrier-linked prodrugs. According to the definitions provided by IUPAC (as given under <http://www.chem.qmul.ac.uk/iupac.medchem>, accessed on Jul. 22, 2009), a carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

The linkers employed in such carrier-linked prodrugs are transient, meaning that they are non-enzymatically hydrolytically degradable (cleavable) under physiological conditions (aqueous buffer at pH 7.4, 37° C.) with half-lives ranging from, for example, one hour to three months.

The hydrogel carriers can either be directly conjugated to the linker L or via a spacer, preferably a non-cleavable spacer. The term "exendin hydrogel prodrug" refers to carrier-linked prodrugs of exendin, wherein the carrier is a hydrogel. The terms "hydrogel prodrug" and "hydrogel-linked prodrug" refer to prodrugs of biologically active agents transiently linked to a hydrogel and are used synonymously.

A "hydrogel" may be defined as a three-dimensional, hydrophilic or amphiphilic polymeric network capable of taking up large quantities of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water which allows them to swell in aqueous media. The chains of the network are connected in such a fashion that pores exist and that a substantial fraction of these pores are of dimensions between 1 nm and 1000 nm.

"Free form" of a drug refers to a drug, specifically to exendin, in its unmodified, pharmacologically active form, such as after being released from a polymer conjugate.

It is understood that the pharmacologically active form of exendin also includes oxidized and deamidated drug.

The terms "drug", "biologically active molecule", "biologically active moiety", "biologically active agent", "active agent", are used synonymously and refer to exendin, either in its bound or free form.

A "therapeutically effective amount" of exendin as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

"Stable" and "stability" means that within the indicated storage time the hydrogel conjugates remain conjugated and do not hydrolyze to a substantial extent and exhibit an acceptable impurity profile relating to exendin. To be considered stable, the composition contains less than 5% of the drug in its free form.

The term "pharmaceutically acceptable" means approved by a regulatory agency such as the EMEA (Europe) and/or the FDA (US) and/or any other national regulatory agency for use in animals, preferably in humans.

"Pharmaceutical composition" or "composition" means one or more active ingredients, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable excipient (pharmaceutically acceptable carrier).

"Dry composition" means that the exendin hydrogel prodrug composition is provided in a dry form in a container. Suitable methods for drying are spray-drying and lyophilization (freeze-drying). Such dry composition of exendin hydrogel prodrug has a residual water content of a maximum of 10%, preferably less than 5% and more preferably less than 2% (determined according to Karl Fischer). The preferred method of drying is lyophilization. "Lyophilized composition" means that the exendin hydrogel polymer prodrug composition was first frozen and subsequently subjected to water reduction by means of reduced pressure. This terminology does not exclude additional drying steps which occur in the manufacturing process prior to filling the composition into the final container.

"Lyophilization" (freeze-drying) is a dehydration process, characterized by freezing a composition and then reducing the surrounding pressure and, optionally, adding heat to allow the frozen water in the composition to sublime directly from the solid phase to gas. Typically, the sublimed water is collected by desublimation.

"Reconstitution" means the addition of a liquid to a dry composition to bring it into the form of a liquid or suspension composition. It is understood that the term "reconstitution" is not limited to the addition of water, but refers to the addition of any liquid, including for example buffers or other aqueous solutions.

"Reconstitution solution" refers to the liquid used to reconstitute the dry composition of an exendin hydrogel prodrug prior to administration to a patient in need thereof.

"Container" means any container in which the exendin hydrogel prodrug composition is comprised and can be stored until reconstitution.

"Buffer" or "buffering agent" refers to chemical compounds that maintain the pH in a desired range. Physiologically tolerated buffers are, for example, sodium phosphate, succinate, histidine, bicarbonate, citrate and acetate, pyruvate. Antacids such as $Mg(OH)_2$ or $ZnCO_3$ may be also used. Buffering capacity may be adjusted to match the conditions most sensitive to pH stability.

"Excipients" refers to compounds administered together with the therapeutic agent, for example, buffering agents, isotonicity modifiers, preservatives, stabilizers, anti-adsorption agents, oxidation protection agents, or other auxiliary agents. However, in some cases, one excipient may have dual or triple functions.

A "lyoprotectant" is a molecule which, when combined with a protein of interest, significantly prevents or reduces chemical and/or physical instability of the protein upon drying in general and especially during lyophilization and subsequent storage. Exemplary lyoprotectants include sugars, such as sucrose or trehalose; amino acids such as arginine, glycine, glutamate or histidine; methylamines such as betaine; lyotropic salts such as magnesium sulfate; polyols such as trihydric or higher sugar alcohols, e.g. glycerin, erythritol, glycerol, arabitol, xylitol, sorbitol, and mannitol; ethylene glycol; propylene glycol; polyethylene glycol; pluronics; hydroxyalkyl starches, e.g. hydroxyethyl starch (HES), and combinations thereof.

"Surfactant" refers to wetting agents that lower the surface tension of a liquid.

"Isotonicity modifiers" refer to compounds which minimize pain that can result from cell damage due to osmotic pressure differences at the injection depot.

The term "stabilizers" refers to compounds used to stabilize the polymer prodrug. Stabilisation is achieved by strengthening of the protein-stabilising forces, by destabilisation of the denatured state, or by direct binding of excipients to the protein.

"Anti-adsorption agents" refers to mainly ionic or non-ionic surfactants or other proteins or soluble polymers used to coat or adsorb competitively to the inner surface of the composition's container. Chosen concentration and type of excipient depends on the effect to be avoided but typically a monolayer of surfactant is formed at the interface just above the CMC value.

"Oxidation protection agents" refers to antioxidants such as ascorbic acid, ectoine, glutathione, methionine, monothioglycerol, morin, polyethylenimine (PEI), propyl gallate, vitamin E, chelating agents such aus citric acid, EDTA, hexaphosphate, thioglycolic acid.

"Antimicrobial" refers to a chemical substance that kills or inhibits the growth of microorganisms, such as bacteria, fungi, yeasts, protozoans and/or destroys viruses.

"Sealing a container" means that the container is closed in such way that it is airtight, allowing no gas exchange between the outside and the inside and keeping the content sterile.

The term "reagent" or "precursor" refers to an intermediate or starting material used in the assembly process leading to a prodrug of the present invention.

The term "chemical functional group" refers to carboxylic acid and activated derivatives, amino, maleimide, thiol and derivatives, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl and other alpha-beta unsaturated michael acceptors, arylating agents like aryl fluorides, hydroxylamine, disulfides like pyridyl disulfide, vinyl sulfone, vinyl ketone, diazoalkanes, diazoacetyl compounds, oxirane, and aziridine.

If a chemical functional group is coupled to another chemical functional group, the resulting chemical structure is referred to as "linkage". For example, the reaction of an amine group with a carboxyl group results in an amide linkage.

"Reactive functional groups" are chemical functional groups of the backbone moiety, which are connected to the hyperbranched moiety.

"Functional group" is the collective term used for "reactive functional group", "degradable interconnected functional group", or "conjugate functional group".

A "degradable interconnected functional group" is a linkage comprising a biodegradable bond which on one side is connected to a spacer moiety connected to a backbone moiety and on the other side is connected to the crosslinking moiety. The terms "degradable interconnected functional group", "biodegradable interconnected functional group", "interconnected biodegradable functional group" and "interconnected functional group" are used synonymously.

The terms "blocking group" or "capping group" are used synonymously and refer to moieties which are irreversibly connected to reactive functional groups to render them incapable of reacting with for example chemical functional groups.

The terms "protecting group" or "protective group" refers to a moiety which is reversibly connected to reactive functional groups to render them incapable of reacting with for example other chemical functional groups.

The term "interconnectable functional group" refers to chemical functional groups, which participate in a radical polymerization reaction and are part of the crosslinker reagent or the backbone reagent.

The term "polymerizable functional group" refers to chemical functional groups, which participate in a ligation-type polymerization reaction and are part of the crosslinker reagent and the backbone reagent.

A backbone moiety may comprise a spacer moiety which at one end is connected to the backbone moiety and on the other side to the crosslinking moiety.

The term "derivatives" refers to chemical functional groups suitably substituted with protecting and/or activation groups or to activated forms of a corresponding chemical functional group which are known to the person skilled in the art. For example, activated forms of carboxyl groups include but are not limited to active esters, such as succinimidyl ester, benzotriazyl ester, nitrophenyl ester, pentafluorophenyl ester, azabenzotriazyl ester, acyl halogenides, mixed or symmetrical anhydrides, acyl imidazole.

The term "non-enzymatically cleavable linker" refers to linkers that are hydrolytically degradable under physiological conditions without enzymatic activity.

"Non-biologically active linker" means a linker which does not show the pharmacological effects of the drug (D-H) derived from the biologically active moiety.

The terms "spacer", "spacer group", "spacer molecule", and "spacer moiety" are used interchangeably and if used to describe a moiety present in the hydrogel carrier of the invention, refer to any moiety suitable for connecting two moieties, such as $C_{1-50}$ alkyl, $C_{2-50}$ alkenyl or $C_{2-50}$ alkinyl, which fragment is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4 to 7 membered heterocyclyl, phenyl or naphthyl.

The terms "terminal", "terminus" or "distal end" refer to the position of a functional group or linkage within a molecule or moiety, whereby such functional group may be a chemical functional group and the linkage may be a degradable or permanent linkage, characterized by being located adjacent to or within a linkage between two moieties or at the end of an oligomeric or polymeric chain.

The phrases "in bound form" or "moiety" refer to substructures which are part of a larger molecule. The phrase "in bound form" is used to simplify reference to moieties by naming or listing reagents, starting materials or hypothetical starting materials well known in the art, and whereby "in bound form" means that for example one or more hydrogen radicals (—H), or one or more activating or protecting groups present in the reagents or starting materials are not present in the moiety.

It is understood that all reagents and moieties comprising polymeric moieties refer to macromolecular entities known to exhibit variabilities with respect to molecular weight, chain lengths or degree of polymerization, or the number of functional groups.

Structures shown for backbone reagents, backbone moieties, crosslinker reagents, and crosslinker moieties are thus only representative examples.

A reagent or moiety may be linear or branched. If the reagent or moiety has two terminal groups, it is referred to as a linear reagent or moiety. If the reagent or moiety has more than two terminal groups, it is considered to be a branched or multi-functional reagent or moiety.

The term "poly(ethylene glycol) based polymeric chain" or "PEG based chain" refers to an oligo- or polymeric molecular chain.

Preferably, such poly(ethylene glycol) based polymeric chain is connected to a branching core, it is a linear poly(ethylene glycol) chain, of which one terminus is connected to the branching core and the other to a hyperbranched dendritic moiety. It is understood that a PEG-based chain may be terminated or interrupted by alkyl or aryl groups optionally substituted with heteroatoms and chemical functional groups.

If the term "poly(ethylene glycol) based polymeric chain" is used in reference to a crosslinker reagent, it refers to a crosslinker moiety or chain comprising at least 20 weight % ethylene glycol moieties.

In the following sections the invention is described in further detail.

The present invention relates to a prodrug or a pharmaceutically acceptable salt thereof, comprising an exendin linker conjugate D-L$^1$, wherein
D represents an exendin moiety; and
L$^1$ is of formula (I),

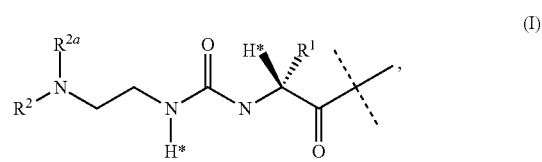

wherein the dashed line indicates the attachment to one of the amino groups of the exendin moiety by forming an amide bond;
R$^1$ is selected from $C_{1-4}$ alkyl, preferably CH$_3$;
R$^2$, R$^{2a}$ are independently selected from the group consisting of H and $C_{1-4}$ alkyl;
wherein L$^1$ is substituted with one L$^2$-Z and optionally further substituted, provided that the hydrogens marked with the asterisks in formula (I) are not replaced by a substituent and wherein
L$^2$ is a single chemical bond or a spacer; and
Z is a hydrogel.

Preferably, in formula (I) R$^2$ is replaced by L$^2$-Z.
Preferably, in formula (I) R$^1$ is CH$_2$-L$^2$-Z.
Preferably, L$^1$ is not further substituted.
Preferably, the exendin moiety is attached to L$^1$ through the N-terminal nitrogen or through a nitrogen of a lysine side chain of the exendin moiety. Most preferably, the exendin moiety is attached to L$^1$ through the N-terminal nitrogen.

Preferred prodrugs of the present invention comprise exendin linker conjugates D-L, wherein L is represented by formulae (Ia) or (Ib):

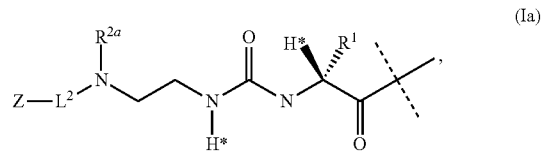

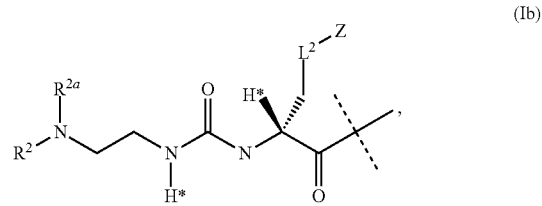

wherein D, R$^1$, R$^2$, R$^{2a}$, L$^2$, Z have the meaning and preferred meaning as indicated herein and wherein L is optionally further substituted, provided that the hydrogens marked with the asterisks in formula (Ia) or (Ib) are not replaced by a substituent, however preferably L is not further substituted (apart from the mandatory substituent L$^2$-Z already shown in (Ia) and (Ib)).

As shown in, e.g., formulae (Ia) or (Ib), one hydrogen of L$^1$ of formula (I) is replaced by the group L$^2$-Z.

In general, L$^2$ can be attached to L$^1$ in formula (I) at any position apart from the replacement of the hydrogens marked with the asterisks. Preferably, one of the hydrogens given by R$^1$, R$^2$, R$^{2a}$, directly or as hydrogen of the $C_{1-4}$ alkyl or further groups is replaced by L$^2$-Z.

Furthermore, $L^1$ of formula (I) may be optionally further substituted. In general, any substituent may be used as far as the cleavage is not affected. However it is preferred that $L^1$ is not further substituted.

Preferably, one or more further optional substituents are independently selected from the group consisting of halogen; CN; COOR$^9$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); SR$^9$; N(R$^9$R$^{9a}$); NO$_2$; OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)OR$^{9a}$; N(R$^9$)C(O)N(R$^{9a}$R$^{9b}$); OC(O)N(R$^9$R$^{9a}$); T; C$_{1-50}$ alkyl; C$_{2-50}$ alkenyl; or C$_{2-50}$ alkynyl, wherein T; C$_{1-50}$ alkyl; C$_{2-50}$ alkenyl; and C$_{2-50}$ alkynyl are optionally substituted with one or more R$^{10}$, which are the same or different and wherein C$_{1-50}$ alkyl; C$_{2-50}$ alkenyl; and C$_{2-50}$ alkynyl are optionally interrupted by one or more groups selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

R$^9$, R$^{9a}$, R$^{9b}$ are independently selected from the group consisting of H; Z; T; and C$_{1-50}$ alkyl; C$_{2-50}$ alkenyl; or C$_{2-50}$ alkynyl, wherein T; C$_{1-50}$ alkyl; C$_{2-50}$ alkenyl; and C$_{2-50}$ alkynyl are optionally substituted with one or more R$^{10}$, which are the same or different and wherein C$_{1-50}$ alkyl; C$_{2-50}$ alkenyl; and C$_{2-50}$ alkynyl are optionally interrupted by one or more groups selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

T is selected from the group consisting of phenyl; naphthyl; indenyl; indanyl; tetralinyl; C$_{3-10}$ cycloalkyl; 4 to 7 membered heterocyclyl; or 9 to 11 membered heterobicyclyl, wherein T is optionally substituted with one or more R$^{10}$, which are the same or different;

R$^{10}$ is halogen; CN; oxo (=O); COOR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$R$^{12}$; S(O)R$^{12}$; N(R$^{12}$)S(O)$_2$N(R$^{12a}$R$^{12b}$); SR$^{12}$; N(R$^{12}$R$^{12a}$); NO$_2$; OC(O)R$^{12}$; N(R$^{12}$)C(O)R$^{12a}$; N(R$^{12}$)S(O)$_2$R$^{12a}$; N(R$^{12}$)S(O)R$^{12a}$; N(R$^{12}$)C(O)OR$^{12a}$; N(R$^{12}$)C(O)N(R$^{12a}$R$^{12b}$); OC(O)N(R$^{12}$R$^{12a}$); or C$_{1-6}$ alkyl, wherein C$_{1-6}$ alkyl is optionally substituted with one or more halogen, which are the same or different;

R$^{11}$, R$^{11a}$, R$^{12}$, R$^{12a}$, R$^{12b}$ are independently selected from the group consisting of H; or C$_{1-6}$ alkyl, wherein C$_{1-6}$ alkyl is optionally substituted with one or more halogen, which are the same or different.

The term "interrupted" means that between two carbons a group is inserted or at the end of the carbon chain between the carbon and hydrogen.

$L^2$ is a single chemical bond or a spacer. In case $L^2$ is a spacer, it is preferably defined as the one or more optional substituents defined above, provided that $L^2$ is substituted with Z.

Accordingly, when $L^2$ is other than a single chemical bond, $L^2$-Z is COOR$^9$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); SR$^9$; N(R$^9$R$^{9a}$); OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)OR$^{9a}$; N(R$^9$)C(O)N(R$^{9a}$R$^{9b}$); OC(O)N(R$^9$R$^{9a}$); T; C$_{1-50}$ alkyl; C$_{2-50}$ alkenyl; or C$_{2-50}$ alkynyl, wherein T; C$_{1-50}$ alkyl; C$_{2-50}$ alkenyl; and C$_{2-50}$ alkynyl are optionally substituted with one or more R$^{10}$, which are the same or different and wherein C$_{1-50}$ alkyl; C$_{2-50}$ alkenyl; and C$_{2-50}$ alkynyl are optionally interrupted by one or more groups selected from the group consisting of -T-, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

R$^9$, R$^{9a}$, R$^{9b}$ are independently selected from the group consisting of H; Z; T; and C$_{1-50}$ alkyl; C$_{2-50}$ alkenyl; or C$_{2-50}$ alkynyl, wherein T; C$_{1-50}$ alkyl; C$_{2-50}$ alkenyl; and C$_{2-50}$ alkynyl are optionally substituted with one or more R$^{10}$, which are the same or different and wherein C$_{1-50}$ alkyl; C$_{2-50}$ alkenyl; and C$_{2-50}$ alkynyl are optionally interrupted by one or more groups selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

T is selected from the group consisting of phenyl; naphthyl; indenyl; indanyl; tetralinyl; C$_{3-10}$ cycloalkyl; 4 to 7 membered heterocyclyl; or 9 to 11 membered heterobicyclyl, wherein t is optionally substituted with one or more R$^{10}$, which are the same or different;

R$^{10}$ is Z; halogen; CN; oxo (=O); COOR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$R$^{12}$; S(O)R$^{12}$; N(R$^{12}$)S(O)$_2$N(R$^{12a}$R$^{12b}$); SR$^{12}$; N(R$^{12}$R$^{12a}$); NO$_2$; OC(O)R$^{12}$; N(R$^{12}$)C(O)R$^{12a}$; N(R$^{12}$)S(O)$_2$R$^{12a}$; N(R$^{12}$)S(O)R$^{12a}$; N(R$^{12}$)C(O)OR$^{12a}$; N(R$^{12}$)C(O)N(R$^{12a}$R$^{12b}$); OC(O)N(R$^{12}$R$^{12a}$); or C$_{1-6}$ alkyl, wherein C$_{1-6}$ alkyl is optionally substituted with one or more halogen, which are the same or different;

R$^{11}$, R$^{11a}$, R$^{12}$, R$^{12a}$, R$^{12b}$ are independently selected from the group consisting of H; Z; or C$_{1-6}$ alkyl, wherein C$_{1-6}$ alkyl is optionally substituted with one or more halogen, which are the same or different;

provided that only one of R$^9$, R$^{9a}$, R$^{9b}$, R$^{10}$, R$^{11}$, R$^{11a}$, R$^{12}$, R$^{12a}$, R$^{12b}$ is Z. More preferably, $L^2$ is a C$_{1-20}$ alkyl chain, which is optionally interrupted by one or more groups independently selected from —O—; and C(O)N(R$^{3aa}$); optionally substituted with one or more groups independently selected from OH; and C(O)N(R$^{3aa}$R$^{3aaa}$); and wherein R$^{3aa}$, R$^{3aaa}$ are independently selected from the group consisting of H; and C$_{1-4}$ alkyl.

Preferably, $L^2$ has a molecular weight in the range of from 14 g/mol to 750 g/mol.

Preferably, $L^2$ is attached to Z via a terminal group selected from

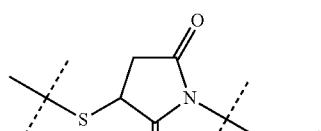; and

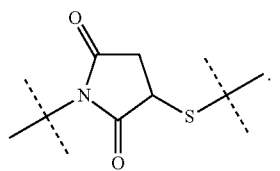

In case $L^2$ has such terminal group it is furthermore preferred that $L^2$ has a molecular weight in the range of from 14 g/mol to 500 g/mol calculated without such terminal group.

Preferably, the covalent attachment formed between the linker and Z is a permanent bond.

Preferably, the hydrogel Z is a biodegradable poly(ethylene glycol) (PEG) based water-insoluble hydrogel. The term "PEG based" as understood herein means that the mass proportion of PEG chains in the hydrogel is at least 10% by weight, preferably at least 25%, based on the total weight of the hydrogel. The remainder can be made up of other spacers and/or oligomers or polymers, such as oligo- or polylysines.

Moreover the term "water-insoluble" refers to a swellable three-dimensionally crosslinked molecular network forming the hydrogel. The hydrogel if suspended in a large surplus of water or aqueous buffer of physiological osmolality may take up a substantial amount of water, e.g. up to 10-fold on a weight per weight basis, and is therefore swellable but after removing excess water still retains the physical stability of a gel and a shape. Such shape may be of any geometry and it is understood that such an individual hydrogel object is to be considered as a single molecule consisting of components wherein each component is connected to each other component through chemical bonds.

According to this invention, the hydrogel may be composed of backbone moieties interconnected by hydrolytically degradable bonds. Preferably, the hydrogel is a PEG-based hydrogel comprised of backbone moieties.

Preferably, $L^2$ is connected to a backbone moiety.

Preferably, the backbone moiety has a molecular weight in the range of from 1 kDa to 20 kDa, more preferably from 1 kDa to 15 kDa and even more preferably from 1 kDa to 10 kDa. The backbone moieties are preferably also PEG-based comprising one or more PEG chains.

In a hydrogel carrying exendin-linker conjugates according to the invention, a backbone moiety is characterized by a number of functional groups, comprising interconnected biodegradable functional groups and hydrogel-connected drug-linker conjugates, and optionally capping groups. This means that a backbone moiety is characterized by a number of hydrogel-connected drug-linker conjugates; functional groups, comprising biodegradable interconnected functional groups; and optionally capping groups.

Preferably, the sum of interconnected biodegradable functional groups and drug-linker conjugates and capping groups is 16-128, preferred 20-100, more preferred 24-80 and most preferred 30-60.

Preferably, the sum of interconnected functional groups and hydrogel-connected drug-linker conjugates and capping groups of a backbone moiety is equally divided by the number of PEG-based polymeric chains extending from the branching core. For instance, if there are 32 interconnected functional groups and hydrogel-connected drug-linker conjugates and capping groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains. If the number of PEG-based polymeric chains extending from the branching core does not allow for an equal distribution, it is preferred that the deviation from the mean number of the sum of interconnected functional groups and hydrogel-connected drug-linker conjugates and capping groups per PEG-based polymeric chain is kept to a minimum.

In such carrier-linked prodrugs according to the invention, it is desirable that almost all drug release (>90%) has occurred before a significant amount of release of the backbone moieties (<10%) has taken place. This can be achieved by adjusting the carrier-linked prodrug's half-life versus the degradation kinetics of the hydrogel according to the invention.

Preferentially, a backbone moiety is characterized by having a branching core, from which at least three PEG-based polymeric chains extend. Accordingly, in a preferred aspect of the present invention the backbone reagent comprises a branching core, from which at least three PEG-based polymeric chains extend. Such branching cores may be comprised of poly- or oligoalcohols in bound form, preferably pentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, or branching cores may be comprised of poly- or oligoamines such as ornithine, diaminobutyric acid, trilysine, tetralysine, pentalysine, hexalysine, heptalysine, octalysine, nonalysine, decalysine, undecalysine, dodecalysine, tridecalysine, tetradecalysine, pentadecalysine or oligolysines, polyethyleneimines, polyvinylamines in bound form.

Preferably, the branching core extends three to sixteen PEG-based polymeric chains, more preferably four to eight. Preferred branching cores may be comprised of pentaerythritol, ornithine, diaminobutyric acid, trilysine, tetralysine, pentalysine, hexalysine, heptalysine or oligolysine, low-molecular weight PEI, hexaglycerine, tripentaerythritol in bound form. Preferably, the branching core extends three to sixteen PEG-based polymeric chains, more preferably four to eight. Preferably, a PEG-based polymeric chain is a linear poly(ethylene glycol) chain, of which one end is connected to the branching core and the other to a hyperbranched dendritic moiety. It is understood that a polymeric PEG-based chain may be terminated or interrupted by alkyl or aryl groups optionally substituted with heteroatoms and chemical functional groups.

Preferably, a PEG-based polymeric chain is a suitably substituted poly(ethylene glycol) derivative (PEG based).

Preferred structures for corresponding PEG-based polymeric chains extending from a branching core contained in a backbone moiety are multi-arm PEG derivatives as, for instance, detailed in the products list of JenKem Technology, USA (accessed by download from www.jenkemusa.com on Jul. 28, 2009), 4ARM-PEG Derivatives (pentaerythritol core), 8ARM-PEG Derivatives (hexaglycerin core) and 8ARM-PEG Derivatives (tripentaerythritol core). Most preferred are 4arm PEG Amine (pentaerythritol core) and 4arm PEG Carboxyl (pentaerythritol core), 8arm PEG Amine (hexaglycerin core), 8arm PEG Carboxyl (hexaglycerin core), 8arm PEG Amine (tripentaerythritol core) and 8arm PEG Carboxyl (tripentaerythritol core). Preferred molecular weights for such multi-arm PEG-derivatives in a backbone moiety are 1 kDa to 20 kDa, more preferably 1 kDa to 15 kDa and even more preferably 1 kDa to 10 kDa.

It is understood that the terminal amine groups of the above mentioned multi-arm molecules are present in bound form in the backbone moiety to provide further interconnected functional groups and reactive functional groups of a backbone moiety.

It is preferred that the sum of interconnected functional groups and reactive functional groups of a backbone moiety is equally divided by the number of PEG-based polymeric chains extending from the branching core. If the number of PEG-based polymeric chains extending from the branching core does not allow for an equal distribution, it is preferred that the deviation from the mean number of the sum of interconnected and reactive functional groups per PEG-based polymeric chain is kept to a minimum.

More preferably, the sum of interconnected and reactive functional groups of a backbone moiety is equally divided by the number of PEG-based polymeric chains extending from the branching core. For instance, if there are 32 interconnected functional groups and reactive functional groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains.

Such additional functional groups may be provided by dendritic moieties. Preferably, each dendritic moiety has a molecular weight in the range of from 0.4 kDa to 4 kDa, more preferably 0.4 kDa to 2 kDa. Preferably, each dendritic moiety has at least 3 branchings and at least 4 reactive functional groups, and at most 63 branchings and 64 reactive functional groups, preferred at least 7 branchings and at least 8 reactive functional groups and at most 31 branchings and 32 reactive functional groups.

Examples for such dendritic moieties are comprised of trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine in bound form. Examples for such preferred dendritic moieties are comprised of trilysine, tetralysine, pentalysine, hexalysine, heptalysine in bound form, most preferred trilysine, pentalysine or heptalysine, ornithine, diaminobutyric acid in bound form.

Most preferably, the hydrogel carrier of the present invention is characterized in that the backbone moiety has a quarternary carbon of formula $C(A-Hyp)_4$, wherein each A is independently a poly(ethylene glycol) based polymeric chain terminally attached to the quarternary carbon by a permanent covalent bond and the distal end of the PEG-based polymeric chain is covalently bound to a dendritic moiety Hyp, each dendritic moiety Hyp having at least four functional groups representing the interconnected functional groups and reactive functional groups.

Preferably, each A is independently selected from the formula $—(CH_2)_{n1}(OCH_2CH_2)_nX—$, wherein n1 is 1 or 2; n is an integer in the range of from 5 to 50; and X is a chemical functional group covalently linking A and Hyp.

Preferably, A and Hyp are covalently linked by an amide linkage.

Preferably, the dendritic moiety Hyp is a hyperbranched polypeptide. Preferably, the hyperbranched polypeptide comprises lysine in bound form. Preferably, each dendritic moiety Hyp has a molecular weight in the range of from 0.4 kDa to 4 kDa. It is understood that a backbone moiety $C(A-Hyp)_4$ can consist of the same or different dendritic moieties Hyp and that each Hyp can be chosen independently. Each moiety Hyp consists of between 5 and 32 lysines, preferably of at least 7 lysines, i.e. each moiety Hyp is comprised of between 5 and 32 lysines in bound form, preferably of at least 7 lysines in bound form. Most preferably, Hyp is comprised of heptalysinyl.

The reaction of polymerizable functional groups a backbone reagent, more specifically of Hyp with the polymerizable functional groups of poly(ethylene glycol) based crosslinker reagents results in a permanent amide bond.

Preferably, $C(A-Hyp)_4$ has a molecular weight in the range of from 1 kDa to 20 kDa, more preferably 1 kDa to 15 kDa and even more preferably 1 kDa to 10 kDa.

One preferred backbone moiety is shown below, dashed lines indicate interconnecting biodegradable linkages to crosslinker moieties and n is an integer of from 5 to 50:

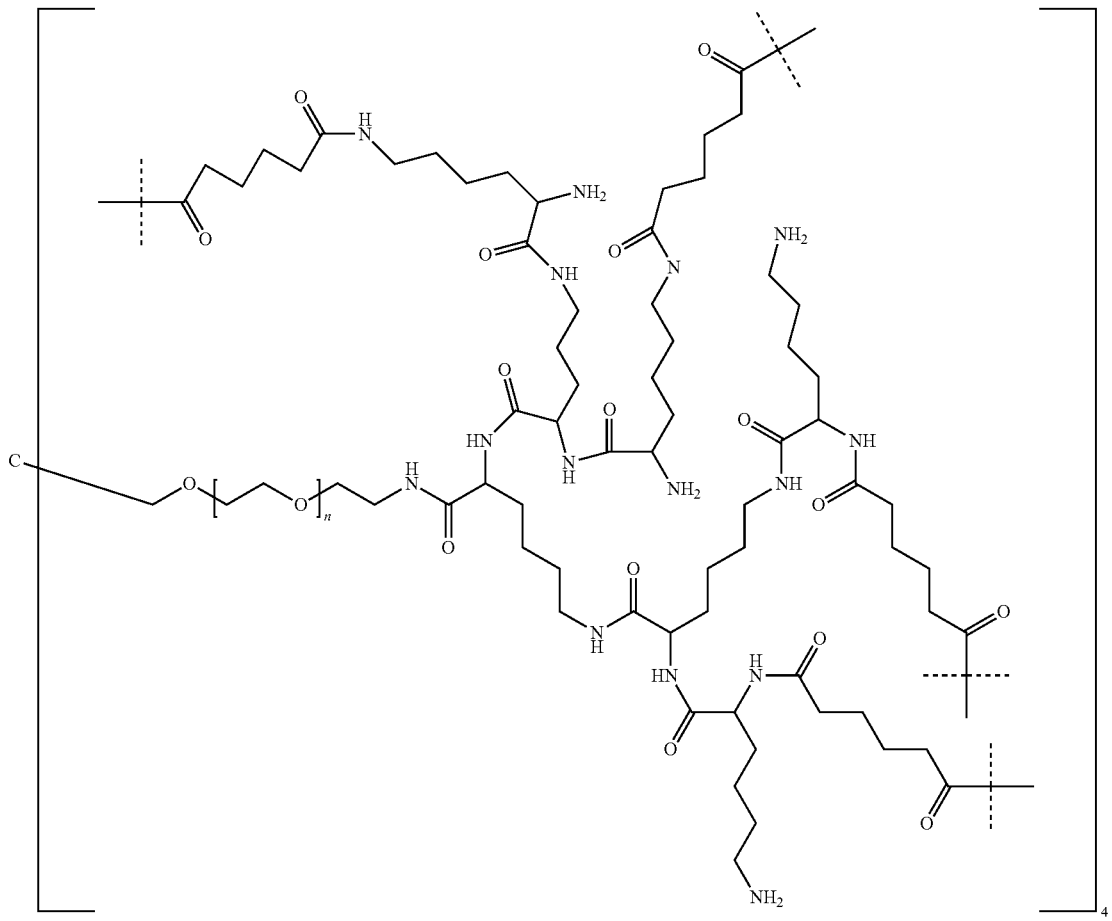

Biodegradability of the hydrogels according to the present invention is achieved by introduction of hydrolytically degradable bonds.

The terms "hydrolytically degradable", "biodegradable" or "hydrolytically cleavable", "auto-cleavable", or "self-cleavage", "self-cleavable", "transient" or "temporary" refers within the context of the present invention to bonds and linkages which are non-enzymatically hydrolytically degradable or cleavable under physiological conditions (aqueous buffer at pH 7.4, 37° C.) with half-lives ranging from one hour to three months, including, but are not limited to, aconityls, acetals, amides, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like.

If present in a hydrogel according to the invention as degradable interconnected functional group, preferred biodegradable linkages are carboxylic esters, carbonates, phosphoesters and sulfonic acid esters and most preferred are carboxylic esters or carbonates.

Permanent linkages are non-enzymatically hydrolytically degradable under physiological conditions (aqueous buffer at pH 7.4, 37° C.) with half-lives of six months or longer, such as, for example, amides.

To introduce the hydrolytically cleavable bonds into the hydrogel carrier of the invention, the backbone moieties can be directly linked to each other by means of biodegradable bonds.

In one embodiment, the backbone moieties of the biodegradable hydrogel carrier may be linked together directly, i.e. without crosslinker moieties. The hyperbranched dendritic moieties of two backbone moieties of such biodegradable hydrogel may either be directly linked through an interconnected functional group that connects the two hyperbranched dendritic moieties. Alternatively, two hyperbranched dendritic moieties of two different backbone moieties may be interconnected through two spacer moieties connected to a backbone moiety and on the other side connected to a crosslinking moiety separated by an interconnected functional groups.

Alternatively, backbone moieties may be linked together through crosslinker moieties, each crosslinker moiety is terminated by at least two of the hydrolytically degradable bonds. In addition to the terminating degradable bonds, the crosslinker moieties may contain further biodegradable bonds. Thus, each end of the crosslinker moiety linked to a backbone moiety comprises a hydrolytically degradable bond, and additional biodegradable bonds may optionally be present in the crosslinker moiety.

Preferably, the biodegradable hydrogel carrier is composed of backbone moieties interconnected by hydrolytically degradable bonds and the backbone moieties are linked together through crosslinker moieties.

The biodegradable hydrogel carrier may contain one or more different types of crosslinker moieties, preferably one. The crosslinker moiety may be a linear or branched molecule and preferably is a linear molecule. In a preferred embodiment of the invention, the crosslinker moiety is connected to backbone moieties by at least two biodegradable bonds.

Preferably, crosslinker moieties have a molecular weight in the range of from 60 Da to 5 kDa, more preferably, from 0.5 kDa to 5 kDa, even more preferably from 1 kDa to 4 kDa, even more preferably from 1 kDa to 3 kDa. In one embodiment, a crosslinker moiety consists of a polymer.

In addition to oligomeric or polymeric crosslinking moieties, low-molecular weight crosslinking moieties may be used, especially when hydrophilic high-molecular weight backbone moieties are used for the formation of a biodegradable hydrogel according to the invention.

Preferably, the poly(ethylene glycol) based crosslinker moieties are hydrocarbon chains comprising ethylene glycol units, optionally comprising further chemical functional groups, wherein the poly(ethylene glycol) based crosslinker moieties comprise at least each m ethylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

If used in reference to a crosslinker moiety or a PEG-based polymeric chain connected to a branching core, the term "PEG-based" refers to a crosslinker moiety or PEG-based polymeric chain comprising at least 20 weight % ethylene glycol moieties.

In one embodiment, monomers constituting the polymeric crosslinker moieties are connected by biodegradable bonds. Such polymeric crosslinker moieties may contain up to 100 biodegradable bonds or more, depending on the molecular weight of the crosslinker moiety and the molecular weight of the monomer units. Examples for such crosslinker moieties are poly(lactic acid) or poly(glycolic acid) based polymers. It is understood that such poly(lactic acid) or poly(glycolic acid) chain may be terminated or interrupted by alkyl or aryl groups and that they may optionally be substituted with heteroatoms and chemical functional groups.

Preferably, the crosslinker moieties are PEG based, preferably represented by only one PEG based molecular chain. Preferably, the poly(ethylene glycol) based crosslinker moieties are hydrocarbon chains comprising ethylene glycol units, optionally comprising further chemical functional groups, wherein the poly(ethylene glycol) based crosslinker moieties comprise at least each m ethylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

In a preferred embodiment of the present invention the crosslinker moiety consists of PEG, which is symmetrically connected through ester bonds to two alpha, omega-aliphatic dicarboxylic spacers provided by backbone moieties connected to the hyperbranched dendritic moiety through permanent amide bonds.

The dicarboxylic acids of the spacer moieties connected to a backbone moiety and on the other side is connected to a crosslinking moiety consist of 3 to 12 carbon atoms, most preferably between 5 and 8 carbon atoms and may be substituted at one or more carbon atom. Preferred substituents are alkyl groups, hydroxyl groups or amido groups or substituted amino groups. One or more of the aliphatic dicarboxylic acid's methylene groups may optionally be substituted by O or NH or alkyl-substituted N. Preferred alkyl is linear or branched alkyl with 1 to 6 carbon atoms.

Preferably, there is a permanent amide bond between the hyperbranched dendritic moiety and the spacer moiety connected to a backbone moiety and on the other side is connected to a crosslinking moiety.

One preferred crosslinker moiety is shown below; dashed lines indicate interconnecting biodegradable linkages to backbone moieties:

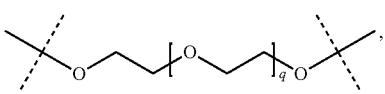

wherein q is an integer of from 5 to 50.

Preferably, the hydrogel carrier is composed of backbone moieties interconnected by hydrolytically degradable bonds.

More preferably, the backbone moieties comprise a branching core of the following formula:

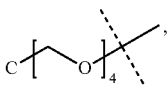

wherein the dashed line indicates attachment to the remainder of the backbone moiety.

More preferably, the backbone moieties comprise a structure of the following formula:

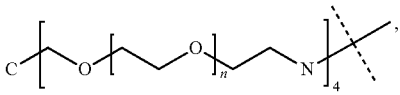

wherein n is an integer of from 5 to 50 and the dashed line indicates attachment to the remainder of the backbone moiety.

Preferably, backbone moiety comprises a hyperbranched moiety Hyp.

More preferably, the backbone moiety comprises a hyperbranched moiety Hyp of the following formula:

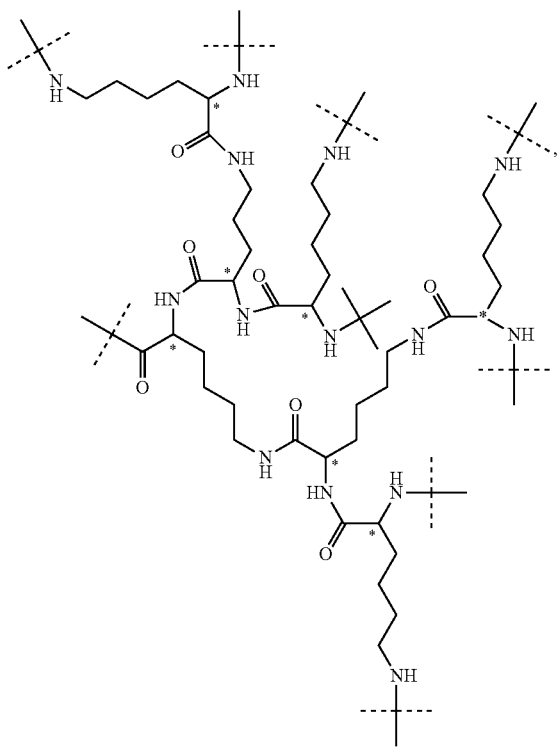

wherein the dashed lines indicate attachment to the rest of the molecule and carbon atoms marked with asterisks indicate S-configuration.

Preferably, the backbone moieties are attached to at least one spacer of the following formula:

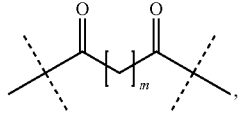

wherein one of the dashed lines indicates attachment to the hyperbranched moiety Hyp and the second dashed line indicates attachment to the rest of the molecule; and wherein m is an integer of from 2 to 4.

Preferably, the backbone moieties are linked together through crosslinker moieties having the following structure

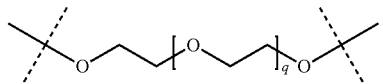

wherein
q is an integer from 3 to 100, preferably from 5 to 50.

In hydrogel prodrugs of the invention, the hydrolysis rate of the biodegradable bonds between backbone moieties and crosslinker moieties is influenced or determined by the number and type of connected atoms adjacent to the PEG-ester carboxy group. For instance, by selecting from succinic, adipic or glutaric acid for PEG ester formation it is possible to vary the degradation half-lives of the biodegradable hydrogel carrier according to the invention.

Preferably, $L^2$ is attached to Z through a thiosuccinimide group which in turn is attached to the hydrogel's backbone moiety through a spacer, such as an oligoethylene glycol chain. Preferably, the linkage of this spacer chain to the backbone moiety is a permanent bond, preferably an amide bond.

Biodegradability of the hydrogels according to the present invention is achieved by introduction of hydrolytically degradable bonds.

For interconnected functional groups, the term "hydrolytically degradable" refers within the context of the present invention to linkages which are non-enzymatically hydrolytically degradable under physiological conditions (aqueous buffer at pH 7.4, 37° C.) with half-lives ranging from one hour to three months, include, but are not limited to, aconityls, acetals, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are carboxylic esters, carbonates, phosphoesters and sulfonic acid esters and most preferred are carboxylic esters or carbonates. It is understood that for in vitro studies accelerated conditions like, for example, pH 9, 37° C., aqueous buffer, may be used for practical purposes.

Permanent linkages are non-enzymatically hydrolytically degradable under physiological conditions (aqueous buffer at pH 7.4, 37° C.) with half-lives of six months or longer, such as, for example, amides.

The degradation of the biodegradable hydrogel carrier according to the invention is a multi-step reaction where a multitude of degradable bonds is cleaved resulting in degradation products which may be water-soluble or water-insoluble. However, water-insoluble degradation products may further comprise degradable bonds so that they can be cleaved in that water-soluble degradation products are obtained.

These water-soluble degradation products may comprise one or more backbone moieties. It is understood that released backbone moieties may, for instance, be permanently conjugated to spacer or blocking or linker groups or affinity groups and/or prodrug linker degradation products and that also water-soluble degradation products may comprise degradable bonds.

The structures of the branching core, PEG-based polymeric chains, hyperbranched dendritic moieties and moieties attached to the hyperbranched dendritic moieties can be inferred from the corresponding descriptions provided in the sections covering the hydrogel carriers of the present invention. It is understood that the structure of a degradant depends on the type of hydrogel according to the invention undergoing degradation.

The total amount of backbone moieties can be measured in solution after complete degradation of the hydrogel according to the invention, and during degradation, fractions of soluble backbone degradation products can be separated from the insoluble hydrogel according to the invention and can be quantified without interference from other soluble degradation products released from the hydrogel according to the invention. A hydrogel object according to the invention may be separated from excess water of buffer of physiological osmolality by sedimentation or centrifugation.

Centrifugation may be performed in such way that the supernatant provides for at least 10% of the volume of the swollen hydrogel according to the invention. Soluble hydrogel degradation products remain in the aqueous supernatant after such sedimentation or centrifugation step, and water-soluble degradation products comprising one or more backbone moieties are detectable by subjecting aliquots of such supernatant to suitable separation and/or analytical methods.

Preferably, water-soluble degradation products may be separated from water-insoluble degradation products by filtration through 0.45 µm filters, after which the water-soluble degradation products can be found in the flow-through. Water-soluble degradation products may also be separated from water-insoluble degradation products by a combination of a centrifugation and a filtration step.

For instance the backbone moieties may carry groups that exhibit UV absorption at wavelengths where other degradation products do not exhibit UV absorption. Such selectively UV-absorbing groups may be structural components of the backbone moiety such as amide bonds or may be introduced into the backbone by attachment to its reactive functional groups by means of aromatic ring systems such as indoyl groups.

In such hydrogel-linked exendin prodrugs according to the invention, it is desirable that almost all exendin release (>90%) has occurred before a significant amount of release of the backbone degradation products (<10%) has taken place. This can be achieved by adjusting the hydrogel-linked exendin prodrug's half-life versus the hydrogel degradation kinetics.

Preferably, the exendin prodrug D-L has a structure, where L is represented by formula (II)

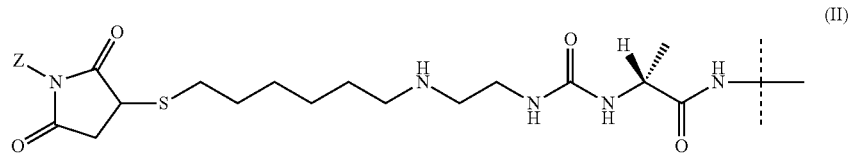

(II)

wherein the dashed line indicates attachment to a nitrogen, preferably the N-terminal nitrogen, of the exendin by forming an amide bond and Z is a hydrogel;

Preferably, the hydrogel in formula (II) is a biodegradable poly(ethylene glycol) (PEG) based water-insoluble hydrogel.

Preferably, the hydrogel in formula (II) is composed of backbone moieties interconnected by hydrolytically degradable bonds.

More preferably, the backbone moieties comprise a branching core of the following formula:

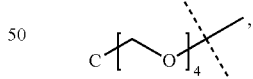

wherein the dashed line indicates attachment to the remainder of the backbone moiety.

More preferably, the backbone moieties comprise a structure of the following formula:

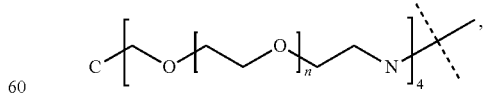

wherein n is an integer of from 5 to 50 and the dashed line indicates attachment to the rest of the molecule.

Preferably, backbone moiety comprises a hyperbranched moiety Hyp.

More preferably, the backbone moiety comprises a hyperbranched moiety Hyp of the following formula:

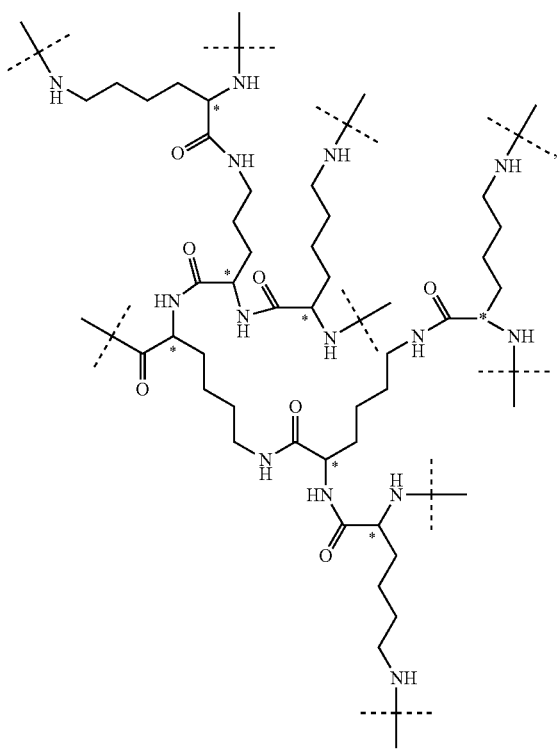

wherein the dashed lines indicate attachment to the rest of the molecule and carbon atoms marked with asterisks indicate S-configuration.

Preferably, the backbone moieties are attached to at least one spacer of the following formula:

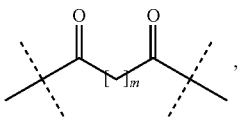

wherein one of the dashed lines indicates attachment to the hyperbranched moiety Hyp and the second dashed line indicates attachment to the rest of the molecule; and wherein m is an integer of from 2 to 4.

Preferably, the backbone moieties are attached to at least one spacer of the following formula:

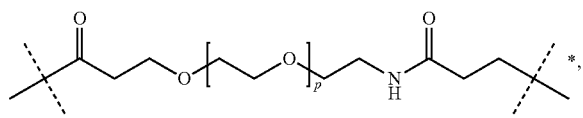

wherein the dashed line marked with the asterisk indicates the bond between the hydrogel and the N of the thiosuccinimide group;
wherein the other dashed line indicates attachment to Hyp; and wherein p is an integer of from 0 to 10.

Preferably, the backbone moieties are linked together through crosslinker moieties having the following structure

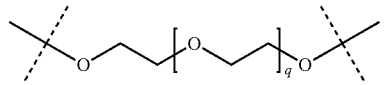

wherein q is an integer from 3 to 100.

The hydrolysis rate of the biodegradable bonds between backbone and crosslinker moieties is determined by the number and type of connected atoms adjacent to the PEG-ester carboxy group. For instance by selecting from succinic, adipic or glutaric acid for PEG ester formation it is possible to vary the degradation half-lives of the crosslinker.

The hydrogel-linked exendin prodrug of the present invention can be prepared starting from the hydrogel of the present invention by convenient methods known in the art. It is clear to a practitioner in the art that several routes exist. For example the prodrug linker mentioned above to which the biologically active moiety is covalently attached can be reacted with the reactive functional groups of the hydrogel of the present invention with or with already bearing the active moiety in part or as whole.

In a preferred method of preparation, the hydrogel is generated through chemical ligation reactions. The hydrogel may be formed from two macromolecular educts with complementary functionalities which undergo a reaction such as a condensation or addition. One of these starting materials is a crosslinker reagent with at least two identical functional groups and the other starting material is a homomultifunctional backbone reagent. Suitable functional groups present on the crosslinker reagent include terminal amino, carboxylic acid and derivatives, maleimide and other alpha,beta unsaturated Michael acceptors like vinylsulfone, thiol, hydroxyl groups. Suitable functional groups present in the backbone reagent include but are not limited to amino, carboxylic acid and derivatives, maleimide and other alpha,beta unsaturated Michael acceptors like vinylsulfone, thiol, hydroxyl groups.

If the crosslinker reagent reactive functional groups are used substoichiometrically with respect to backbone reactive functional groups, the resulting hydrogel will be a reactive hydrogel with free reactive functional groups attached to the backbone structure.

Optionally, the prodrug linker may be first conjugated to exendin and the resulting exendin-prodrug linker conjugate may then react with the hydrogel's reactive functional groups. Alternatively, after activation of one of the functional groups of the prodrug linker, the linker-hydrogel conjugate may be contacted with exendin in the second reaction step and excess exendin may be removed by filtration after conjugation of the exendin to the hydrogel-bound prodrug linker.

A preferred process for the preparation of a prodrug according to the present invention is as follows:

A preferred starting material for the backbone reagent synthesis is a 4-arm PEG tetra amine or 8-arm PEG octa amine, with the PEG reagent having a molecular weight ranging from 2000 to 10000 Dalton, most preferably from 2000 to 5000 Da. To such multi-arm PEG-derivatives, lysine residues are coupled sequentially to form the hyperbranched backbone reagent. It is understood that the lysines can be partially or fully protected by protective groups during the coupling steps and that also the final backbone reagent may contain protective groups. A preferred building block is bis-boc lysine. Alternatively, instead of sequential additions of lysine residues, a dendritic poly-lysine moiety may be assembled first and subsequently coupled to the 4-arm PEG tetra amine or 8-arm PEG octa amine. It is desirable to obtain backbone reagent carrying 32 amino groups, consequently seven lysines would be attached to each arm of a 4-arm PEG, or five lysines would be attached to each arm of a 8-arm PEG. In another embodiment, the multi-arm PEG derivative is a tetra- or octa carboxy PEG. In this case, the dendritic moieties may be generated from glutaric or aspartic acid, and the resulting backbone reagent would carry 32 carboxy groups. It is understood that all or a fraction of the backbone reagent's functional groups may be present in a free form, as salts or conjugated to protecting groups. It is understood that due to practical reasons the backbone reagent's number of lysines per PEG-arm will be between six and seven, more preferably approximately seven.

A preferred backbone reagent is shown below:

In an alternative embodiment, the backbone reagent carries carboxy groups and the corresponding crosslinker reagent would be selected from ester-containing amino-terminated PEG-chains.

Backbone reagent and crosslinker reagent may be polymerized to form the hydrogel according to the invention using inverse emulsion polymerization. After selecting the desired stoichiometry between backbone and crosslinker functional groups, backbone and crosslinker are dissolved in DMSO and a suitable emulgator with an appropriately selected HLB value, preferably Arlacel P135, is employed to form an inverse emulsion using a mechanical stirrer and controlling the stirring speed. Polymerization is initiated by the addition

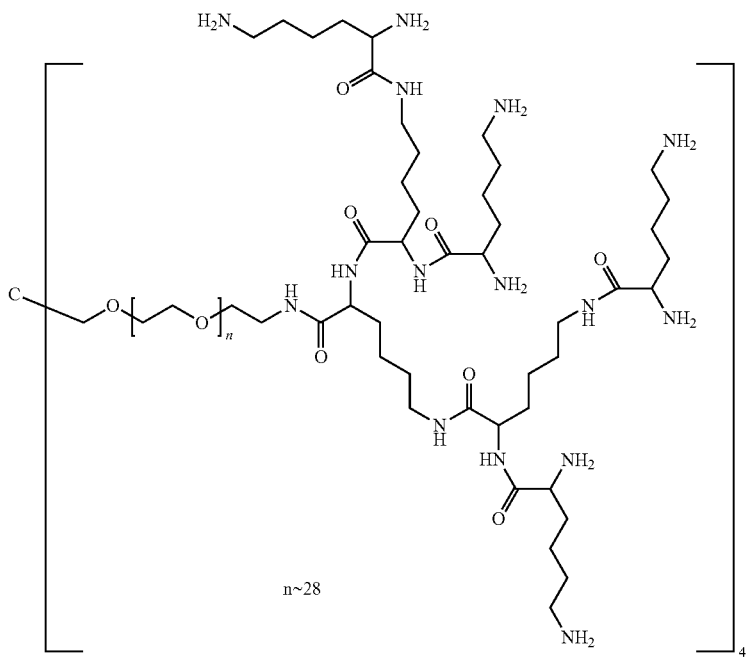

Synthesis of the crosslinker reagent starts from a linear PEG chain with a molecular weight ranging from 0.2 to 5 kDa, more preferably from 0.6 to 2 kDa, which is esterified with a half ester of a dicarboxylic acid, such as adipic acid or glutaric acid. Preferred protecting group for half ester formation is the benzylic group. The resulting bis dicarboxylic acid PEG half esters are converted into more reactive carboxy compounds such as acyl chlorides or active esters, e.g. pentafluorophenyl or N-hydroxysuccinimide esters, most preferred N-hydroxysuccinimde esters, of which preferred selected structure is shown below.

of a suitable base, preferably by N,N,N',N'-tetramethylethylene diamine. After stirring for an appropriate amount of time, the reaction is quenched by the addition of an acid, such as acetic acid and water. The beads are harvested, washed, and fractionated according to particle size by mechanical sieving. Optionally, protecting groups may be removed at this stage.

Further, such hydrogel according to the invention may be functionalized with a spacer carrying a different reactive functional group than provided by the hydrogel. For instance maleimide reactive functional groups may be introduced into the hydrogel by coupling a suitable heterobifunctional spacer

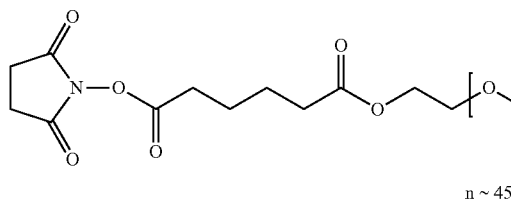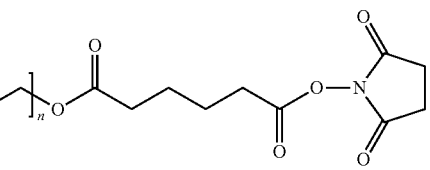

n ~ 45

Alternatively, the bis dicarboxylic acid PEG half esters may be activated in the presence of a coupling agent such as DCC or HOBt or PyBOP.

such as Mal-PEG6-NHS to the hydrogel. Such functionalized hydrogel can be further conjugated to exendin-linker reagents, carrying a reactive thiol group on the linker moiety to form hydrogel-linked exendin prodrugs according to the present invention.

After loading the exendin-linker conjugate to the functionalized maleimido group-containing hydrogel, all remaining functional groups are capped with a suitable blocking reagent, such as mercaptoethanol, to prevent undesired side-reactions.

In another preferred embodiment of the invention, an exendin-linker conjugate carrying a free thiol is connected to the linker moiety, is reacted with a maleimide-functionalized hydrogel at temperatures between room temperature and 4° C., more preferred at room temperature, in a buffered aqueous solution of pH 5.5-8, preferably pH 6.5-7.5. Subsequently, the resulting drug-linker-hydrogel conjugate is treated with a low molecular weight compound comprising a thiol group, preferably with a thiol-containing compound of 34-500 Da, most preferably with mercaptoethanol at temperatures between room temperature and 4° C., more preferred at room temperature, in a buffered aqueous solution of pH 5.5-8, preferably pH 6.5-7.5.

In another preferred embodiment of the invention, an exendin-linker conjugate carrying a maleimide group is reacted with a thiol-functionalized hydrogel according to the invention at temperatures between room temperature and 4° C., more preferred at room temperature, in a buffered aqueous solution of pH 5.5-8, preferably pH 6.5-7.5. Subsequently, the corresponding resulting drug-linker-hydrogel conjugate is treated with a low molecular weight compound comprising a maleimide group, preferably a maleimide-containing compound of 100-300 Da, e.g. N-ethyl-maleimide, at temperatures between room temperature and 4° C., more preferred at room temperature, in a buffered aqueous solution of pH 5.5-8, preferably 6.5-7.5.

Another aspect of the present invention is a process comprising the steps of
(a) contacting at temperatures between room temperature and 4° C. in a buffered aqueous solution of pH 5.5-8 an aqueous suspension comprising maleimide-functionalized hydrogel microparticles with a solution comprising an exendin-linker reagent of the present invention, wherein the chemical functional group of $L^2$* comprises a thiol group, resulting in an exendin-linker-hydrogel conjugate;
(b) optionally, treating the exendin-linker-hydrogel conjugate from step (a) with a thiol-containing compound of 34 Da to 500 Da at temperatures between room temperature and 4° C. in a buffered aqueous solution of pH 5.5-8.

Another aspect of the present invention is a process comprising the steps of
(a) contacting at temperatures between room temperature and 4° C. in a buffered aqueous solution of pH 5.5-8 an aqueous suspension comprising thiol-functionalized hydrogel microparticles with a solution comprising an exendin-linker reagent of the present invention, wherein the chemical functional group of $L^2$* comprises a maleimide group, resulting in an exendin-linker-hydrogel conjugate;
(b) optionally, treating the exendin-linker-hydrogel conjugate from step (a) with a maleimide-containing compound of 100 to 300 Da at temperatures between room temperature and 4° C. in a buffered aqueous solution of pH 5.5-8.

A particularly preferred method for the preparation of a prodrug of the present invention comprises the steps of
(a) reacting a compound of formula $C(A'-X^1)_4$, wherein $A'-X^1$ represents A before its binding to Hyp or a precursor of Hyp and $X^1$ is a suitable functional group, with a compound of formula $Hyp'-X^2$, wherein $Hyp'-X^2$ represents Hyp before its binding to A or a precursor of Hyp and $X^2$ is a suitable functional group to react with $X^1$;
(b) optionally reacting the resulting compound from step (a) in one or more further steps to yield a compound of formula $C(A-Hyp)_4$ having at least four functional groups;
(c) reacting the at least four functional groups of the resulting compound from step (b) with a poly(ethylene glycol) based crosslinker precursor, wherein the active ester groups of the crosslinker precursor are used in a sub-stoichiometric amount compared to the total number of reactive functional groups of $C(A-Hyp)_4$ to yield a hydrogel;
(d) reacting remaining un-reacted functional groups (representing the reactive functional groups of the backbone comprised in the hydrogel) in the hydrogel backbone of step (c) with a covalent conjugate of biologically active moiety and transient prodrug linker or first reacting the un-reacted functional groups with the transient prodrug linker and subsequently with the biologically active moiety;
(e) optionally capping remaining un-reacted functional groups to yield a prodrug of the present invention.

Specifically, hydrogels for the exendin prodrugs of the present invention are synthesized as follows:

For bulk polymerization, backbone reagent and crosslinker reagent are mixed in a ratio amine/active ester of 2:1 to 1.05:1.

Both backbone reagent and crosslinker reagent are dissolved in DMSO to give a solution with a concentration of 5 to 50 g per 100 mL, preferably 7.5 to 20 g per 100 ml and most preferably 10 to 20 g per 100 ml.

To effect polymerization, 2 to 10% (vol.) N,N,N',N'-tetramethylethylene diamine (TMEDA) are added to the DMSO solution containing crosslinker reagent and backbone reagent and the mixture is shaken for 1 to 20 sec and left standing. The mixture solidifies within less than 1 min.

Such hydrogel according to the invention is preferably comminuted by mechanical processes such as stirring, crushing, cutting pressing, or milling, and optionally sieving.

For emulsion polymerization, the reaction mixture is comprised of the dispersed phase and the continuous phase.

For the dispersed phase, backbone reagent and crosslinker reagent are mixed in a ratio amine/active ester of 2:1 to 1.05:1 and are dissolved in DMSO to give a to give a solution with a concentration of 5 to 50 g per 100 mL, preferably 7.5 to 20 g per 100 ml and most preferably 10 to 20 g per 100 ml.

The continuous phase is any solvent, that is not miscible with DMSO, not basic, aprotic and shows a viscosity lower than 10 Pa*s. Preferably, the solvent is not miscible with DMSO, not basic, aprotic, shows a viscosity lower than 2 Pa*s and is non-toxic. More preferably, the solvent is a saturated linear or branched hydrocarbon with 5 to 10 carbon atoms. Most preferably, the solvent is n-heptane.

To form an emulsion of the dispersed phase in the continuous phase, an emulsifier is added to the continuous phase before adding the dispersed phase. The amount of emulsifier is 2 to 50 mg per mL dispersed phase, more preferably 5 to 20 mg per mL dispersed phase, most preferably 10 mg per mL dispersed phase.

The emulsifier has an HLB-value of 3 to 8. Preferably, the emulsifier is a triester of sorbitol and a fatty acid or an poly(hydroxyl fatty acid)-poly(ethylene glycol) conjugate. More preferably, the emulsifier is an poly(hydroxy-fatty acid)-polyethylene glycol conjugate, with a linear poly(ethylene glycol) of a molecular weight in the range of from 0.5 kDa to 5 kDa and poly(hydroxy-fatty acid) units of a molecular weight in the range of from 0.5 kDa to 3 kDa on each end of the chain. Most preferably, the emulsifier is poly(ethylene glycol) dipolyhydroxy stearate, Cithrol DPHS (Cithrol DPHS, former Arlacel P135, Croda International Plc).

Droplets of the dispersed phase are generated by stirring with an axial flow impeller with a geometry similar to stirrers such as Isojet, Intermig, Propeller (EKATO Rühr-and Mischtechnik GmbH, Germany), most preferably similar to Isojet with a diameter of 50 to 90% of the reactor diameter. Preferably, stirring is initiated before addition of the dispersed phase. Stirrer speed is set to 0.6 to 1.7 m/s. The dispersed phase is added at room temperature, and the concentration of the disperse phase is 2% to 70%, preferably 5 to 50%, more preferably 10 to 40%, and most preferably 20 to 35% of the total reaction volume. The mixture of dispersed phase, emulsifier and continuous phase is stirred for 5 to 60 min before adding the base to the effect polymerization.

5 to 10 equivalents (referred to each amide bond to be formed) of a base are added to the mixture of dispersed and continuous phase. The base is aprotic, non nucleophilic and soluble in the disperse phase. Preferably, the base is aprotic, non nucleophilic, well soluble in both disperse phase and DMSO. More preferably, the base is aprotic, non nucleophilic, well soluble in both disperse phase and DMSO, an amine base and non-toxic. Most preferably, the base is N,N,N',N'-tertramethylethylene diamine (TMEDA). Stirring in the presence of base is continued for 1 to 16 h.

During stirring, droplets of dispersed phase are hardened to become crosslinked hydrogel beads according to the invention which can be collected and fractionation according to size is performed on a vibrational continuous sieving machine with a 75 µm and a 32 µm deck to give hydrogel microparticles according to the invention.

Another aspect of the present invention is an exendin-linker conjugate intermediate D-L', wherein L' is of formula (III)

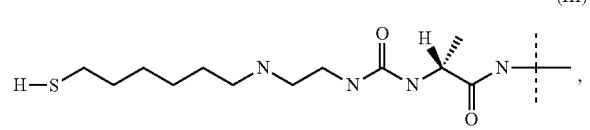

wherein the dashed line indicates the attachment to one of the amino groups of the exendin moiety by forming an amide bond;

Another aspect of the present invention are exendin-linker reagents D-L*, wherein
D represents an exendin moiety; and
L* is a non-biologically active linker reagent represented by formula (IV),

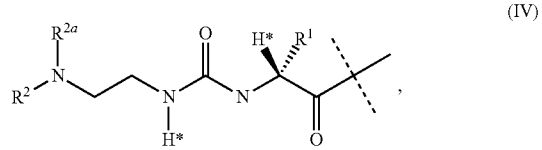

wherein the dashed line indicates the attachment to one of the amino groups of the exendin by forming an amide bond;
$R^1$ is selected from $C_{1-4}$ alkyl, preferably $CH_3$;

$R^2$, $R^{2a}$, are independently selected from the group consisting of H and $C_{1-4}$ alkyl,
wherein L* is substituted with one $L^{2*}$ and optionally further substituted, provided that the hydrogens marked with the asterisks in formula (IV) are not replaced by a substituent and wherein
$L^{2*}$ is a spacer connected to L* and comprising a chemical functional group intended for conjugation to a hydrogel.
Preferably, $R^2$ in formula (IV) is replaced by $L^{2*}$.
Preferably, $R^1$ in formula (IV) is $CH_2$-$L^{2*}$.
Preferably, L* in formula (IV) is not further substituted.
Preferably, $L^{2*}$ comprises a thiol group.
Preferably, $L^{2*}$ comprises a maleimide group.
Preferably, $L^{2*}$ is $L^2$-H.

The hydrogel for the prodrug of the present invention can be obtained from the preparation methods in the form of a shaped article, such as a mesh or a stent or microparticles. Most preferably, the hydrogel is formed into microparticulate beads which can be administered as subcutaneous or intramuscular injection by means of a standard syringe. Such soft beads may have a diameter of between 1 and 500 micrometer.

Preferably, the microparticles have a diameter of between 10 and 100 micrometer if suspended in an isotonic aqueous formulation buffer, more preferably a diameter of between 20 and 100 micrometer, most preferably a diameter of between 25 and 80 micrometer.

Preferably, the microparticles can be administered by injection through a needle smaller than 0.6 mm inner diameter, preferably through a needle smaller than 0.3 mm inner diameter, more preferably through a needle smaller than 0.225 mm inner diameter, even more preferably through a needle smaller than 0.175 mm inner diameter, and most preferably through a needle small than 0.16 mm inner diameter.

It is understood that the terms "can be administered by injection", "injectable" or "injectability" refer to a combination of factors such as a certain force applied to a plunger of a syringe containing the biodegradable hydrogel according to the invention swollen in a liquid at a certain concentration (w/v) and at a certain temperature, a needle of a given inner diameter connected to the outlet of such syringe, and the time required to extrude a certain volume of the biodegradable hydrogel according to the invention from the syringe through the needle.

In order to provide for injectability, a volume of 1 mL of the exendin prodrugs according to the invention swollen in water to a concentration of at least 5% (w/v) and contained in a syringe holding a plunger of a diameter of 4.7 mm can be extruded at room temperature within 10 seconds by applying a force of less than 50 Newton.

Preferably, injectability is achieved for an exendin prodrug according to the invention swollen in water to a concentration of ca. 10% (w/v).

Another aspect of the present invention is a process for preparing a needle injectable prodrug comprising the step of
 (a) preparing an exendin hydrogel prodrug of the present invention in the form of microparticles;
 (b) sieving the microparticles
 (c) selecting a fraction with a prodrug bead diameter of between 25 and 80 µm.
 (d) suspending the bead fraction of step (c) in an aqueous buffer solution suitable for injection.

Another aspect of the present invention is a needle-injectable prodrug obtainable from the process described above, wherein the needle injectable prodrug is injectable through a needle with an inner diameter of less than 300 µm, preferably through a needle with an inner diameter of less than 225 μm, and more preferably through a needle with an inner diameter of less than 175 μm.

Another aspect of the present invention is a pharmaceutical composition comprising a prodrug of the present invention or a pharmaceutically acceptable salt thereof together with a pharmaceutically acceptable excipient. The pharmaceutical composition is further described in the following paragraphs.

The composition of exendin-hydrogel prodrug may be provided as a suspension composition or as a dry composition. Preferably, the pharmaceutical composition of exendin-hydrogel prodrug is a dry composition. Suitable methods of drying are, for example, spray-drying and lyophilization (freeze-drying). Preferably, the pharmaceutical composition of exendin-hydrogel prodrug is dried by lyophilization.

Preferably, the exendin hydrogel prodrug is sufficiently dosed in the composition to provide therapeutically effective amount of exendin for at least three days in one application. More preferably, one application of the exendin hydrogel prodrug is sufficient for one week.

The pharmaceutical composition of exendin-hydrogel prodrug according to the present invention contains one or more excipients.

Excipients used in parenteral compositions may be categorized as buffering agents, isotonicity modifiers, preservatives, stabilizers, anti-adsorption agents, oxidation protection agents, viscosifiers/viscosity enhancing agents, or other auxiliary agents. In some cases, these ingredients may have dual or triple functions. The compositions of exendin-hydrogel prodrugs according to the present invention contain one or more than one excipient, selected from the groups consisting of:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability (ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum (iii) Preservatives and/or antimicrobials: multidose parenteral preparations require the addition of preservatives at a sufficient concentration to minimize risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride (iv) Stabilizers: Stabilisation is achieved by strengthening of the protein-stabilising forces, by destabilisation of the denatured stater, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used (v) Anti-adsorption agents: Mainly ionic or non-ionic surfactants or other proteins or soluble polymers are used to coat or adsorb competitively to the inner surface of the composition's or composition's container. E.g., poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically a monolayer of surfactant is formed at the interface just above the CMC value (vi) Lyo- and/or cryoprotectants: During freeze- or spray drying, excipients may counteract the destabilising effects caused by hydrogen bond breaking and water removal. For this purpose sugars and polyols may be used but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol:sucrose are known to enhance physical stability of a lyophilized cake. Mannitol may also be combined with trehalose. Trehalose may also be combined with sorbitol or sorbitol used as the sole protectant. Starch or starch derivatives may also be used (vii) Oxidation protection agents: antioxidants such as ascorbic acid, ectoine, methionine, glutathione, monothioglycerol, morin, polyethylenimine (PEI), propyl gallate, vitamin E, chelating agents such as citric acid, EDTA, hexaphosphate, thioglycolic acid (viii) Viscosifiers or viscosity enhancers: retard settling of the particles in the vial and syringe and are used in order to facilitate mixing and resuspension of the particles and to make the suspension easier to inject (i.e., low force on the syringe plunger). Suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly(glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly(acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly (lactide-co-glycolide) (PLGA), and hydrophilic B-blocks, such as polyethylene glycol (PEG) or polyvinyl pyrrolidone. Such block copolymers as well as the abovementioned poloxamers may exhibit reverse thermal gelation behavior (fluid state at room temperature to facilitate administration and gel state above sol-gel transition temperature at body temperature after injection).

(ix) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue. A spreading agent such as but not limited to hyaluronidase temporarily decreases the viscosity of the extracellular matrix and promotes diffusion of injected drugs.

(x) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture Preferably, the composition of exendin-hydrogel prodrug contains one or more than one viscosifier and/or viscosity modifying agent.

The term "excipient" preferably refers to a diluent, adjuvant, or vehicle with which the therapeutic is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Examples of suitable pharmaceutical excipients are described in "Remington's Pharmaceutical Sciences" by E. W. Martin. Such compositions will contain a therapeutically effective amount of the therapeutic, preferably in purified form, together with a suitable amount of excipient so as to provide the form for proper administration to the patient. The formulation should suit the mode of administration.

In a general embodiment a pharmaceutical composition of the present invention whether in dry form or as a suspension or in another form may be provided as single or multiple dose composition.

In one embodiment of the present invention, the dry composition of exendin-hydrogel prodrug is provided as a single dose, meaning that the container in which it is supplied contains one pharmaceutical dose.

Thus, in another aspect of the present invention the composition is provided as a single dose composition.

Preferably, the suspension composition is a multiple dose composition, meaning that it contains more than one therapeutic dose. Preferably, a multiple dose composition contains at least 2 doses. Such multiple dose composition of exendin-hydrogel can either be used for different patients in need thereof or is intended for use in one patient, wherein the remaining doses are stored after the application of the first dose until needed.

In another aspect of the present invention the composition is comprised in a container. Preferably the container is a dual-chamber syringe. Especially the dry composition according to the present invention is provided in a first chamber of the dual-chamber syringe and reconstitution solution is provided in a second chamber of the dual-chamber syringe.

Prior to applying the dry composition of exendin-hydrogel prodrug to a patient in need thereof, the dry composition is reconstituted. Reconstitution can take place in the container in which the dry composition of exendin-hydrogel prodrug is provided, such as in a vial, syringe, dual-chamber syringe, ampoule, and cartridge. Reconstitution is done by adding a predefined amount of reconstitution solution to the dry composition. Reconstitution solutions are sterile liquids, such as water or buffer, which may contain further additives, such as preservatives and/or antimicrobials. If the exendin-hydrogel prodrug composition is provided as single dose, the reconstitution solution may contain one or more preservative and/or antimicrobial. Preferably, the reconstitution solution is sterile water. If the composition of exendin-hydrogel prodrug is a multiple dose composition, it is preferred that the reconstitution solution contains one or more preservative and/or antimicrobial, such as, for example, benzylalcohol and cresol.

An additional aspect of the present invention relates to the method of administration of a reconstituted exendin hydrogel prodrug composition. The exendin hydrogel prodrug composition can be administered by methods of injection or infusion, including intradermal, subcutaneous, intramuscular, intravenous, intraosseous, and intraperitoneal.

A further aspect is a method of preparing a reconstituted composition comprising a therapeutically effective amount of an exendin hydrogel prodrug, and optionally one or more pharmaceutically acceptable excipients, wherein the exendin is transiently linked to a hydrogel, the method comprising the step of contacting the composition of the present invention with a reconstitution solution.

Another aspect is a reconstituted composition comprising a therapeutically effective amount of a exendin hydrogel prodrug, and optionally one or more pharmaceutically acceptable excipients, wherein the exendin is transiently linked to a hydrogel obtainable by the method above.

Another aspect of the present invention is the method of manufacturing a dry composition of exendin-hydrogel prodrug. In one embodiment, such suspension composition is made by (i) admixing the exendin-hydrogel prodrug with one or more excipients,
(ii) transferring amounts equivalent to single or multiple doses into a suitable container,
(iii) drying the composition in said container, and
(iv) sealing the container.

Suitable containers are vials, syringes, dual-chamber syringes, ampoules, and cartridges.

Another aspect is a kit of parts. When the administration device is simply a hypodermic syringe then the kit may comprise the syringe, a needle and a container comprising the dry exendin-hydrogel prodrug composition for use with the syringe and a second container comprising the reconstitution solution. In more preferred embodiments, the injection device is other than a simple hypodermic syringe and so the separate container with reconstituted exendin-hydrogel prodrug is adapted to engage with the injection device such that in use the liquid composition in the container is in fluid connection with the outlet of the injection device. Examples of administration devices include but are not limited to hypodermic syringes and pen injector devices. Particularly preferred injection devices are the pen injectors in which case the container is a cartridge, preferably a disposable cartridge.

A preferred kit of parts comprises a needle and a container containing the composition according to the present invention and optionally further containing a reconstitution solution, the container being adapted for use with the needle. Preferably, the container is a dual-chamber syringe.

In another aspect, the invention provides a cartridge containing a composition of exendin-hydrogel prodrug as hereinbefore described for use with a pen injector device. The cartridge may contain a single dose or multiplicity of doses of exendin.

In one embodiment of the present invention the suspension composition of exendin-hydrogel prodrug does not only comprise an exendin-hydrogel prodrug and one or more than one excipients, but also other biologically active agents, either in their free form or as prodrugs. Preferably, such additional one or more biologically active agent is a prodrug, more preferably a hydrogel prodrug. Such biologically active agents include, but are not limited to, compounds of the following classes:

(i) Sulfonylureas, such as, for example, chlorpropamide, tolazamide, tolbutamide, glyburide, glipizide, glimepiride, glibenclamide, gliclazide and the like;
(ii) Meglitinides, such as, for example, repaglinide, nateglinide or mitiglinide;
(iii) Glucagon-like Peptide-1(GLP-1) and it's mimetics, Glucose-insulinotropic peptide (GIP) and it's mimetics, Exendin and it's mimetics, and Dipeptyl Protease Inhibitors (DPPIV);
(iv) Biguanides, such as, for example, metformin;
(v) Thiazolidinediones, such as, for example, rosiglitazone, pioglitazone, troglitazone, isaglitazone (known as MCC-555), 2-[2-[(2R)-4-hexyl-3,4-dihydro-3-oxo-2H-1,4-benzoxazin-2-yl]ethoxy]-benzene acetic acid, ciglitazone, rosiglitazone or the compounds disclosed in WO 97/41097 by Dr. Reddy's Research Foundation, especially 5-[[4-[(3,4-dihydro-3-methyl-4-oxo-2-quinazolinylmethoxy]phenyl]methyl]-2,4-thiazolidinedione and the like;
(vi) GW2570, and the like;
(vii) Retinoid-X receptor (RXR) modulators, such as, for example, targretin, 9-cis-retinoic acid, and the like;
(viii) Other insulin sensitizing agents, such as, for example, INS-1, PTP-1B inhibitors, GSK3 inhibitors, glycogen phosphorylase a inhibitors, fructose-1,6-bisphosphatase inhibitors, and the like;
(ix) Insulins, including regular or short-acting, intermediate-acting, and long-acting insulins, inhaled insulin, insulin derivatives and insulin analogues, such as insulin molecules with minor differences in the natural amino acid sequence;
(x) Small molecule mimics of insulin, including, but not limited to L-783281, TE-17411, and the like;
(xi) Sodium-dependent glucose transporter 1 and/or 2 (SGLT1, SGLT2) inhibitors, for example KGA-2727, T-1095, T-1095A, SGL-0010, AVE 2268, SAR 7226, SGL-5083, SGL-5085, SGL-5094, ISIS-388626, sergliflozin, dapagliflozin or remogliflozin etabonate, canagliflozin, phlorizin, and the like;
(xii) Amylin agonists which include, but are not limited to pramlintide, and the like;
(xiii) Glucagon antagonists such as AY-279955, and the like.

(xiv) Gut hormones and modulators of gut hormone activity, such as Somatostatin, Oxyntomodulin, Cholecystokinin, Incretins, Ghrelin, $PYY_{3-36}$, and the like.

Insulins as described above may independently be selected from the group consisting of bovine insulins, porcine insulins, and human insulins. More preferably insulin is independently selected from human insulins. An insulin may be selected from unmodified insulins, more particularly from bovine insulins, porcine insulins, and human insulins.

Insulin derivatives are derivatives of a naturally occurring insulin and/or an insulin analog, which are obtained by chemical modification. The chemical modification may consist, for example, in the addition of one or more defined chemical groups onto one or more amino acids.

Insulin analogs which are described in EP 0 214 826, EP 0 375 437, EP 0 678 522, EP 0 885 961, EP 0 419 504, WO 92/00321, German patent applications 10 2008 003 568.8 and 10 2008 003 566.1, and EP-A 0 368 187 may be part of the combinations of the invention. The documents EP 0 214 826, EP 0 375 437, EP 0 678 522, EP 0 419 504, WO 92/00321, and EP-A 0 368 187 are included herein by reference.

One preferred insulin analog may be selected from the group consisting of Gly(A21)-Arg(B31)-Arg(B32) human insulin (insulin glargine, Lantus); Arg(A0)-His(A8)-Glu (A15)-Asp(A18)-Gly(A21)-Arg(B31)-Arg(B32) human insulin amide, Lys(B3)-Glu(B29) human insulin; $Lys^{B28}Pro^{B29}$ human insulin (insulin lyspro), B28 Asp human insulin (insulin aspart), human insulin in which proline in position B28 has been substituted by Asp, Lys, Leu, Val or Ala and where Lys in position B29 may be substituted by Pro; AlaB26 human insulin; des(B28-B30) human insulin; des (B27) human insulin or B29Lys(ε-tetradecanoyl), des(B30) human insulin (insulin detemir).

A preferred insulin derivative may be selected from the group consisting of B29-N-myristoyl-des(B30) human insulin, B29-N-palmitoyl-des(B30) human insulin, B29-N-myristoyl human insulin, B29-N-palmitoyl human insulin, B28-N-myristoyl $Lys^{B28}Pro^{B29}$ human insulin, B28-N-palmitoyl-$Lys^{B28}Pro^{B29}$ human insulin, B30-N-myristoyl-$Thr^{B29}Lys^{B30}$ human insulin, B30-N-palmitoyl-$Thr^{B29}Lys^{B30}$ human insulin, B29-N—(N-palmitoyl-Y-glutamyl)-des(B30) human insulin, B29-N—(N-lithocholyl-Y-glutamyl)-des(B30) human insulin, B29-N-(ω-carboxyheptadecanoyl)-des(B30) human insulin, and B29-N-(ω-carboxyheptadecanoyl) human insulin.

A more highly preferred insulin derivative is selected from the group consisting of Gly(A21)-Arg(B31)-Arg(B32) human insulin, $Lys^{B28}Pro^{B29}$ human insulin (insulin lyspro), B28 Asp human insulin (insulin aspart), B29Lys(ε-tetradecanoyl), desB30 human insulin (insulin detemir).

Preferably, such additional one or more biologically active agent is a hydrogel prodrug of an insulin as described in WO2011/012718 and WO2011/012719.

In addition to antidiabetic agents, bioactive compounds may be anti-obesity agents such as orlistat, a pancreatic lipase inhibitor, which prevents the breakdown and absorption of fat; or sibutramine, an appetite suppressant and inhibitor of the reuptake of serotonin, norepinephrine and dopamine in the brain, growth factors increasing fat mobilization (eg, growth hormone, IGF-1, growth hormone releasing factor), oxyntomodulin and ghrelin modulators. Other potential bioactive anti-obesity agents include, but are not limited to, appetite-suppressants acting through adrenergic mechanisms such as benzphetamine, phenmetrazine, phentermine, diethylpropion, mazindol, sibutramine, phenylpropanolamine or, ephedrine; appetite-suppressant agents acting through serotonergic mechanisms such as quipazine, fluoxetine, sertraline, fenfluramine, or dexfenfluramine; appetite-suppressant agents acting through dopamine mechanisms, eg, apomorphine; appetite-suppressant agents acting through histaminergic mechanisms (eg, histamine mimetics, H3 receptor modulators); enhancers of energy expenditure such as beta-3 adrenergic agonists and stimulators of uncoupling protein function; leptin and leptin mimetics (eg, meterleptin); neuropeptide Y antagonists; melanocortin-1, 3 and 4 receptor modulators; cholecystokinin agonists; glucagon-like peptide-1 (GLP-1) mimetics and analogues (eg, Exendin); androgens (eg, dehydroepiandrosterone and derivatives such as etiocholandione), testosterone, anabolic steroids (eg, oxandrolone), and steroidal hormones; galanin receptor antagonists; cytokine agents such as ciliary neurotrophic factor; amylase inhibitors; enterostatin agonists/mimetics; orexin/hypocretin antagonists; urocortin antagonists; bombesin agonists; modulators of protein kinase A; corticotropin-releasing factor mimetics; cocaine- and amphetamine-regulated transcript mimetics; calcitonin-gene related peptide mimetics; and fatty acid synthase inhibitors.

In an alternative embodiment, the exendin-hydrogel prodrug composition according to the present invention is combined with a second biologically active compound in such way that the exendin-hydrogel prodrug is administered to a patient in need thereof first, followed by the administration of the second compound. Alternatively, the exendin-hydrogel composition is administered to a patient in need thereof after another compound has been administered to the same patient.

Yet another aspect of the present invention is a prodrug of the present invention or a pharmaceutical composition of the present invention for use as a medicament.

Yet another aspect of the present invention is a prodrug of the present invention or a pharmaceutical composition of the present invention for use in a method of treating or preventing diseases or disorders which can be treated by exendin. Said compositions are for use in a method of treating or preventing diseases or disorders known for exendin and exendin agonists, for example, for treatment and prevention of hyperglycemia and for treatment and prevention of diabetes mellitus of any type, e.g. insulin-dependent diabetes mellitus, non insulin dependent diabetes mellitus, prediabetes or gestational diabetes mellitus, for prevention and treatment of metabolic syndrome and/or obesity and/or eating disorders, insulin resistance syndrome, lowering plasma lipid level, reducing the cardiac risk, reducing the appetite, reducing the body weight, etc.

Patients in need of treatment with the long acting exendin compositions described in the present invention are at high risk of developing comorbidities. Accordingly, the combination of the long acting exendin of the present with appropriate bioactive compounds may be used, e.g., for the prevention, delay of progression or treatment of diseases and disorders selected from the group consisting of hypertension (including but not limited to isolated systolic hypertension and familial dyslipidemic hypertension), congestive heart failure, left ventricular hypertrophy, peripheral arterial disease, diabetic retinopathy, macular degeneration, cataract, diabetic nephropathy, glomerulosclerosis, chronic renal failure, diabetic neuropathy, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertriglyceridemia insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance.

Prevention, delay of progression or treatment of diseases and disorders selected from the group above can be achieved by combination of the long acting exendin composition of the present invention with at least one bioactive compound selected from the drug classes used for treating said conditions, including $AT_1$-receptor antagonists; angiotensin converting enzyme (ACE) inhibitors; renin inhibitors; beta adrenergic receptor blockers; alpha adrenergic receptor blockers; calcium channel blockers; aldosterone synthase inhibitors; aldosterone receptor antagonists; neutral endopeptidase (NEP) inhibitors; dual angiotensin converting enzyme/neutral endopetidase (ACE/NEP) inhibitors; an endothelin receptor antagonists; diuretics; statins; nitrates; anti clotting agents; natriuretic peptides; *digitalis* compounds; PPAR modulators.

In case the biologically active agents; prodrugs, especially hydrogel prodrugs contain one or more acidic or basic groups, the invention also comprises their corresponding pharmaceutically or toxicologically acceptable salts, in particular their pharmaceutically utilizable salts. Thus, the prodrugs which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Prodrugs which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the prodrugs simultaneously contain acidic and basic groups in the molecule, the invention also includes, in addition to the salt forms mentioned, inner salts or betaines (zwitterions). The respective salts can be obtained by customary methods which are known to the person skilled in the art like, for example by contacting these with an organic or inorganic acid or base in a solvent or dispersant, or by anion exchange or cation exchange with other salts. The present invention also includes all salts of the prodrugs which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency such as the EMEA (Europe) and/or the FDA (US) and/or any other national regulatory agency for use in animals, preferably in humans.

Yet another aspect of the present invention is a method of treating, controlling, delaying or preventing in a mammalian patient, preferably in a human, in need of the treatment of one or more conditions comprising administering to said patient a therapeutically effective amount of a prodrug of the present invention or a pharmaceutical composition of the present invention or a pharmaceutically acceptable salt thereof.

FIG. 1 shows release kinetics of compounds 8, 10, 12, 14 and 16 at pH 7.4, 37° C.

EXAMPLES

Materials and Methods

Exendin-4 [Seq ID No:1] on resin (loading approx. 0.1 mmol/g) synthesized by Fmoc strategy was obtained from CASLO Laboratory Aps, Lyngby, Denmark. Lixisenatide [Seq ID No 21] and GLP-1 [Seq ID No 13] on resin (loading approx. 0.1 mmol/g) synthesized by Fmoc strategy was obtained from Peptide Specialty Laboratories, Heidelberg, Germany. The peptides were fully side chain protected and had a free N-Terminus.

Amino 4-arm PEG 5 kDa was obtained from JenKem Technology, Beijing, P. R. China. N-(3-maleimidopropyl)-21-amino-4,7,10,13,16,19-hexaoxa-heneicosanoic acid NHS ester (Mal-PEG6-NHS) was obtained from Celares GmbH, Berlin, Germany. 6-(S-Tritylmercapto)hexanoic acid was purchased from Polypeptide, Strasbourg, France. Amino acids used were of L configuration if not stated otherwise.

All other chemicals were from Sigma-ALDRICH Chemie GmbH, Taufkirchen, Germany.

Fmoc Deprotection:

For Fmoc protecting-group removal, the resin was agitated with 2/2/96 (v/v/v) piperidine/DBU/DMF (two times, 10 min each) and washed with DMF (ten times).

RP-HPLC Purification:

RP-HPLC was done on a 100×20 mm or 100×40 mm C18 ReproSil-Pur 300 ODS-3 5 µm column (Dr. Maisch, Ammerbuch, Germany) connected to a Waters 600 HPLC System and Waters 2487 Absorbance detector unless otherwise stated. Linear gradients of solution A (0.1% TFA in $H_2O$) and solution B (0.1% TFA in acetonitrile) were used. HPLC fractions containing product were pooled and lyophilized.

Flash Chromatography

Flash chromatography purifications were performed on an Isolera One system from Biotage AB, Sweden, using Biotage KP-Sil silica cartridges and n-heptane and ethyl acetate as eluents. Products were detected at 254 nm.

For hydrogel beads, syringes equipped with polyethylene frits were used as reaction vessels or for washing steps.

Analytical ultra-performance LC (UPLC) was performed on a Waters Acquity system equipped with a Waters BEH300 C18 column (2.1×50 mm, 1.7 µm particle size) coupled to a LTQ Orbitrap Discovery mass spectrometer from Thermo Scientific.

MS of PEG products showed a series of $(CH_2CH_2O)_n$, moieties due to polydispersity of PEG starting materials. For easier interpretation only one single representative m/z signal is given in the examples.

Peptide content of hydrogel: Peptide content is expressed as % peptide weight in relation to hydrogel brutto weight (sum of weight of maleimide functionalized hydrogel and peptide linker thiol). Weight of peptide linker thiol in hydrogel (and thus weight of peptide alone) was determined by consumption of peptide linker thiol during conjugation reaction with maleimide functionalized hydrogel. Consumption of peptide linker thiol was determined by Ellman test (Ellman, G. L. et al., *Biochem. Pharmacol.*, 1961, 7, 88-95).

Example 1

Synthesis of Backbone Reagent 1g

Backbone reagent 1g was synthesized from amino 4-arm PEG5000 1a according to following scheme:

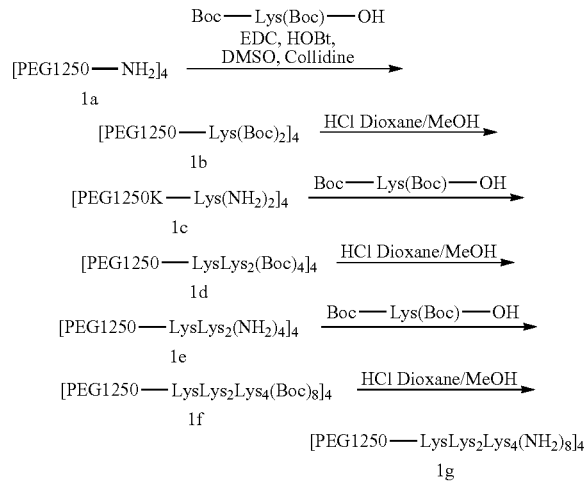

For synthesis of compound 1b, amino 4-arm PEG5000 1a (MW ca. 5200 g/mol, 5.20 g, 1.00 mmol, HCl salt) was dissolved in 20 mL of DMSO (anhydrous). Boc-Lys(Boc)-OH (2.17 g, 6.25 mmol) in 5 mL of DMSO (anhydrous), EDC HCl (1.15 g, 6.00 mmol), HOBt.H$_2$O (0.96 g, 6.25 mmol), and collidine (5.20 mL, 40 mmol) were added. The reaction mixture was stirred for 30 min at RT.

The reaction mixture was diluted with 1200 mL of DCM and washed with 600 mL of 0.1 N H$_2$SO$_4$ (2×), brine (1×), 0.1 M NaOH (2×), and 1/1 (v/v) brine/water (4×). Aqueous layers were reextracted with 500 mL of DCM. Organic phases were dried over Na$_2$SO$_4$, filtered and evaporated to give 6.3 g of crude product 1b as colorless oil. Compound 1 b was purified by RP-HPLC.

Yield 3.85 g (59%) colorless glassy product 1b.

MS: m/z 1294.4=$[M+5H]^{5+}$ (MW calculated for $[M+5H]^{5+}$=1294.6).

Compound 1c was obtained by stirring of 3.40 g of compound 1b (0.521 mmol) in 5 mL of methanol and 9 mL of 4 N HCl in dioxane at RT for 15 min. Volatiles were removed in vacuo. The product was used in the next step without further purification.

MS: m/z 1151.9=$[M+5H]^{5+}$ (MW calculated for $[M+5H]^{5+}$=1152.0).

For synthesis of compound 1d, 3.26 g of compound 1c (0.54 mmol) were dissolved in 15 mL of DMSO (anhydrous). 2.99 g Boc-Lys(Boc)-OH (8.64 mmol) in 15 mL DMSO (anhydrous), 1.55 g EDC HCl (8.1 mmol), 1.24 g HOBt.H$_2$O (8.1 mmol), and 5.62 mL of collidine (43 mmol) were added. The reaction mixture was stirred for 30 min at RT.

Reaction mixture was diluted with 800 mL DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried with Na$_2$SO$_4$, filtered and evaporated to give a glassy crude product.

Product was dissolved in DCM and precipitated with cooled (−18° C.) diethylether. This procedure was repeated twice and the precipitate was dried in vacuo.

Yield: 4.01 g (89%) colorless glassy product 1d, which was used in the next step without further purification.

MS: m/z 1405.4=$[M+6H]^{6+}$ (MW calculated for $[M+6H]^{6+}$=1405.4).

Compound 1e was obtained by stirring a solution of compound 1d (3.96 g, 0.47 mmol) in 7 mL of methanol and 20 mL of 4 N HCl in dioxane at RT for 15 min. Volatiles were removed in vacuo. The product was used in the next step without further purification.

MS: m/z 969.6=$[M+7H]^{7+}$ (MW calculated for $[M+7H]^{7+}$=969.7).

For the synthesis of compound 1 f, compound 1e (3.55 g, 0.48 mmol) was dissolved in 20 mL of DMSO (anhydrous). Boc-Lys(Boc)-OH (5.32 g, 15.4 mmol) in 18.8 mL of DMSO (anhydrous), EDC HCl (2.76 g, 14.4 mmol), HOBt.H$_2$O (2.20 g, 14.4 mmol), and 10.0 mL of collidine (76.8 mmol) were added. The reaction mixture was stirred for 60 min at RT.

The reaction mixture was diluted with 800 mL of DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried over Na$_2$SO$_4$, filtered and evaporated to give crude product 1f as colorless oil.

Product was dissolved in DCM and precipitated with cooled (−18° C.) diethylether. This step was repeated twice and the precipitate was dried in vacuo.

Yield: 4.72 g (82%) colourless glassy product 1f which was used in the next step without further purification.

MS: m/z 1505.3=$[M+8H]^{8+}$ (MW calculated for $[M+8H]^{8+}$=1505.4).

Backbone reagent 1g was obtained by stirring a solution of compound 1f (MW ca. 12035 g/mol, 4.72 g, 0.39 mmol) in 20 mL of methanol and 40 mL of 4 N HCl in dioxane at RT for 30 min. Volatiles were removed in vacuo.

Yield: 3.91 g (100%), glassy product backbone reagent 1g.

MS: m/z 977.2=$[M+9H]^{9+}$ (MW calculated for $[M+9H]^{9+}$= 977.4).

Alternative Synthetic Route for 1g

For synthesis of compound 1 b, to a suspension of 4-Arm-PEG5000 tetraamine (1a) (50.0 g, 10.0 mmol) in 250 mL of iPrOH (anhydrous), boc-Lys(boc)-OSu (26.6 g, 60.0 mmol) and DIEA (20.9 mL, 120 mmol) were added at 45° C. and the mixture was stirred for 30 min.

Subsequently, n-propylamine (2.48 mL, 30.0 mmol) was added. After 5 min the solution was diluted with 1000 mL of MTBE and stored overnight at −20° C. without stirring.

Approximately 500 mL of the supernatant were decanted and discarded. 300 mL of cold MTBE were added and after 1 min shaking the product was collected by filtration through a glass filter and washed with 500 mL of cold MTBE. The product was dried in vacuo for 16 h.

Yield: 65.6 g (74%) 1b as a white lumpy solid

MS: m/z 937.4=$[M+7H]^{7+}$ (MW calculated for $[M+7H]^{7+}$=937.6).

Compound 1c was obtained by stirring of compound 1b from the previous step (48.8 g, 7.44 mmol) in 156 mL of 2-propanol at 40° C. A mixture of 196 mL of 2-propanol and 78.3 mL of acetylchloride was added under stirring within 1-2 min. The solution was stirred at 40° C. for 30 min and cooled to −30° C. overnight without stirring. 100 mL of cold MTBE were added, the suspension was shaken for 1 min and cooled for 1 h at −30° C. The product was collected by filtration through a glass filter and washed with 200 mL of cold MTBE. The product was dried in vacuo for 16 h.

Yield: 38.9 g (86%) 1c as a white powder

MS: m/z 960.1=$[M+6H]^{6+}$ (MW calculated for $[M+6H]^{6+}$= 960.2).

For synthesis of compound 1d, boc-Lys(boc)-OSu (16.7 g, 37.7 mmol) and DIPEA (13.1 mL, 75.4 mmol) were added to a suspension of 1c from the previous step (19.0 g, 3.14 mmol) in 80 ml 2-propanol at 45° C. and the mixture was stirred for 30 min at 45° C.

Subsequently, n-propylamine (1.56 mL, 18.9 mmol) was added. After 5 min the solution was precipitated with 600 mL of cold MTBE and centrifuged (3000 min$^{-1}$, 1 min) The precipitate was dried in vacuo for 1 h and dissolved in 400 mL THF. 200 mL of diethyl ether were added and the product was cooled to −30° C. for 16 h without stirring. The suspension was filtered through a glass filter and washed with 300 mL cold MTBE. The product was dried in vacuo for 16 h.

Yield: 21.0 g (80%) 1d as a white solid

MS: m/z 1405.4=[M+6H]$^{6+}$ (MW calculated for [M+6H]$^{6+}$=1405.4).

Compound 1e was obtained by dissolving compound 1d from the previous step (15.6 g, 1.86 mmol) in 3 N HCl in methanol (81 mL, 243 mmol) and stirring for 90 min at 40° C. 200 mL of MeOH and 700 mL of iPrOH were added and the mixture was stored for 2 h at −30° C. For completeness of crystallization, 100 mL of MTBE were added and the suspension was stored at −30° C. overnight. 250 mL of cold MTBE were added, the suspension was shaken for 1 min and filtered through a glass filter and washed with 100 mL of cold MTBE. The product was dried in vacuo.

Yield: 13.2 g (96%) 1e as a white powder

MS: m/z 679.1=[M+10H]$^{10+}$ (MW calculated for [M+10H]$^{10+}$=679.1).

For the synthesis of compound 1f, boc-Lys(boc)-OSu (11.9 g, 26.8 mmol) and DIPEA (9.34 mL, 53.6 mmol) were added to a suspension of 1e from the previous step, (8.22 g, 1.12 mmol) in 165 ml 2-propanol at 45° C. and the mixture was stirred for 30 min. Subsequently, n-propylamine (1.47 mL, 17.9 mmol) was added. After 5 min the solution was cooled to −18° C. for 2 h, then 165 mL of cold MTBE were added, the suspension was shaken for 1 min and filtered through a glass filter. Subsequently, the filter cake was washed with 4× 200 mL of cold MTBE/iPrOH 4:1 and 1× 200 mL of cold MTBE. The product was dried in vacuo for 16 h.

Yield: 12.8 g, MW (90%) 1f as a pale yellow lumpy solid

MS: m/z 1505.3=[M+8H]$^{8+}$ (MW calculated for [M+8H]$^{8+}$=1505.4).

Backbone reagent 1g was obtained by dissolving 4Arm-PEG5 kDa(-LysLys$_2$Lys$_4$(boc)$_8$)$_4$ (1f) (15.5 g, 1.29 mmol) in 30 mL of MeOH and cooling to 0° C. 4 N HCl in dioxane (120 mL, 480 mmol, cooled to 0° C.) was added within 3 min and the ice bath was removed. After 20 min, 3 N HCl in methanol (200 mL, 600 mmol, cooled to 0° C.) was added within 15 min and the solution was stirred for 10 min at room temperature. The product solution was precipitated with 480 mL of cold MTBE and centrifuged at 3000 rpm for 1 min. The precipitate was dried in vacuo for 1 h and redissolved in 90 mL of MeOH, precipitated with 240 mL of cold MTBE and the suspension was centrifuged at 3000 rpm for 1 min. The product 1g was dried in vacuo Yield: 11.5 g (89%) as pale yellow flakes.

MS: m/z 1104.9=[M+8H]$^{8+}$ (MW calculated for [M+8H]$^{8+}$=1104.9).

Example 2

Synthesis of crosslinker reagent 2d

Crosslinker reagent 2d was prepared from adipic acid mono benzyl ester (English, Arthur R. et al., *Journal of Medicinal Chemistry*, 1990, 33(1), 344-347) and PEG2000 according to the following scheme:

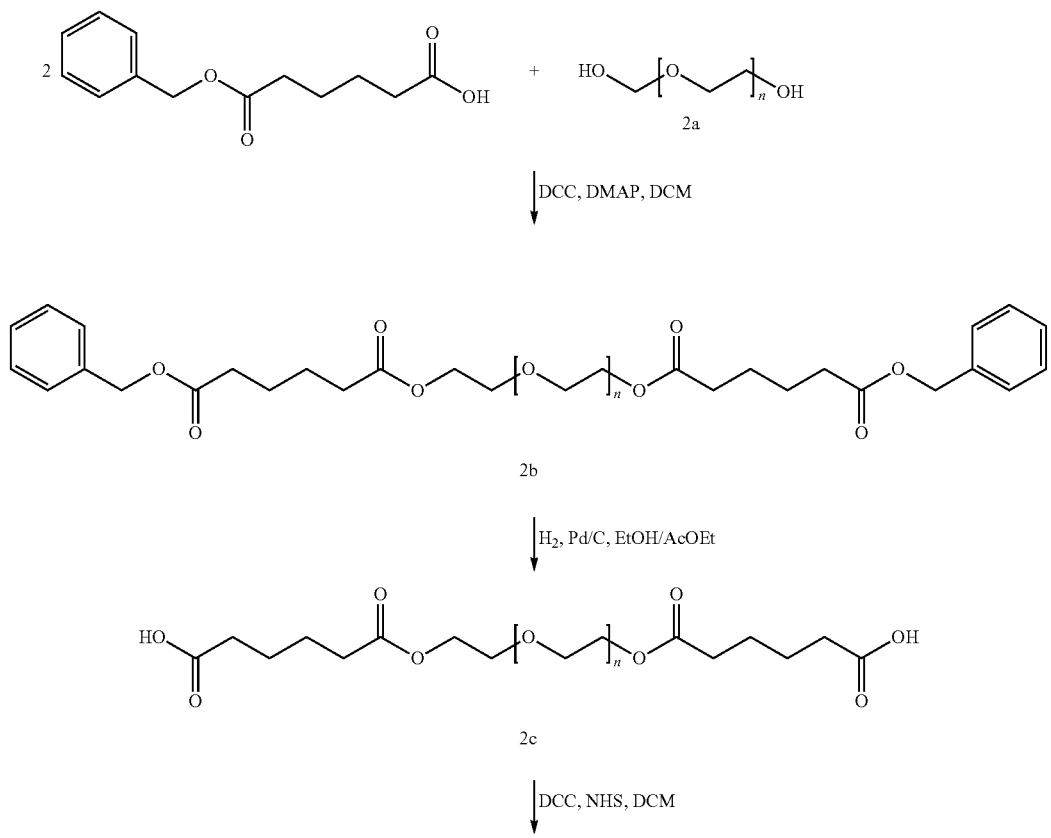

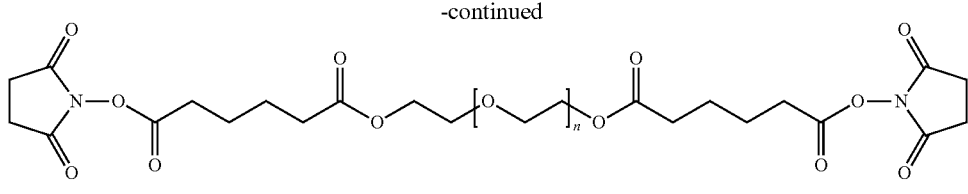

2d n~45

A solution of PEG 2000 (2a) (11.0 g, 5.5 mmol) and benzyl adipate half-ester (4.8 g, 20.6 mmol) in DCM (90.0 mL) was cooled to 0° C. Dicyclohexylcarbodiimide (4.47 g, 21.7 mmol) was added followed by a catalytic amount of DMAP (5 mg) and the solution was stirred and allowed to reach room temperature overnight (12 h). The flask was stored at +4° C. for 5 h. The solid was filtered and the solvent completely removed by distillation in vacuo. The residue was dissolved in 1000 mL 1/1(v/v) diethyl ether/ethyl acetate and stored at RT for 2 hours while a small amount of a flaky solid was formed. The solid was removed by filtration through a pad of Celite®. The solution was stored in a tightly closed flask at −30° C. in the freezer for 12 h until crystallisation was complete. The crystalline product was filtered through a glass frit and washed with cooled diethyl ether (−30° C.). The filter cake was dried in vacuo.

Yield: 11.6 g (86%) 2b as a colorless solid. The product was used without further purification in the next step.

MS: m/z 813.1=$[M+3H]^{3+}$ (MW calculated for $[M+3H]^{3+}$= 813.3)

In a 500 mL glass autoclave PEG2000-bis-adipic acid-bis-benzyl ester 2b (13.3 g, 5.5 mmol) was dissolved in ethyl acetate (180 mL) and 10% Palladium on charcoal (0.4 g) was added. The solution was hydrogenated at 6 bar, 40° C. until consumption of hydrogen had ceased (5-12 h). Catalyst was removed by filtration through a pad of Celite® and the solvent was evaporated in vacuo.

Yield: 12.3 g (quantitative) 2c as yellowish oil. The product was used without further purification in the next step.

MS: m/z 753.1=$[M+3H]^{3+}$ (MW calculated for $[M+3H]^{3+}$= 753.2)

A solution of PEG2000-bis-adipic acid half ester 2c (9.43 g, 4.18 mmol), N-hydroxysuccinimide (1.92 g, 16.7 mmol) and dicyclohexylcarbodiimide (3.44 g, 16.7 mmol) in 75 mL of DCM (anhydrous) was stirred over night at room temperature. The reaction mixture was cooled to 0° C. and precipitate was filtered off. DCM was evaporated and the residue was recrystallized from THF.

Yield: 8.73 g (85%) crosslinker reagent 2d as colorless solid.

MS: m/z 817.8=$[M+3H]^{3+}$ (MW calculated for $[M+3H]^{3+}$= 817.9 g/mol).

Example 3

Preparation of Hydrogel Beads (3) Containing Free Amino Groups

A solution of 1200 mg 1g and 3840 mg 2d in 28.6 mL DMSO was added to a solution of 425 mg Arlacel P135 (Croda International Plc) in 100 mL heptane. The mixture was stirred at 650 rpm with a propeller stirrer for 10 min at 25° C. to form a suspension in a 250 ml reactor equipped with baffles. 4.3 mL TMEDA was added to effect polymerization. After 2 h, the stirrer speed was reduced to 400 rpm and the mixture was stirred for additional 16 h. 6.6 mL of acetic acid were added and then after 10 min 50 mL of water and 50 mL of saturated aqueous sodium chloride solution were added. After 5 min, the stirrer was stopped and the aqueous phase was drained.

For bead size fractionation, the water-hydrogel suspension was wet-sieved on 75, 50, 40, 32 and 20 µm mesh steel sieves. Bead fractions that were retained on the 32, 40, and 50 µm sieves were pooled and washed 3 times with water, 10 times with ethanol and dried for 16 h at 0.1 mbar to give 3 as a white powder.

Amino group content of hydrogel was determined by coupling of a fmoc-amino acid to the free amino groups of the hydrogel and subsequent fmoc-determination as described by Gude, M., J. Ryf, et al. (2002) *Letters in Peptide Science* 9(4): 203-206.

For different batches the amino group content of 3 was determined to be between 0.11 and 0.16 mmol/g.

Example 4

Preparation of Maleimide Functionalized Hydrogel Beads (4) and Determination of Maleimide Substitution

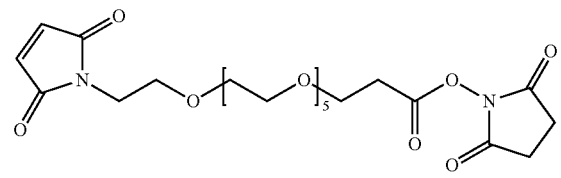

Mal-PEG6-NHS

Hydrogel beads 3 were pre-washed with 99/1 (v/v) DMSO/DIPEA, washed with DMSO and incubated for 45 min with a solution of Mal-PEG6-NHS (2.0 eq relative to theoretical amount of amino groups on hydrogel) in DMSO. Beads 4 were washed five times with DMSO and five times with pH 3.0 succinate (20 mM, 1 mM EDTA, 0.01% Tween-20). The sample was washed three times with pH 6.0 sodium phosphate (50 mM, 50 mM ethanolamine, 0.01% Tween-20) and incubated in the same buffer for 1 h at RT. After that the beads were washed five times with pH 3.0 sodium succinate (20 mM, 1 mM EDTA, 0.01% Tween-20).

For determination of maleimide content, an aliquot of hydrogel beads 4 was washed three times with water and ethanol each. The sample was lyophilized and weighed out. Another aliquot of hydrogel beads 4 was reacted with excess mercaptoethanol (in 50 mM sodium phosphate buffer, 30 min at RT), and mercaptoethanol consumption was detected by Ellman test (Ellman, G. L. et al., *Biochem. Pharmacol.*, 1961, 7, 88-95). Maleimide content was determined to be between 0.10 and 0.13 mmol/g dry hydrogel.

Example 5

Synthesis of Linker Reagent 5c

Linker reagent 5c was synthesized according to the following scheme:

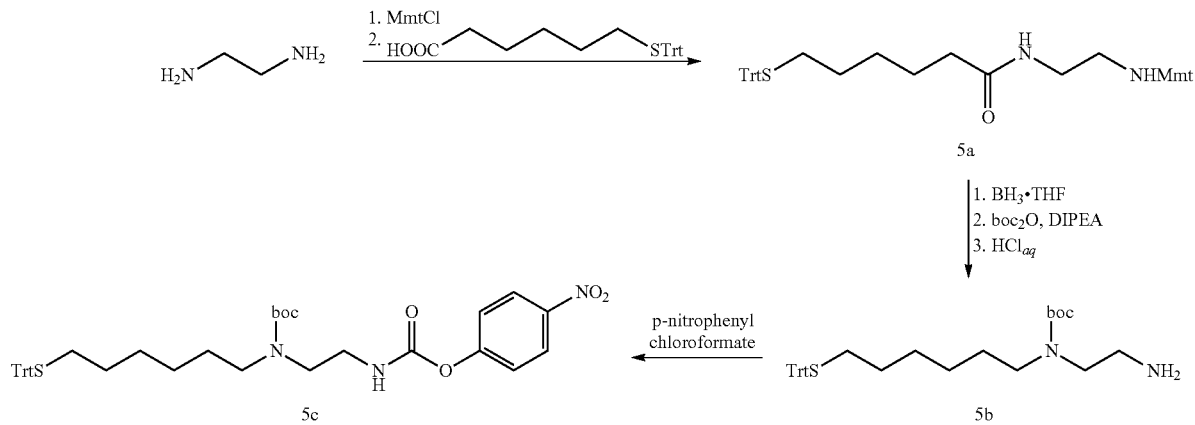

Synthesis of Linker Reagent Intermediate 5a m-Methoxytrityl chloride (3 g, 9.71 mmol) was dissolved in DCM (20 mL) and added dropwise to a solution of ethylenediamine (6.5 mL, 97.1 mmol) in DCM (20 mL). After two hours the solution was poured into diethyl ether (300 mL) and washed three times with 30/1 (v/v) brine/0.1 M NaOH solution (50 ml each) and once with brine (50 mL). The organic phase was dried over $Na_2SO_4$ and volatiles were removed under reduced pressure. Mmt-protected intermediate (3.18 g, 9.56 mmol) was used in the next step without further purification.

The Mmt-protected intermediate (3.18 g, 9.56 mmol) was dissolved in anhydrous DCM (30 mL). 6-(S-Tritylmercapto) hexanoic acid (4.48 g, 11.47 mmol), PyBOP (5.67 g, 11.47 mmol) and DIPEA (5.0 mL, 28.68 mmol) were added and the mixture was agitated for 30 min at RT. The solution was diluted with diethyl ether (250 mL) and washed three times with 30/1 (v/v) brine/0.1 M NaOH solution (50 mL each) and once with brine (50 mL). The organic phase was dried over $Na_2SO_4$ and volatiles were removed under reduced pressure. 5a was purified by flash chromatography.

Yield: 5.69 g (8.09 mmol).

MS: m/z 705.4=$[M+H]^+$ (MW calculated=705.0).

Synthesis of Linker Reagent Intermediate 5b

To a solution of 5a (3.19 g, 4.53 mmol) in anhydrous THF (50 mL) was added $BH_3$-THF (1 M solution, 8.5 mL, 8.5 mmol) and the solution was stirred for 16 h at RT. Further $BH_3$-THF (1 M solution, 14 mL, 14 mmol) was added and stirred for 16 h at RT. The reaction was quenched by addition of methanol (8.5 mL). N,N-dimethyl-ethylenediamine (3 mL, 27.2 mmol) was added and the solution was heated to reflux and stirred for three h. Reaction mixture was allowed to cool down to RT and was then diluted with ethyl acetate (300 mL), washed with saturated, aqueous $Na_2CO_3$ solution (2×100 mL) and saturated, aqueous $NaHCO_3$ solution (2×100 mL). The organic phase was dried over $Na_2SO_4$ and volatiles were removed under reduced pressure to obtain crude amine intermediate (3.22 g).

The amine intermediate (3.22 g) was dissolved in DCM (5 mL). $Boc_2O$ (2.97 g, 13.69 mmol) dissolved in DCM (5 mL) and DIPEA (3.95 mL, 22.65 mmol) were added and the mixture was agitated at RT for 30 min. The mixture was purified by flash chromatography to obtain the crude Boc- and Mmt-protected intermediate (3.00 g).

MS: m/z 791.4=$[M+H]^+$, 519.3=$[M-Mmt+H]^+$ (MW calculated=791.1).

0.4 M aqueous HCl (48 mL) was added to a solution of the Boc- and Mmt-protected intermediate in acetonitrile (45 mL). The mixture was diluted with acetonitrile (10 mL) and stirred for 1 h at RT. Subsequently, the pH value of the reaction mixture was adjusted to 5.5 by addition of 5 M NaOH solution. Acetonitrile was removed under reduced pressure and the aqueous solution was extracted with DCM (4×100 mL). The combined organic phases were dried over $Na_2SO_4$ and volatiles were removed under reduced pressure. Crude 5b was used in the next step without further purification.

Yield: 2.52 g (3.19 mmol).

MS: m/z 519.3=$[M+H]^+$ (MW calculated=519.8 g/mol).

Synthesis of Linker Reagent 5c

Intermediate 5b (985 mg, 1.9 mmol) and p-nitrophenyl chloroformate (330 mg, 2.5 mmol) were dissolved in anhydrous THF (10 mL). DIPEA (0.653 mL, 3.7 mmol) was added and the mixture was stirred for 2 h at RT. The solution was acidified by addition of acetic acid (1 mL). 5c was purified by RP-HPLC.

Yield: 776 mg, (1.13 mmol).

MS m/z 706.3=$[M+Na]^+$ (MW calculated=706.3).

Example 6

Synthesis of Exendin Linker Reagent 6d

Exendin linker reagent 6d was synthesized according to the following scheme:

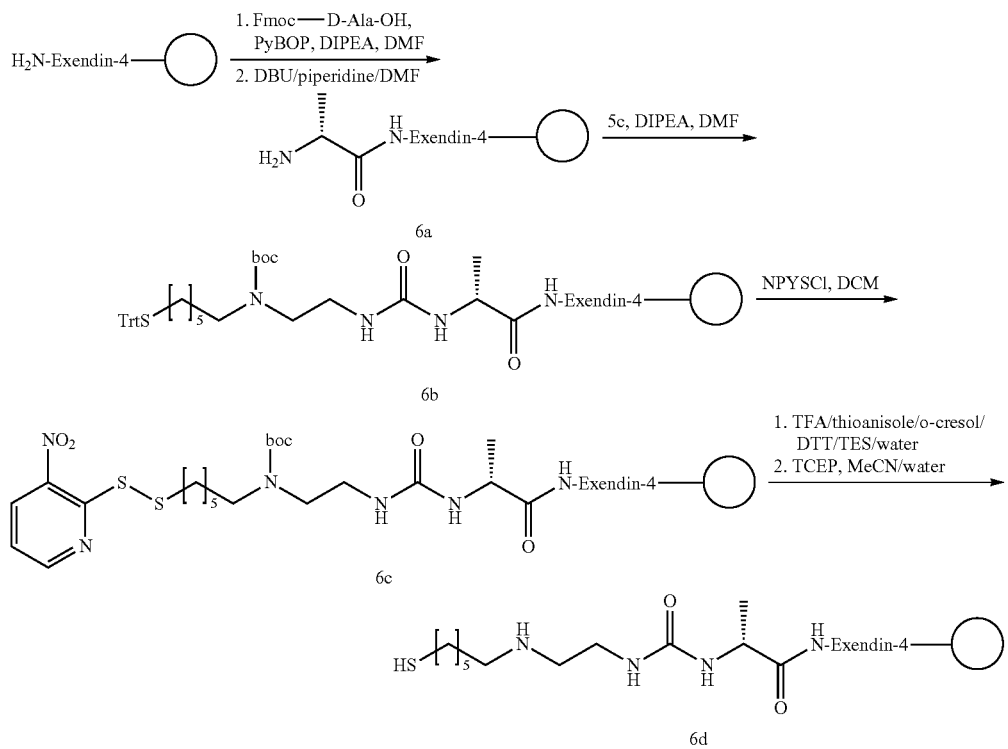

Synthesis of Exendin Linker Reagent Intermediate 6a

Fully side chain protected exendin-4 with free N-terminus on resin (2.00 g, 0.2 mmol, loading approximately 0.1 mmol/g) was transferred into a 20 mL syringe equipped with a filter frit. 8 mL of anhydrous DMF was drawn into the syringe and the syringe was shaken (600 rpm) for 15 min in order to pre-swell the resin. The solvent was discarded, and a solution of Fmoc-D-alanine-OH (187 mg, 0.6 mol), PyBOP (312 mg, 0.6 mmol), and DIPEA (174 µL, 1.0 mmol) in anhydrous DMF (4 mL) was drawn into the syringe. The syringe was shaken at RT and 600 rpm for 60 min. The solution was discharged, and the resin was washed ten times with DMF.

Fmoc-deprotection was performed according to "Materials and Methods".

Synthesis of Exendin Linker Reagent Intermediate 6b

A solution of 5c (137 mg, 0.4 mmol) in anhydrous DMF (3 mL) was added to the resin 6a (0.2 mmol), followed by a solution of DIPEA (80 µL, 0.46 mmol) in anhydrous DMF (4.5 mL), and the reaction mixture was shaken (600 rpm) at 22° C. for 15 hours.

The resin was washed ten times with DMF and ten times with DCM and dried in vacuo.

Synthesis of Exendin Linker Reagent Intermediate 6c

3-Nitro-2-pyridine-sulfenyl chloride (48 mg, 0.25 mmol) was given into a syringe containing 6b (0.05 mmol, 0.5 g). Anhydrous DCM (4 mL) was drawn into the syringe and the mixture was shaken (600 rpm) at RT. After 2 h the solution was discarded and the resin was washed 14 times with DCM and dried in vacuo.

Synthesis of Exendin Linker Reagent Intermediate 6d

In a round bottom flask o-cresol (1.5 mL), thioanisole (1.5 mL), DTT (1.125 g), TES (1.125 mL), and water (1.5 mL) were dissolved in TFA (37.5 mL). 6c (0.15 mmol, 1.5 g) was added to the stirred (250-350 rpm) solution at RT in order to obtain a homogeneous suspension. Stirring was continued for 45 min. The solution was separated from the resin beads by filtration, the beads were washed with TFA twice (2 mL each) and the washing solutions were combined with the filtrate. TFA was removed from the combined solutions in a stream of nitrogen.

Crude 6d was precipitated from the concentrated solution (approx. 10 mL) by addition of diethyl ether (30 mL) and vigorous shaking. After centrifugation (2 min, 5000 rpm) the supernatant was discarded and the precipitate was washed with diethyl ether twice (20 mL each).

Dried precipitate was dissolved in a solution of TCEP (114 mg, 0.39 mmol) in 30 ml 1/19 (v/v) acetonitrile/water containing 0.01% TFA (v/v). Mixture was incubated for 15 hours at RT. 6d was purified by RP-HPLC as described in Materials and Methods using a 150×30 mm Waters XBridge™ BEH300 C18 10 µm column and a flow of 40 ml/min.

Up to 12 mL of the mixture were loaded on the column. The elution was performed using a linear gradient from 5% to 30% solvent B (5 min) followed by a linear gradient from 30% to 35% solvent B (40 min). Fractions containing product 6d were pooled and lyophilized. Purity: 86% (215 nm)

Yield: 85.2 mg (19.2 µmol, starting from 2.00 g resin).

MS m/z 1486.7=[M+3H]$^{3+}$, (MW calculated=4460.0 g/mol).

Example 7

Synthesis of Exendin Linker Reagent 7

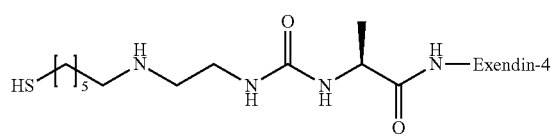

Exendin linker reagent 7 was synthesized as described for exendin linker reagent 6a-6d starting from fully side chain protected exendin-4 on resin with free N-terminus (336 mg, 34 μmol), except the use of Fmoc-L-alanine-OH instead of Fmoc-D-alanine-OH.

Reagents were scaled accordingly in order to obtain the same ratios as were used in 6a-6d.

Yield: 13.4 mg

MS: m/z 1487.4=[M+3H]$^{3+}$ (MW calculated: 4460.0)

Example 8

Synthesis of Exendin Linker Hydrogel 8

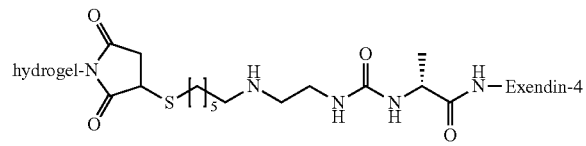

242.5 mg maleimide functionalized hydrogel 4 (25.0 μmol maleimido groups), as suspension in pH 3.0 succinate buffer (20 mM, 1 mM EDTA, 0.01% Tween-20) was filled into a syringe equipped with a filter frit. The hydrogel was washed ten times with 1/1 (v/v) acetonitrile/water containing 0.1% TFA (v/v). A solution of Exendin linker reagent 6d (122.7 mg, 27.5 μmol) in 1/1 (v/v) acetonitrile/water plus 0.1% TFA (3.7 mL) was drawn up and shaken for 2 min at RT to obtain an equilibrated suspension. 334 μL phosphate buffer (pH 7.4, 0.5 M) was added and the syringe was agitated (600 rpm) at RT for 15 min. Consumption of thiol was monitored by Ellman test. The hydrogel was washed 10 times with 1/1 (v/v) acetonitrile/water containing 0.1% TFA (v/v).

Mercaptoethanol (47 μL) was dissolved in 1/1 (v/v) acetonitrile/water plus 0.1% TFA (3 mL) and phosphate buffer (0.5 mL, pH 7.4, 0.5 M). The solution was drawn up into the syringe and the sample was agitated (600 rpm) for 1 h at RT. The solution was discarded and the hydrogel was washed ten times with 1/1 (v/v) acetonitrile/water plus 0.1% TFA. After that the hydrogel was washed ten times with succinate buffer (10 mM succinate, 46 g/L mannitol, 0.05% Tween-20, adjusted with Tris to pH 5.0) and stored at 4° C.

Exendin content of exendin linker hydrogel was determined according to Materials and Methods.

An exendin content of 30% (weight) was obtained.

Example 9

Release Kinetics In Vitro

An aliquot of exendin linker hydrogel 8 (0.5 mg exendin) was transferred into a syringe equipped with a filter frit and washed 5 times with pH 7.4 phosphate buffer (60 mM, 3 mM EDTA, 0.01% Tween-20). The hydrogel was suspended in the same buffer and incubated at 37° C. At defined time points (after 1-7 days incubation time each) the supernatant was exchanged and liberated exendin was quantified by RP-HPLC at 215 nm. UV-signals correlating to liberated exendin were integrated and plotted against incubation time.

Curve-fitting software was applied to estimate the corresponding halftime of release.

A first order release kinetics with a half-life of 45d was obtained (see FIG. 1).

Example 10

Synthesis of Exendin Linker Hydrogel 10

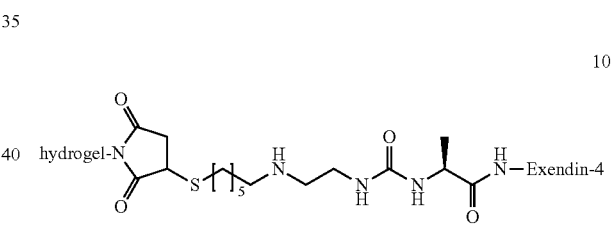

Exendin linker hydrogel 10 was synthesized as described for exendin linker hydrogel 8 except for the use of exendin linker thiol 7 instead of exendin linker thiol 6d.

Exendin content of exendin linker hydrogel was determined according to Materials and Methods. An exendin content of 30.5% (weight) was obtained.

Example 11

Synthesis of Lixisenatide Linker Reagent 11d

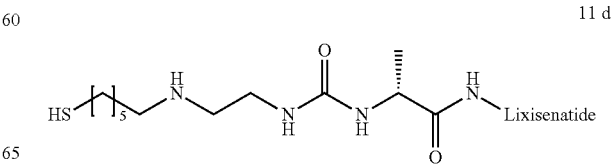

Synthesis Scheme:

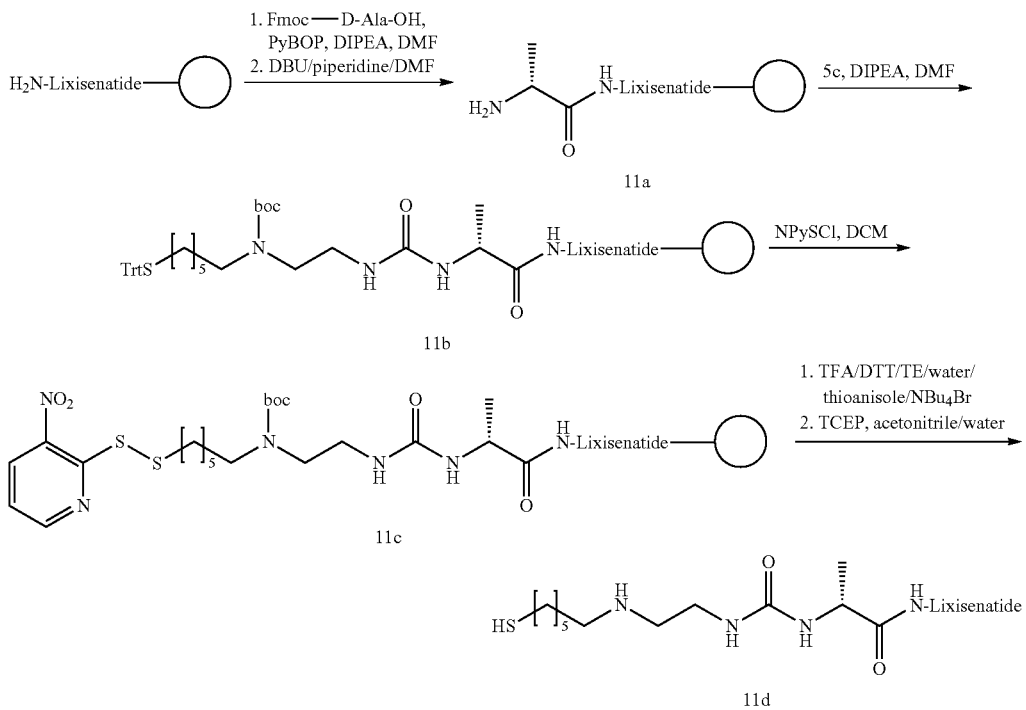

Synthesis of Lixisenatide Linker Reagent Intermediate 11a

Fully side chain protected lixisenatide on resin with free N-terminus (300 mg, loading approximately 0.1 mmol/g) was transferred into a 5 mL syringe equipped with a filter frit. 4 mL of anhydrous DMF was drawn into the syringe and the syringe was shaken (600 rpm) for 15 min in order to pre-swell the resin. The solvent was discarded, and a solution of Fmoc-D-alanine-OH (28 mg, 90 µmol), PyBOP (47 mg, 90 µmol), and DIPEA (26 µL, 150 µmol) in anhydrous DMF (2 mL) was drawn into the syringe. The syringe was shaken at RT and 600 rpm for 60 min. The solution was discharged, and the resin was washed ten times with DMF.

Fmoc-deprotection was performed according to "Materials and Methods".

Synthesis of Lixisenatide Linker Reagent Intermediate 11 b

A solution of 5c (41 mg, 60 µmol) in anhydrous DMF (1.5 mL) was added to the resin 11a (30 µmol), followed by addition of DIPEA (13 µL, 75 µmol), and the homogenized reaction mixture was shaken (600 rpm) at 22° C. for 22 hours.

The resin was washed ten times with DMF and ten times with DCM and dried in vacuo.

Synthesis of Lixisenatide Linker Reagent Intermediate 11c

3-Nitro-2-pyridine-sulfenyl chloride (38 mg, 0.20 mmol) was given into a syringe equipped with a filter frit, containing 11 b. Anhydrous DCM (2 mL) was drawn into the syringe and the mixture was shaken (600 rpm) at RT. After 3.5 h the solution was discarded and the resin was washed 15 times with DCM and dried in vacuo.

Synthesis of Lixisenatide Linker Reagent 11d

In 50 mL-Falcon tube NBu$_4$Br (2.9 mg), thioanisole (58.3 µL), DTT (170 mg), TES (170 µL), and water (113.3 µL) were dissolved in TFA (5.83 mL). 11c (30 µmol) was added to the stirred (200 rpm) solution at RT in order to obtain a homogeneous suspension. Stirring was continued for 1 h. Beads were filtered off and washed with TFA twice (1 mL each). Washing solutions were combined with the filtrate.

Crude 11d was precipitated from the filtrate (approx. 10 mL) by addition of cold diethyl ether (−18° C., 40 mL) and vigorous shaking. The suspension was cooled at −18° C. for further 15 min and centrifuged (2 min, 5000 rpm). The supernatant was discarded and the precipitate was washed with diethyl ether twice (20 mL each) and dried under reduced pressure. Precipitate was dissolved in a solution of TCEP (27 mg, 0.94 µmol) in 2.5 ml 1/1 (v/v) acetonitrile/water containing 0.01% TFA (v/v). Mixture was incubated for 15 hours at RT. 20 mL water was added and 11d was purified by RP-HPLC in two runs by using a linear gradient from 5% to 30% solvent B (5 min) followed by a linear gradient from 30% to 35% solvent B (40 min). A 150×30 mm Waters XBridge™ BEH300 C18 10 µm column and a flow of 40 ml/min was used. Fractions containing product 11d were pooled and lyophilized.

Yield 6.1 mg

MS: m/z 1284.3=$[M+4H]^{4+}$ (MW calculated=5131.9).

Example 12

Synthesis of Lixisenatide Linker Hydrogel 12

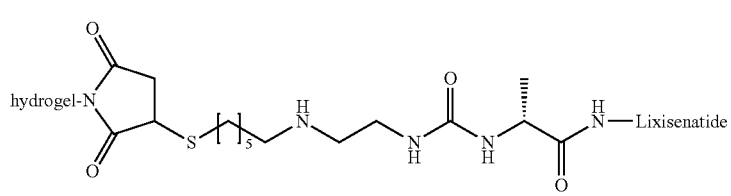

12

Lixisenatide linker hydrogel 12 was synthesized as described for exendin linker hydrogel 8 except for the use of lixisenatide linker thiol 11d instead of exendin linker thiol 6d.

Lixisenatide content of lixisenatide linker hydrogel was determined according to Materials and Methods. A lixisenatide content of 32.4% was obtained.

Example 13

Synthesis of Lixisenatide Linker Reagent 13

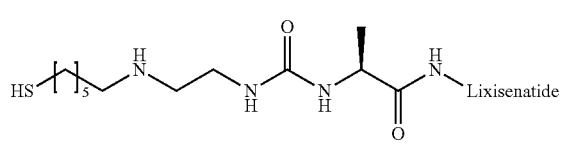

13

Lixisenatide linker reagent 13 was synthesized as described for lixisenatide linker reagent 11a-11d starting from fully side chain protected lixisenatide on resin with free N-terminus (335 mg, 34 µmol), except the use of Fmoc-L-alanine-OH instead of Fmoc-D-alanine-OH. Reagents were scaled accordingly in order to obtain same ratios as were used in 11a-11d.

Yield 7.3 mg

MS: m/z 1283.9=[M+4H]$^{4+}$ (MW calculated=5131.9).

Example 14

Synthesis of Lixisenatide Linker Hydrogel 14

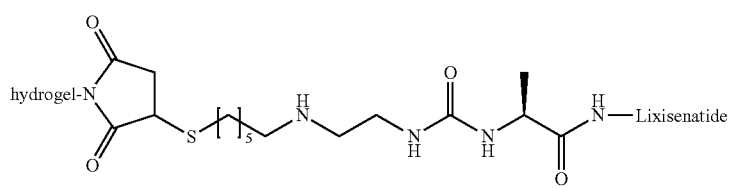

14

Lixisenatide linker hydrogel 14 was synthesized as described for exendin linker hydrogel 8 except for the use of lixisenatide linker thiol 13 instead of exendin linker thiol 6d.

Lixisenatide content of lixisenatide linker hydrogel was determined according to Materials and Methods. A lixisenatide content of 34.5% (weight) was obtained.

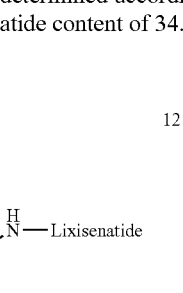

12

Synthesis of GLP-1 Linker Reagent 15

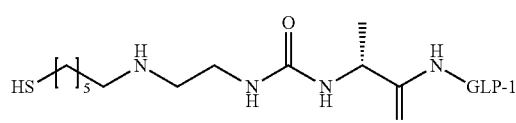

15

GLP-1 linker reagent 15 was synthesized as described for lixisenatide linker reagent 11a-11d except from starting from fully side chain protected GLP-1 on resin with free N-terminus (258 mg, 30 µmol) instead of exendin on resin. Reagents were scaled accordingly in order to obtain same ratios as were used in 11a-11d.

Yield 5.0 mg

MS: m/z 1191.4=[M+3H]$^{3+}$ (MW calculated=3571.1).

Example 16

Synthesis of GLP-1 Linker Hydrogel 16

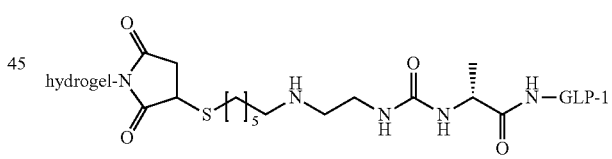

16

GLP-1 linker hydrogel 16 was synthesized as described for exendin linker hydrogel 8 except for the use of GLP-1 linker thiol 15 instead of exendin linker thiol 6d.

GLP-1 content of GLP-1 linker hydrogel was determined according to Materials and Methods. A GLP-1 content of 26.3% (weight) was obtained.

Example 17

Release Kinetics In Vitro

Half life time of release at pH 7.4, 37° C. of exendin from hydrogel 10, of lixisenatide from hydrogels 12 and 14, and of GLP-1 from hydrogel 16 was determined as described in Example 9. Release kinetics of compounds 8, 10, 12, 14 and 16 are shown in FIG. 1.

| Hydrogel | drug | configuration of Ala in linker structure | half life time |
|---|---|---|---|
| 10 | exendin | L | 28 d |
| 12 | lixisenatide | D | 43 d |
| 14 | lixisenatide | L | 27 d |
| 16 | GLP-1 | D | 50 d |
| 8 | exendin | D | 45 d |

Example 18

Synthesis of Linker Reagent 18e

Linker reagent 18e was synthesized according to the following scheme:

sieve) and DIPEA (980 µl, 5.63 mmol) were added. Mixture was stirred for 10 min at 0° C., cooling was removed and mixture stirred for further 20 min at RT. 1 M LiAlH$_4$ in THF (9 mL, 9 mmol) was added and mixture was refluxed for 1.5 h. Reaction was quenched by slowly adding methanol (11 mL) and 100 mL sat. Na/K tartrate solution. Mixture was extracted with ethyl acetate, organic layer was dried over Na$_2$SO$_4$ and solvent was evaporated under reduced pressure. Crude product 18b (1.97 g) was used in the next step without further purification.

MS: m/z 390.2=[M+H]$^+$ (MW calculated=389.6).

A solution of crude product 18b (1.97 g), N-(bromoethyl)-phthalimide (1.43 g, 5.63 mmol) and K$_2$CO$_3$ (1.24 g, 9.0 mmol) in 120 mL acetonitrile was refluxed for 6 h. 60 mL of a sat. NaHCO$_3$ solution was added and mixture was extracted 3× with ethyl acetate. Combined organics were dried (Na$_2$SO$_4$) and solvent was removed under reduced pressure. Phthalimide 18c was purified on silica by using heptane (containing 0.02% NEt$_3$) and an ascending amount of ethyl acetate (containing 0.02% NEt$_3$) as eluents.

Yield: 0.82 g (1.46 mmol)

MS: m/z 563.3=[M+H]$^+$ (MW calculated=562.8).

Phthalimide 18c (819 mg 1.46 mmol) was dissolved in 35 mL ethanol and hydrazine hydrate (176 µl, 3.64 mmol) was added. Mixture was refluxed for 3 h. Precipitate was filtered off. Solvent was removed under reduced pressure and residue was treated with 15 mL dichloromethane. Precipitate was filtered off and dichloromethane was removed under reduced pressure. Residue was purified by RP HPLC. Pooled HPLC fractions were adjusted to pH 7 by adding NaHCO$_3$ and

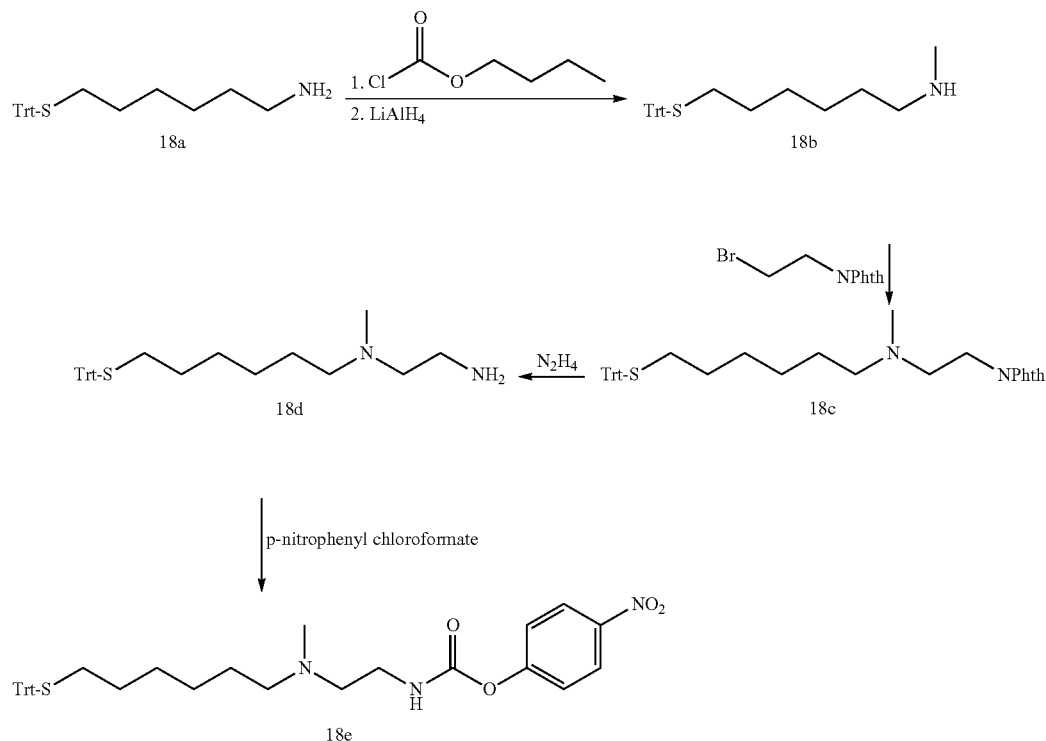

Synthesis of linker reagent intermediate 18b was performed under nitrogen atmosphere. A solution of amine 18a (1.69 g, 4.5 mmol, for preparation see WO-A 2009/133137) in 30 mL THF (dry, mol. sieve) was cooled to 0° C. Butyl chloroformate (630 µl, 4.95 mmol) in 3 mL THF (dry, mol.

extracted several times with dichloromethane. Combined organics were dried (Na$_2$SO$_4$) and solvent was removed under reduced pressure to yield amine 18d.

Yield: 579 mg (1.34 mmol)

MS: m/z 433.3=[M+H]$^+$ (MW calculated=432.7).

Para-nitrophenyl chloroformate (483 mg, 2.40 mmol) was dissolved in 10 mL dichloromethane (dry, mol. sieve). A solution of amine 18d (1.00 g, 2.31 mmol) in 5 mL dichloromethane (dry, mol. sieve) and 1.8 mL of sym-collidine were added and mixture was stirred at room temperature for 40 min. Dichloromethane was removed under reduced pressure, residue was acidified with acetic acid and purified by RP-HPLC to yield para-nitrophenyl carbamate 18e.

Yield: 339 mg (0.57 mmol)

MS: m/z 598.3=[M+H]$^+$ (MW calculated=597.8).

Synthesis of GLP-1 Linker Reagent 19

19

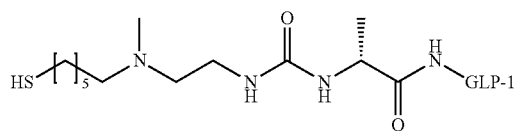

GLP-1 linker reagent 19 was synthesized as described for GLP-1 linker reagent 15 except for the use of linker reagent 18e instead of linker reagent 5c, starting from fully side chain protected GLP-1 on resin with free N-terminus (150 mg, 16.5 μmol). Reagents were scaled accordingly in order to obtain same ratios as were used in 11a-11d.

Yield 1.33 mg

MS: m/z 1196.0=[M+3H]$^{3+}$ (MW calculated=3585.1).

Example 20

Synthesis of GLP-1 Linker Hydrogel 20

20

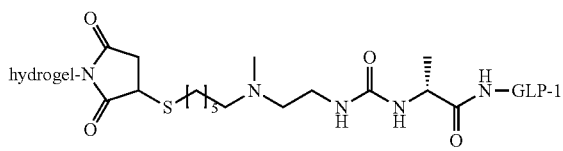

GLP-1 linker hydrogel 20 was synthesized as described for exendin linker hydrogel 8 except for the use of GLP-1 linker thiol 19 instead of exendin linker thiol 6d.

Abbreviations:
AcOH acetic acid
AcOEt ethyl acetate
Bn benzyl
Boc t-butyloxycarbonyl
DBU 1,3-diazabicyclo[5.4.0]undecene
DCC N,N-dicyclohexylcarbodiimid
DCM dichloromethane
DIPEA diisopropylethylamine
DMAP dimethylamino-pyridine
DMF N,N-dimethylformamide
DMSO dimethylsulfoxide
DTT DL dithiothreitol
EDC 1-Ethyl-3-(3-dimethylaminopropyl)carbodiimid
EDTA ethylenediaminetetraacetic acid
eq stoichiometric equivalent
EtOH ethanol
Fmoc 9-fluorenylmethoxycarbonyl
HPLC high performance liquid chromatography
HOBt N-hydroxybenzotriazole
iPrOH 2-propanol
LCMS mass spectrometry-coupled liquid chromatography
Mal 3-maleimido propyl
Mal-PEG6-NHS N-(3-maleimidopropyl)-21-amino-4,7,10,13,16,19-hexaoxa-heneicosanoic acid NHS ester
Me methyl
MeOH methanol
Mmt 4-methoxytrityl
MS mass spectrum/mass spectrometry
MTBE methyl tert.-butyl ether
MW molecular mass
NHS N-hydroxy succinimide
PEG poly(ethylene glycol)
PyBOP benzotriazole-1-yl-oxy-tris-pyrrolidino-phosphonium
hexafluorophosphate
Phth phthalimido
RP-HPLC reversed-phase high performance liquid chromatography
rpm rounds per minute
RT room temperature
SEC size exclusion chromatography
TCEP tris(2-carboxyethyl)phosphine hydrochloride
TES triethylsilane
TFA trifluoroacetic acid
THF tetrahydrofurane
TMEDA N,N,N'N'-tetramethylethylene diamine
Tris tris(hydroxymethyl)aminomethane
Trt triphenylmethyl, trityl
UPLC ultra performance liquid chromatography
V volume

SEQUENCE LISTING

```
<160> NUMBER OF SEQ ID NOS: 22

<210> SEQ ID NO 1
<211> LENGTH: 39
<212> TYPE: PRT
<213> ORGANISM: artificial
<220> FEATURE:
<223> OTHER INFORMATION: Heloderma suspectum
<220> FEATURE:
<221> NAME/KEY: MOD_RES
<222> LOCATION: (39)..(39)
<223> OTHER INFORMATION: Heloderma suspectum

<400> SEQUENCE: 1
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Heloderma horridum
<220> FEATURE:
<221> NAME/KEY: MOD_RES
<222> LOCATION: (39)..(39)
<223> OTHER INFORMATION: AMIDATION

<400> SEQUENCE: 2

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 31
<212> TYPE: PRT
<213> ORGANISM: artificial
<220> FEATURE:
<223> OTHER INFORMATION: Exendin/Exendin agonist

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 4
<211> LENGTH: 31
<212> TYPE: PRT
<213> ORGANISM: artificial
<220> FEATURE:
<223> OTHER INFORMATION: Exendin/Exendin agonist

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Tyr
            20                  25                  30

<210> SEQ ID NO 5
<211> LENGTH: 30
<212> TYPE: PRT
<213> ORGANISM: artificial
<220> FEATURE:
<223> OTHER INFORMATION: Exendin/Exendin agnoist

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

-continued

```
<210> SEQ ID NO 6
<211> LENGTH: 30
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (30)..(30)
<223> OTHER INFORMATION: AMIDATION

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 7
<211> LENGTH: 28
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (28)..(28)
<223> OTHER INFORMATION: AMIDATION

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 8
<211> LENGTH: 39
<212> TYPE: PRT
<213> ORGANISM: Artificial
<220> FEATURE:
<223> OTHER INFORMATION: Exendin/Exendin agnoist
<220> FEATURE:
<221> NAME/KEY: MOD_RES
<222> LOCATION: (39)..(39)
<223> OTHER INFORMATION: amidation

<400> SEQUENCE: 8

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 9
<211> LENGTH: 28
<212> TYPE: PRT
<213> ORGANISM: artificial
<220> FEATURE:
<223> OTHER INFORMATION: Exendin/Exendin/agnoist
<220> FEATURE:
<221> NAME/KEY: MOD_RES
<222> LOCATION: (28)..(28)
<223> OTHER INFORMATION: AMIDATION

<400> SEQUENCE: 9

His Gly Glu Gly Thr Phe Thr Ser Asp Leu Ser Lys Gln Leu Glu Glu
1               5                   10                  15
```

-continued

Glu Ala Val Arg Leu Phe Ile Glu Phe Leu Lys Asn
            20                  25

<210> SEQ ID NO 10
<211> LENGTH: 28
<212> TYPE: PRT
<213> ORGANISM: artificial
<220> FEATURE:
<223> OTHER INFORMATION: Exendin/Exendin agnoist
<220> FEATURE:
<221> NAME/KEY: MOD_RES
<222> LOCATION: (28)..(28)
<223> OTHER INFORMATION: AMIDATION

<400> SEQUENCE: 10

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 11
<211> LENGTH: 39
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (39)..(39)
<223> OTHER INFORMATION: AMIDATION

<400> SEQUENCE: 11

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 12
<211> LENGTH: 39
<212> TYPE: PRT
<213> ORGANISM: Artificial
<220> FEATURE:
<223> OTHER INFORMATION: Exendin/Exendin agnoist
<220> FEATURE:
<221> NAME/KEY: MOD_RES
<222> LOCATION: (39)..(39)
<223> OTHER INFORMATION: AMIDATION

<400> SEQUENCE: 12

His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 13
<211> LENGTH: 30
<212> TYPE: PRT
<213> ORGANISM: artificial
<220> FEATURE:
<223> OTHER INFORMATION: GLP-1(7-37)
<220> FEATURE:
<221> NAME/KEY: MOD_RES
<222> LOCATION: (30)..(30)

<223> OTHER INFORMATION: AMIDATION

<400> SEQUENCE: 13

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 14
<211> LENGTH: 30
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (30)..(30)
<223> OTHER INFORMATION: AMIDATION

<400> SEQUENCE: 14

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 15
<211> LENGTH: 31
<212> TYPE: PRT
<213> ORGANISM: artificial
<220> FEATURE:
<223> OTHER INFORMATION: GLP-1(7-37)

<400> SEQUENCE: 15

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 16
<211> LENGTH: 30
<212> TYPE: PRT
<213> ORGANISM: artificial
<220> FEATURE:
<223> OTHER INFORMATION: Exendin/Exendin agonist
<220> FEATURE:
<221> NAME/KEY: VARIANT
<222> LOCATION: (3)..(3)
<223> OTHER INFORMATION: Xaa = Pro, Phe or Tyr
<220> FEATURE:
<221> NAME/KEY: MOD_RES
<222> LOCATION: (30)..(30)
<223> OTHER INFORMATION: AMIDATION

<400> SEQUENCE: 16

His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 17
<211> LENGTH: 30
<212> TYPE: PRT
<213> ORGANISM: artificial
<220> FEATURE:
<223> OTHER INFORMATION: Exendin/Exendin agonist
<220> FEATURE:
<221> NAME/KEY: VARIANT

```
<222> LOCATION: (2)..(2)
<223> OTHER INFORMATION: Xaa = Tyr, alpha aminobutyric acid (Abu), Val,
      D-Ala or Gly
<220> FEATURE:
<221> NAME/KEY: MOD_RES
<222> LOCATION: (30)..(30)
<223> OTHER INFORMATION: AMIDATION

<400> SEQUENCE: 17

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 18
<211> LENGTH: 30
<212> TYPE: PRT
<213> ORGANISM: artificial
<220> FEATURE:
<223> OTHER INFORMATION: Exendin/Exendin agonist

<400> SEQUENCE: 18

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly
            20                  25                  30

<210> SEQ ID NO 19
<211> LENGTH: 30
<212> TYPE: PRT
<213> ORGANISM: artificial
<220> FEATURE:
<223> OTHER INFORMATION: Exendin/Exendin agnoist
<220> FEATURE:
<221> NAME/KEY: MOD_RES
<222> LOCATION: (1)..(1)
<223> OTHER INFORMATION: modification: acetyl, pryoglytamyl, N-2-
      hydroybenzoyl, N-trans-3-hexenoyl
<220> FEATURE:
<221> NAME/KEY: MOD_RES
<222> LOCATION: (30)..(30)
<223> OTHER INFORMATION: AMIDATION

<400> SEQUENCE: 19

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 20
<211> LENGTH: 31
<212> TYPE: PRT
<213> ORGANISM: artificial
<220> FEATURE:
<223> OTHER INFORMATION: Exendin/Exendin agnoist
<220> FEATURE:
<221> NAME/KEY: MOD_RES
<222> LOCATION: (2)..(2)
<223> OTHER INFORMATION: Xaa = 6-amino-hexanoyl
<220> FEATURE:
<221> NAME/KEY: MOD_RES
<222> LOCATION: (31)..(31)
<223> OTHER INFORMATION: AMIDATION

<400> SEQUENCE: 20

His Xaa Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg
            20                  25                  30
```

```
<210> SEQ ID NO 21
<211> LENGTH: 44
<212> TYPE: PRT
<213> ORGANISM: artificial
<220> FEATURE:
<223> OTHER INFORMATION: Lixisenatide
<220> FEATURE:
<221> NAME/KEY: MOD_RES
<222> LOCATION: (44)..(44)
<223> OTHER INFORMATION: AMIDATION

<400> SEQUENCE: 21

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 22
<211> LENGTH: 31
<212> TYPE: PRT
<213> ORGANISM: Artificial Sequence
<220> FEATURE:
<223> OTHER INFORMATION: exendin/exendin agonist
<220> FEATURE:
<221> NAME/KEY: MOD_RES
<222> LOCATION: (20)..(20)
<223> OTHER INFORMATION: Xaa = Lys(N-epsilon(gamma-glutamyl(N-alpha-
      hexadecanoyl)))
<220> FEATURE:
<221> NAME/KEY: MOD_RES
<222> LOCATION: (31)..(31)
<223> OTHER INFORMATION: AMIDATION

<400> SEQUENCE: 22

His Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg GLY
            20                  25                  30
```

The invention claimed is:

1. A prodrug or a pharmaceutically acceptable salt thereof comprising an exendin linker conjugate D-$L^1$ and a hydrogel Z with backbone moieties of formula C-(A-Hyp)$_4$, wherein each A is independently selected from the formula —(CH$_2$)$_{n1}$(OCH$_2$CH$_2$)$_n$X—,
wherein:
n1 is 1 or 2;
n is an integer ranging from 5 to 50; and
X is an amide linkage linking A and Hyp;
each Hyp is independently selected from hyperbranched polypeptides comprising lysine;
the backbone moieties are crosslinked by poly(ethylene glycol)-based crosslinker moieties, comprising m ethylene glycol units, wherein m is an integer ranging from 3-100, and terminated by at least two hydrolytically degradable bonds;
a linker $L^2$ connected to a backbone moiety, wherein:
$L^2$ is a single chemical bond or is a $C_{1-20}$ alkyl chain, which is optionally interrupted by one or more groups independently selected from —O— and C(O)N ($R^{3aa}$) and is optionally substituted with one or more groups independently selected from OH and C(O)N ($R^{3aa}R^{3aaa}$), wherein $R^{3aa}$ and $R^{3aaa}$ are independently selected from the group consisting of H and $C_{1-4}$ alkyl; and
$L^2$ is attached to Z via a terminal group selected from the group consisting of

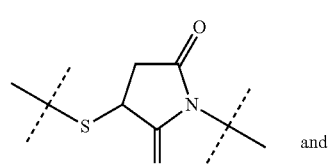

X

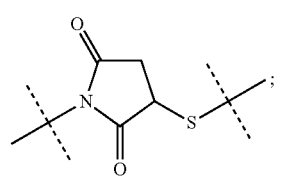

XI

;

wherein L² is attached to the sulfur atom in structure X and Z is attached to the nitrogen atom in structure X or L² is attached to the nitrogen atom in structure XI and Z is attached to the sulfur atom in structure XI;
and D is an exendin and
-L¹ is of formula (I),

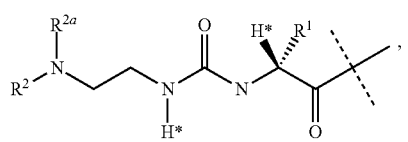
(I)

wherein the dashed line indicates attachment of L¹ to one of the amino groups of the exendin through an amide bond;
R¹ is selected from $C_{1-4}$ alkyl;
R² and $R^{2a}$ are independently selected from the group consisting of H and $C_{1-4}$ alkyl;
L¹ is substituted with one L²-Z, wherein L²-Z replaces one of the hydrogen atoms in R¹, R² or $R^{2a}$, provided that the hydrogens marked with the asterisks in formula (I) are not replaced.

2. The prodrug of claim 1, wherein L¹ is not further substituted.

3. The prodrug of claim 1, wherein R¹ is —CH₃.

4. The prodrug of claim 1, wherein L¹ is represented by formula (Ia)

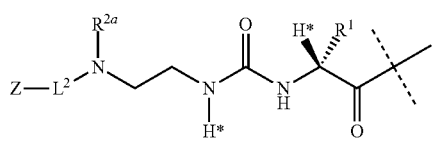
(Ia)

wherein the dashed line indicates attachment to the nitrogen of the exendin by forming an amide bond.

5. The prodrug of claim 1, wherein L¹ is represented by formula (II)

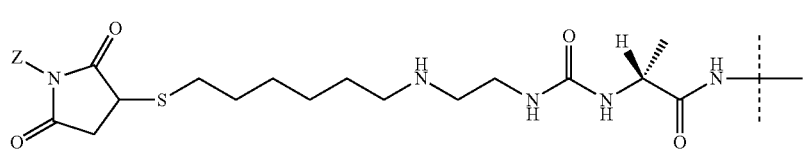
(II)

wherein the dashed line indicates attachment to the nitrogen of the exendin by forming an amide bond.

6. The prodrug of claim 1, wherein the backbone moieties comprise a branching core of the following formula

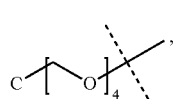

wherein the dashed line indicates attachment to the remainder of the backbone moiety.

7. The prodrug of claim 1, wherein the backbone moieties comprise a structure of the following formula:

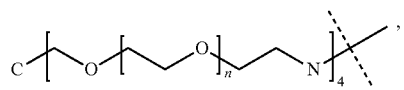

wherein n is an integer of from 5 to 50 and the dashed line indicates attachment to the rest of the molecule.

8. The prodrug of claim 1, wherein the backbone moieties comprise a hyperbranched moiety Hyp of the following formula:

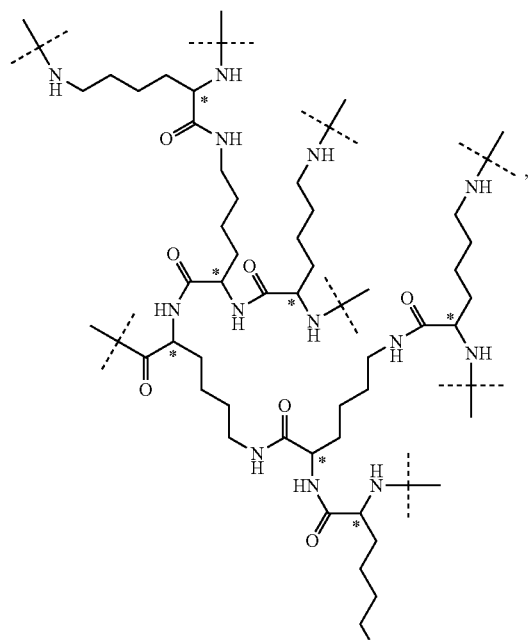

-continued

wherein the dashed lines indicate attachment to the rest of the molecule; and carbon atoms marked with asterisks indicate S-configuration.

9. The prodrug of claim 1, wherein the backbone moieties are attached to at least one spacer of the following formula:

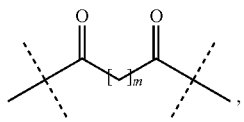

wherein one of the dashed lines indicates attachment to the hyperbranched moiety Hyp and the second dashed line indicates attachment to the rest of the molecule; and wherein m is an integer of from 2 to 4.

10. The prodrug of claim 1, wherein the backbone moieties are attached to at least one spacer of the following formula:

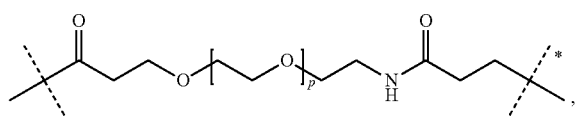

wherein the dashed line marked with the asterisk indicates the bond between the hydrogel and the N of the thiosuccinimide group of claim 1;
wherein the other dashed line indicates attachment to Hyp; and wherein p is an integer of from 0 to 10.

11. The prodrug of claim 1, wherein the backbone moieties are linked through crosslinker moieties comprising the following structure

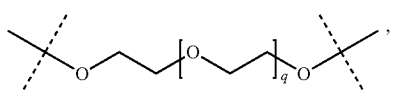

wherein q is an integer from 5 to 50.

12. A pharmaceutical composition comprising the prodrug of claim 1 or a pharmaceutical salt thereof together with at least one pharmaceutically acceptable excipient.

13. The prodrug of claim 1, wherein the crosslinker moieties have molecular weights in the range of from 0.5 KDa to 5 KDa.

14. The prodrug of claim 1, $R^2$ is replaced by $L^2$-Z.

15. The prodrug of claim 1, $R^1$ is $CH_2$-$L^2$-Z.

16. The prodrug of claim 1, in the form of microparticulate beads.

17. The prodrug of claim 16, wherein the microparticulate beads have a diameter ranging from 1 to 500 micrometers.

18. The prodrug of claim 1, wherein the exendin is a compound selected from the group consisting of SEQ. ID NOS.1-22.

19. The prodrug of claim 18, wherein the exendin is a compound of SEQ. ID NO. 1, SEQ. ID NO.13, SEQ. ID NO. 15, SEQ. ID NO. 21 or SEQ. ID NO. 22.

20. The prodrug of claim 19, wherein the exendin is a compound of SEQ. ID NO. 1, SEQ. ID NO. 13 or SEQ. ID NO. 21.

21. The prodrug of claim 1, wherein the exendin is lixisenatide.

22. The prodrug of claim 1, wherein the exendin is attached to $L^1$ through an N-terminal nitrogen of the exendin.

23. A method of treating a disease or disorder selected from the group consisting of hyperglycemia, pre-diabetes, impaired glucose tolerance, diabetes type 1, and diabetes type II, comprising administering to a patient in need thereof a therapeutically effective amount of the pharmaceutical composition of claim 12.

24. A process for the preparation of the prodrug of claim 1, comprising the steps of:
(a) contacting at a temperature between room temperature and 4° C. in a buffered aqueous solution of pH 5.5-8 an aqueous suspension comprising microparticles of the hydrogel of claim 1, with a solution comprising an exendin-linker reagent D-L*, wherein said hydrogel is a maleimide-functionalized hydrogel,
D is an exendin; and
-L* is a formula (IV),

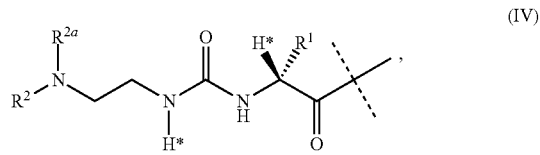

wherein the dashed line indicates the attachment to one of the amino groups of the exendin by forming an amide bond;
$R^1$ is selected from $C_{1-4}$ alkyl;
$R^2$, $R^{2a}$, are independently selected from the group consisting of H and $C_{1-4}$ alkyl,
wherein L* is substituted with one $L^{2*}$ and optionally further substituted, provided that the hydrogens marked with the asterisks in formula (IV) are not replaced by a substituent and wherein
$L^{2*}$ is a spacer connected to L* and comprising a chemical functional group intended for conjugation to a hydrogel wherein the chemical functional group of $L^{2*}$ comprises a thiol group, resulting in an exendin-linker-hydrogel conjugate; and
(b) optionally, treating the exendin-linker-hydrogel conjugate from step (a) with a thiol-containing compound of 34 Da to 500 Da at temperatures between room temperature and 4° C. in a buffered aqueous solution of pH 5.5-8.

25. A process for the preparation of the prodrug of claim 1, comprising the steps of
(a) contacting at a temperature between room temperature and 4° C. in a buffered aqueous solution of pH 5.5-8 an aqueous suspension comprising microparticles of a hydrogel of claim 1 with a solution comprising an exendin-linker D-L*, wherein said hydrogel is a thiol functionalized hydrogel;
D is an exendin moiety; and
-L* is formula (IV),

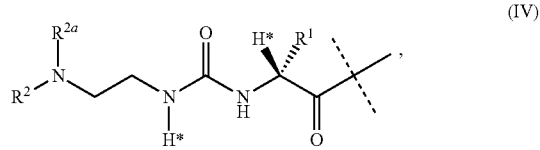

wherein the dashed line indicates the attachment to one of the amino groups of the exendin by forming an amide bond;
$R^1$ is selected from $C_{1-4}$ alkyl;
$R^2$, $R^{2a}$, are independently selected from the group consisting of H and $C_{1-4}$ alkyl, wherein L* is substituted with one $L^{2*}$ and optionally further substituted, provided that the hydrogens marked with the asterisks in formula (IV) are not replaced by a substituent and wherein $L^2*$ is a spacer connected to L* and comprising a chemical functional group intended for conjugation to a hydrogel wherein the chemical functional group of $L^2*$ comprises a maleimide group resulting in an exendin-linker-hydrogel conjugate; and (b) optionally, treating the exendin-linker-hydrogel conjugate from step (a) with a maleimide-containing compound of 100 to 300 Da at temperatures between room temperature and 4° C. in a buffered aqueous solution of pH 5.5-8.

26. A process for preparing a needle injectable prodrug comprising the steps of:
   (a) preparing the prodrug of claim 1 in the form of microparticles;
   (b) sieving the microparticles;
   (c) selecting a fraction with a prodrug bead diameter of between 25 and 80 μm; and
   (d) suspending the bead fraction of step (c) in an aqueous buffer solution suitable for injection.

* * * * *

UNITED STATES PATENT AND TRADEMARK OFFICE
CERTIFICATE OF CORRECTION

PATENT NO. : 9,133,276 B2
APPLICATION NO. : 13/822170
DATED : September 15, 2015
INVENTOR(S) : Felix Cleemann et al.

Page 1 of 3

It is certified that error appears in the above-identified patent and that said Letters Patent is hereby corrected as shown below:

Page 1 of the title page, right-hand column, item (56), section "OTHER PUBLICATIONS", line 6: please replace "e al.:" with --et al.:--;

Page 1 of the title page, right-hand column, item (57), section "ABSTRACT":

please replace " 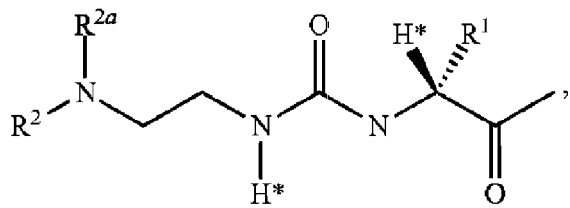 " with 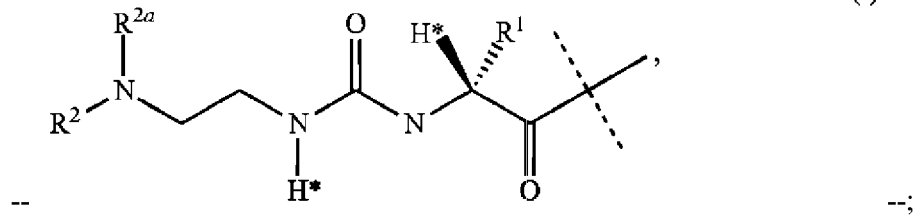 --;

Page 2 of the title page, right-hand column, item (56), section "OTHER PUBLICATIONS", line 2: please replace "ofExendin-4:" with --of Exendin-4:--;

Page 2 of the title page, right-hand column, item (56), section "OTHER PUBLICATIONS", line 54: please replace "theDiscovery" with --the Discovery--;

Page 3 of the title page, left-hand column, item (56), section "OTHER PUBLICATIONS", line 28: please insert --Definition of moiety, from http://dictionary.reference.com/browse/moieties, pp. 1-3, accessed Aug. 26, 2010.-- before "Definition of the like,";

Signed and Sealed this
Fourteenth Day of June, 2016

Michelle K. Lee
*Director of the United States Patent and Trademark Office*

CERTIFICATE OF CORRECTION (continued)
U.S. Pat. No. 9,133,276 B2

Page 3 of the title page, left-hand column, item (56), section "OTHER PUBLICATIONS", line 42: please replace "determinationof" with --determination of--;

Page 3 of the title page, left-hand column, item (56), section "OTHER PUBLICATIONS", line 59: please replace "oflnsulin-secreting B-Cells" with --of Insulin-secreting β-Cells--;

Page 3 of the title page, left-hand column, item (56), section "OTHER PUBLICATIONS", line 60: please replace "Chern.," with --Chem.,--;

Page 3 of the title page, left-hand column, item (56), section "OTHER PUBLICATIONS", line 64: please replace "Chern." with --Chem.--;

Page 3 of the title page, right-hand column, item (56), section "OTHER PUBLICATIONS", line 16: please replace "peptide-!" with --peptide-1--;

Page 3 of the title page, right-hand column, item (56), section "OTHER PUBLICATIONS", line 63: please replace "ofExenatide" with --of Exenatide--;

Page 3 of the title page, right-hand column, item (56), section "OTHER PUBLICATIONS", line 66: please replace "1,6-Eiimination:" with --1,6-Elimination:--;

Page 4 of the title page, left-hand column, item (56), section "OTHER PUBLICATIONS", line 17: please replace "Radiation-corsslinked" with --Radiation-crosslinked--;

Page 4 of the title page, left-hand column, item (56), section "OTHER PUBLICATIONS", line 29: please replace "I28." with --128.--;

Page 4 of the title page, left-hand column, item (56), section "OTHER PUBLICATIONS", line 52: please replace "Copolymer-bela-lactamase" with --Copolymer-beta-lactamase--;

Page 4 of the title page, right-hand column, item (56), section "OTHER PUBLICATIONS", line 1: please replace "[2-Sulfo-9-fluorenylmethoxycarbonylh-exendin-4-a" with --[2-Sulfo-9-fluorenylmethoxycarbonyl]$_3$-exendin-4-a--;

Page 4 of the title page, right-hand column, item (56), section "OTHER PUBLICATIONS", line 14: please replace "chemica l cleavage" with --chemical cleavage--;

Page 5 of the title page, right-hand column, item (56), section "OTHER PUBLICATIONS", line 8: please replace "(=Phamlaccutical" with --(=Pharmaceutical--; and

CERTIFICATE OF CORRECTION (continued)
U.S. Pat. No. 9,133,276 B2

In the claims:

At Column 78, claim number 8, line number 18: please replace the interrupted chemical structure

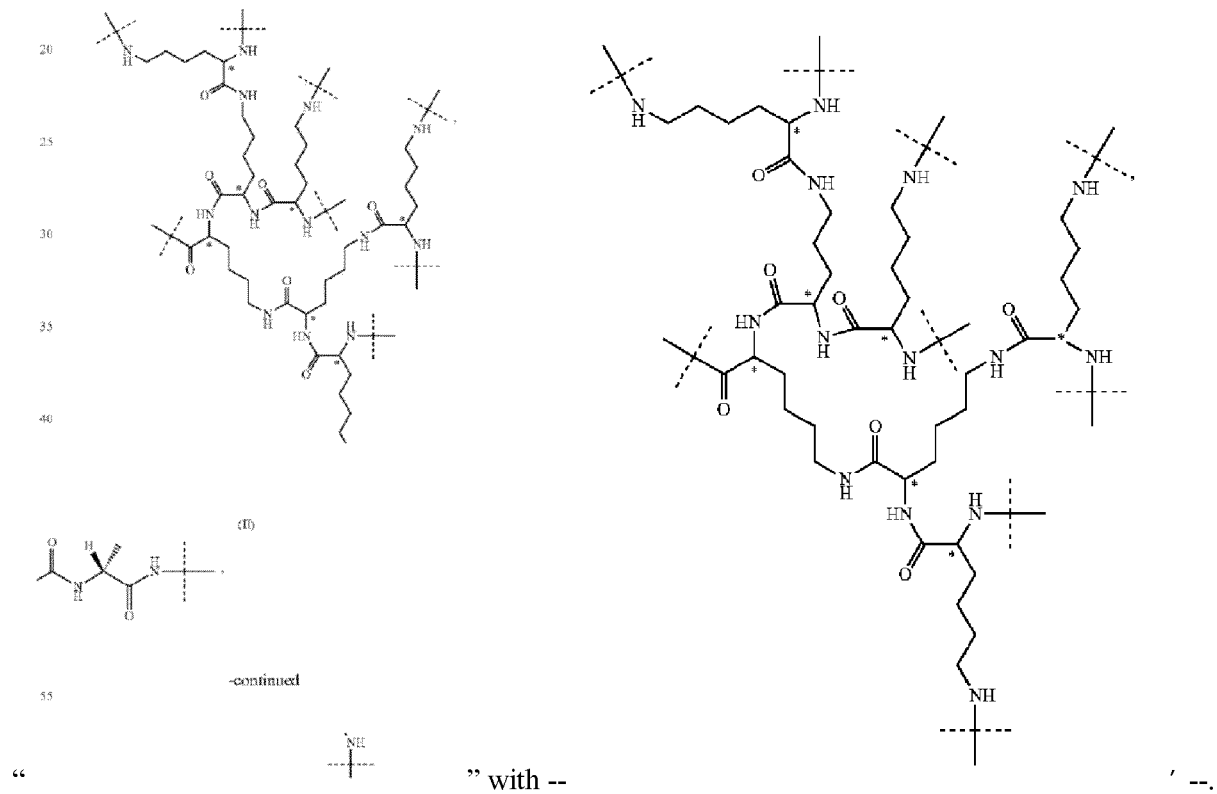

" with -- ' --.